(12) United States Patent
Biswas

(10) Patent No.: US 11,446,224 B2
(45) Date of Patent: Sep. 20, 2022

(54) GEL COMPOSITION

(71) Applicant: AJINOMOTO CO., INC., Tokyo (JP)

(72) Inventor: Shuvendu Biswas, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 149 days.

(21) Appl. No.: 16/289,857

(22) Filed: Mar. 1, 2019

(65) Prior Publication Data

US 2019/0192404 A1  Jun. 27, 2019

Related U.S. Application Data

(63) Continuation of application No. PCT/JP2017/038414, filed on Oct. 24, 2017.

(30) Foreign Application Priority Data

| Oct. 24, 2016 | (JP) | JP2016-208183 |
| Oct. 24, 2016 | (JP) | JP2016-208184 |
| Feb. 17, 2017 | (JP) | JP2017-028516 |
| Mar. 27, 2017 | (JP) | JP2017-061620 |

(51) Int. Cl.

| A61K 8/44 | (2006.01) |
| A61K 8/368 | (2006.01) |
| A61K 8/92 | (2006.01) |
| A61K 8/04 | (2006.01) |
| A61K 8/34 | (2006.01) |
| A61K 8/39 | (2006.01) |
| A61K 8/36 | (2006.01) |
| A61Q 19/00 | (2006.01) |
| A61K 8/31 | (2006.01) |
| A61K 8/58 | (2006.01) |
| A61Q 1/04 | (2006.01) |
| A61Q 5/00 | (2006.01) |
| A61Q 1/06 | (2006.01) |
| A61Q 1/14 | (2006.01) |
| A61Q 17/04 | (2006.01) |
| A61K 8/86 | (2006.01) |

(52) U.S. Cl.
CPC ............ *A61K 8/442* (2013.01); *A61K 8/042* (2013.01); *A61K 8/31* (2013.01); *A61K 8/34* (2013.01); *A61K 8/342* (2013.01); *A61K 8/361* (2013.01); *A61K 8/368* (2013.01); *A61K 8/39* (2013.01); *A61K 8/585* (2013.01); *A61K 8/86* (2013.01); *A61K 8/92* (2013.01); *A61K 8/922* (2013.01); *A61Q 19/00* (2013.01); *A61K 2800/10* (2013.01); *A61Q 1/04* (2013.01); *A61Q 1/06* (2013.01); *A61Q 1/14* (2013.01); *A61Q 5/00* (2013.01); *A61Q 17/04* (2013.01)

(58) Field of Classification Search
CPC .......... A61K 8/442; A61K 8/042; A61K 8/31; A61K 8/34; A61K 8/342; A61K 8/361; A61K 8/368; A61K 8/39; A61K 8/585; A61K 8/86; A61K 8/92; A61K 8/922; A61K 2800/10; A61Q 19/00; A61Q 1/04; A61Q 1/06; A61Q 1/14; A61Q 5/00; A61Q 17/04

See application file for complete search history.

(56) References Cited

U.S. PATENT DOCUMENTS

| 7,347,990 | B2 | 3/2008 | Emslie et al. |
| 8,591,871 | B2 | 11/2013 | Do et al. |
| 8,999,304 | B2 | 4/2015 | Bui et al. |
| 9,272,039 | B2 | 3/2016 | Bui et al. |
| 2002/0159961 | A1 | 10/2002 | Yamato et al. |
| 2003/0219395 | A1 | 11/2003 | Sakuta |

(Continued)

FOREIGN PATENT DOCUMENTS

| EP | 3 574 889 A1 | 12/2019 |
| JP | 1-163228 A | 6/1989 |

(Continued)

OTHER PUBLICATIONS

Yoshida, M., "AJK Series: New Gelling Agent", Kokyu Alcohol Kogyo Co., Ltd, vol. 61, No. 8, 2008, pp. 136 and 74-80 (with cover page and English translation).

(Continued)

*Primary Examiner* — James D. Anderson
*Assistant Examiner* — William Y Lee
(74) *Attorney, Agent, or Firm* — Oblon, McClelland, Maier & Neustadt, L.L.P.

(57) ABSTRACT

Provided are gelling agent compositions capable of preparing gel compositions with good stability, which include a composition containing (A) at least one kind of N-acyl acidic amino acid dialkylamide represented by the formula (I):

$$R^3 \underset{H}{\overset{O}{\underset{\|}{C}}} N \underset{CONHR^2}{\overset{(CH_2)_n-CONHR^1}{<}} \quad (I)$$

wherein each symbol is as described in the DESCRIPTION) and (B) fatty acid having 3-22 carbon atoms or fatty acid having 3-22 carbon atoms and higher alcohol having 8-22 carbon atoms or (E) N-acylamino acid, a composition containing (A) at least one kind of N-acyl acidic amino acid dialkylamide represented by the formula (I) and (B') a solvent having a boiling point of not more than 120° C. and not more than 2 wt % of water, and a composition containing a particular N-acyl acidic amino acid dialkylamide at a particular ratio.

8 Claims, No Drawings

(56) References Cited

U.S. PATENT DOCUMENTS

| | | |
|---|---|---|
| 2004/0229984 A1 | 11/2004 | Yamato et al. |
| 2005/0100572 A1 | 5/2005 | Hatajima et al. |
| 2005/0208085 A1 | 9/2005 | Yamato et al. |
| 2006/0073177 A1 | 4/2006 | Yamato |
| 2006/0078581 A1 | 4/2006 | Yamato |
| 2007/0237732 A1 | 10/2007 | Yamato et al. |
| 2009/0280076 A1 | 11/2009 | Yoshida et al. |
| 2009/0317345 A1* | 12/2009 | Joshi ................... A61K 8/39 424/65 |
| 2010/0104612 A1 | 4/2010 | Cropper et al. |
| 2012/0045493 A1 | 2/2012 | Popoff et al. |
| 2012/0264742 A1 | 10/2012 | Furuishi et al. |
| 2013/0004442 A1 | 1/2013 | Bui et al. |
| 2013/0005832 A1 | 1/2013 | Bui et al. |
| 2014/0341960 A1 | 11/2014 | Hattori et al. |
| 2016/0000676 A1 | 1/2016 | Kuramoto et al. |
| 2016/0263010 A1 | 9/2016 | Abdo et al. |
| 2017/0088699 A1 | 3/2017 | Iwakuni et al. |
| 2017/0209355 A1 | 7/2017 | Tezuka et al. |
| 2017/0281495 A1 | 10/2017 | Haraya et al. |

FOREIGN PATENT DOCUMENTS

| | | |
|---|---|---|
| JP | 1-172312 A | 7/1989 |
| JP | 02-088513 | 3/1990 |
| JP | 2001-342254 | 12/2001 |
| JP | 2003-149691 A | 5/2003 |
| JP | 2003-213162 A | 7/2003 |
| JP | 2004-143292 A | 5/2004 |
| JP | 2004-315515 A | 11/2004 |
| JP | 2005-163029 | 6/2005 |
| JP | 2005-298388 A | 10/2005 |
| JP | 2005-298635 A | 10/2005 |
| JP | 2006-104108 A | 4/2006 |
| JP | 4174994 B2 | 11/2008 |
| JP | 2009-114161 A | 5/2009 |
| JP | 2012-506845 | 3/2012 |
| JP | 2013-40110 A | 2/2013 |
| JP | 2014-74101 A | 4/2014 |
| JP | WO2014/142266 A1 | 9/2014 |
| JP | WO2015/053292 A1 | 4/2015 |
| JP | 2016-34923 A | 3/2016 |
| JP | 2017-43755 | 3/2017 |
| JP | 2017-66199 A | 4/2017 |
| JP | 2017-132861 A | 8/2017 |
| JP | 2017-214314 A | 12/2017 |
| WO | WO 03/102104 A1 | 12/2003 |
| WO | WO 2010/132410 A2 | 11/2010 |
| WO | WO 2011/112799 A2 | 9/2011 |
| WO | WO 2013/118921 A1 | 8/2013 |
| WO | WO 2016/039771 A1 | 3/2016 |
| WO | WO 2016/052072 A1 | 4/2016 |
| WO | WO 2016/104696 | 6/2016 |
| WO | WO2018/003973 | 1/2018 |

OTHER PUBLICATIONS

Yamashita, T., "Technology and Application of Amino Acid-Based Oil Gelling Agent", Ajinomoto Co., Ltd. Chemical Division, vol. 45, No. 5, 1992, pp. 52 and 57-61 (with cover page and English translation).

Oshimura, E. "Application of Amino-Acid Based Oil Gelling Agent to Cosmetics", Fragrance Journal, 2014, pp. 74-80 (with English translation).

Saito, K. et al., "Property and Application of Novel Amino Acid-Based Oil Gelling Agent to Cosmetic", Fragrance Journal, 2007, 10 pages (with English translation).

Extended European Search Report dated Jun. 8, 2020 in corresponding European Patent Application No. 17863747.6, 12 pages.

European Office Action in Application No. 17863747.6 dated May 17, 2021.

* cited by examiner

GEL COMPOSITION

CROSS REFERENCES TO RELATED APPLICATIONS

This application is a continuation of International Patent Application No. PCT/JP2017/038414, filed on Oct. 24, 2017, and claims priority to Japanese Patent Application No. 2016-208184, filed on Oct. 24, 2016, Japanese Patent m Application No. 2017-061620, filed on Mar. 27, 2017, Japanese Patent Application No. 2016-208183, filed on Oct. 24, 2016, and Japanese Patent Application No. 2017-028516, filed on Feb. 17, 2017, all of which are incorporated herein by reference in their entireties.

BACKGROUND OF THE INVENTION

Field of the Invention

The present invention relates to a composition containing N-acyl acidic amino acid dialkylamide and a production method thereof.

Discussion of the Background

Molecules of amino acid derivatives having three or more amide bonds such as dibutyl N-lauroyl-L-glutamide and dibutyl N-2-ethylhexanoyl glutamide are capable of gelling oils and are used for shape stabilization and texture improvement of solid cosmetics and liquid cosmetics. When gelling an oil by using an amino acid-based gelling agent having many amide bonds, it is necessary to first uniformly dissolve these molecules in oil. However, it is known that heating at very high temperature is necessary to uniformly dissolve these gelling agents in oil and the handling in manufacturing is difficult (patent document 1).

To produce a gel composition having a certain degree of strength, it is necessary to add a gelling agent at not less than a certain concentration to oil. When the concentration of the gelling agent in the oil is higher, the temperature of heating necessary to dissolve the gelling agent becomes higher.

For example, the dissolution temperature of dibutyl N-2-ethylhexanoyl glutamide in general oils such as liquid paraffin is as high as 150° C. (when 1 wt % of gelling agent is dissolved) –180° C. (when 2 wt % of gelling agent is dissolved). Uniform mixing in an oily base requires dissolution by heating at a very high temperature condition of not less than 150° C. When dibutyl N-2-ethylhexanoyl glutamide is added to an oily cosmetic base, therefore, other ingredients are problematically degraded or inactivated or evaporated by the influence of heat.

To solve this problem, attempts have been made to gelate oil or an oil-containing formulation by previously dissolving a gelling agent in a solvent superior in dissolving gelling agents and adding this solution into the oil. As a solvent for dissolving a gelling agent, higher alcohols, for example, isostearyl alcohol, 2-octyldodecanol and oleyl alcohol have been used. In addition, polyol-type solvents, particularly, diol solvent, has also been used (patent documents 2, 3). Even when these solvents are used, the dissolution temperature of the gelling agent is 100° C.-120° C., and a high temperature is necessary.

Incidentally, it has been reported that a dissolution temperature of a gelling agent can be lowered to 70° C.-100° C. by simultaneously utilizing dipropyleneglycol as polyol and octyldodecanol as a higher alcohol (patent document 4, [0073] etc.). However, the total concentration of the gelling agent that can be dissolved in the mixed solvent is small, and not less than 12 wt % of a gelling agent (total amount of gelling agent/total amount of solvent=12 wt %) could not be dissolved (patent document 4, Example 1).

In the case of an amino acid derivative gelling agents, the feature that the redissolution temperature of gelling agent is lower than the dissolution temperature of gelling agent is utilized to produce a solution of a gelling agent and a solvent at a lower temperature, and the technique of gelling oil by using this solution is also known. That is, when a powder of a gelling agent is uniformly dissolved in a solvent by heating, cooled and the obtained mixture of solid is dissolved again by heating, the temperature at which the solid can be dissolved (referred to as redissolution temperature) is lower than the temperature at which the powder of the gelling agent is dissolved, and this technique is utilized. Even utilizing this technique, however, it is known that redissolution of a solid mixture containing a gelling agent at a high dose of not less than 10 wt % and a solvent at a temperature of 70° C. or below is difficult (patent document 4).

Document List

Patent Documents patent document 1: WO2013/118921
patent document 2: WO2011/112799
patent document 3: U.S. Pat. No. 8,999,304
patent document 4: US20090317345

SUMMARY OF THE INVENTION

Problems to be Solved by the Invention

An object of the present invention is to provide a gelling agent composition containing a high concentration of a gelling agent, which is optimum for the production of a highly stable cosmetic and the like under appropriate temperature conditions, and a gel composition using same.

Means of Solving the Problems

In view of the above-mentioned problems, the present inventors have conducted intensive studies and found for the first time that, when a fatty acid having 3-22 carbon atoms is used as a solvent, a high dose of a gelling agent can be dissolved at a temperature considerably lower than that in general solvents, and that when an oil is gelled using a gelling agent dissolved in the solvent, a gel composition with good stability (free of sweating phenomenon) can be produced, which resulted in the completion of the present invention.

That is, the present invention includes the following embodiments.

[1] A composition comprising
(A) at least one kind of N-acyl acidic amino acid dialkylamide represented by the formula (I):

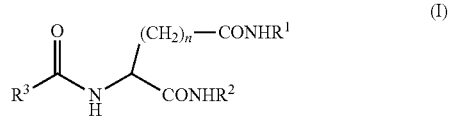

wherein R$^1$ and R$^2$ are each independently a straight chain or branched chain alkyl group having 1-7 carbon atoms, R$^3$ is a straight chain or branched chain alkyl group having 3-15 carbon atoms, and n is 1 or 2), and (B) a fatty acid having 3-22 carbon atoms, or a fatty acid having 3-22 carbon atoms and a higher alcohol having 8-22 carbon atoms.

[2] The composition of [1], wherein N-acyl acidic amino acid dialkylamide represented by the formula (I) is at least one kind selected from the group consisting of dibutyl N-2-ethylhexanoyl glutamide and dibutyl N-lauroyl glutamide.

[3] The composition of [1], wherein N-acyl acidic amino acid dialkylamide represented by the formula (I) is dibutyl N-2-ethylhexanoyl glutamide or dibutyl N-lauroyl glutamide.

[4] The composition of any of [1] to [3], wherein (B) fatty acid is a fatty acid with IOB of not less than 0.3.

[4-1] The composition of [4], wherein (B) fatty acid is at least one selected from the group consisting of lactic acid, capric acid, lauric acid, myristic acid, isostearic acid, 2-hexyldecanoic acid, 2-ethylhexanoic acid and isononanoic acid.

[4-2] The composition of [4], wherein (B) fatty acid is at least one selected from the group consisting of myristic acid and isostearic acid.

[4-3] The composition of any of [1] to [3], wherein (B) higher alcohol is at least one selected from the group consisting of isostearyl alcohol, 2-hexyldecyl alcohol and 2-octyldodecanol.

[5] The composition of any of [1] to [4], comprising 0.8-20 parts by weight of (B) per 1 part by weight of (A).

[5-1] The composition of any of [1] to [4], comprising 0.2-20 parts by weight of (B) per 1 part by weight of (A).

[6] The composition of any of [1] to [6], which is a gelling agent.

[7] The composition of any of [1] to [6], wherein the redissolution temperature is not more than 80° C.

[8] A composition comprising the composition of any of [1] to [7] and (C) an oil agent.

[8-1] The composition of [8], wherein the (C) oil agent is at least one selected from the group consisting of liquid paraffin, cyclopentasiloxane, cetyl ethylhexanoate, cetyl palmitate, almond oil, wheat germ oil, jojoba oil, meadowfoam oil, macadamia nut oil and synthetic wax.

[9] The composition of [8], comprising (A) 0.1-30 wt %, (B) 0.1-80 wt % and (C) 1-99.8 wt %, relative to the total weight of the composition.

[10] The composition of [8] or [9], further comprising (D) an emulsifier.

[10-1] The composition of [10], wherein (D) emulsifier is at least one selected from the group consisting of polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polysorbate 60, sorbeth-30 tetraoleate, glyceryl stearate (SE) and PEG-15 hydrogenated castor oil isostearate.

[11] The composition of [10], comprising (A) 0.1-30 wt %, (B) 0.1-80 wt %, (C) 1-99.7 wt % and (D) 0.1-80 wt % relative to the total weight of the composition.

[11-1] The composition of [10], comprising (A) 0.1-30 wt %, (B) 0.01-80 wt %, (C) 1-99.79 wt % and (D) 0.1-80 wt % relative to the total weight of the composition.

[12] The composition of any of [8] to [11], which is a gel.

[13] The composition of any of [8] to [12], which is used for cosmetic, perfumery, quasi-drug, aromatic, toiletry product, candle or a painting material.

[14] The composition of any of [8] to [13], wherein coloration is suppressed.

[15] The composition of any of [8] to [13], wherein a bitter taste is suppressed.

[16] A method for producing a composition comprising the following (A) and (B), comprising a step of dissolving (A) in (B) at not more than 100° C.:

(A) at least one kind of N-acyl acidic amino acid dialkylamide represented by the formula (I):

$$R^3 \underset{H}{\overset{O}{\underset{\|}{C}}} N - \overset{(CH_2)_n-CONHR^1}{\underset{CONHR^2}{CH}}$$
(I)

wherein R$^1$ and R$^2$ are each independently a straight chain or branched chain alkyl group having 1-7 carbon atoms, R$^3$ is a straight chain or branched chain alkyl group having 3-15 carbon atoms, and n is 1 or 2, (B) a fatty acid having 3-22 carbon atoms, or a fatty acid having 3-22 carbon atoms and a higher alcohol having 8-22 carbon atoms.

[17] The method of [16], wherein the N-acyl acidic amino acid dialkylamide represented by the formula (I) is at least one kind selected from the group consisting of dibutyl N-2-ethylhexanoyl glutamide and dibutyl N-lauroyl glutamide.

[18] The method of [17], wherein the N-acyl acidic amino acid dialkylamide represented by the formula (I) comprises dibutyl N-2-ethylhexanoyl glutamide and dibutyl N-lauroyl glutamide.

[19] The method of any of [16] to [18], wherein (B) is a fatty acid with IOB of not less than 0.3.

[20] The method of any of [16] to [19], wherein 1 part by weight of (A) is dissolved in 0.8-20 parts by weight of (B).

[20-1] The method of any of [16] to [19], wherein 1 part by weight of (A) is dissolved in 0.2-20 parts by weight of (B).

[21] The method of any of [16] to [20], further comprising a step of dissolving, in (C) an oil agent at not more than 100° C., a dissolution product obtained by dissolving (A) in (B).

[22] The method of [21], further comprising a step of adding (D) an emulsifier.

[23] A method for suppressing coloration of a composition containing (A) and (B), comprising a step of dissolving the above-mentioned (A) in (B) at not more than 100° C.

[24] A method for suppressing a bitter taste of a composition containing (A) and (B), comprising a step of dissolving the above-mentioned (A) in (B) at not more than 100° C.

[25] A method for suppressing coloration of a composition containing (A), (B) and (C), comprising a step of dissolving the above-mentioned (A) in (B) at not more than 100° C., and a step of mixing (C) with a dissolution product obtained by dissolving (A) in (B).

[26] A method for suppressing a bitter taste of a composition containing (A), (B) and (C), comprising a step of dissolving the above-mentioned (A) in (B) at not more than 100° C., and a step of mixing (C) with a dissolution product obtained by dissolving (A) in (B).

[27] A composition comprising
(A) at least one kind of N-acyl acidic amino acid dialkylamide represented by the formula (I):

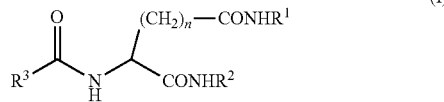

wherein $R^1$ and $R^2$ are each independently a straight chain or branched chain alkyl group having 1-7 carbon atoms, $R^3$ is a m straight chain or branched chain alkyl group having 3-15 carbon atoms, and n is 1 or 2, and (E) N-acylamino acid.
[28] The composition of [27], wherein the N-acyl acidic amino acid dialkylamide represented by the formula (I) is at least one kind selected from the group consisting of dibutyl N-2-ethylhexanoyl glutamide and dibutyl N-lauroyl glutamide.
[29] The composition of [27], wherein the N-acyl acidic amino acid dialkylamide represented by the formula (I) comprises dibutyl N-2-ethylhexanoyl glutamide and dibutyl N-lauroyl glutamide.
[30] The composition of any of [27] to [29], wherein (E) is N-acyl neutral amino acid.
[31] The composition of [30], wherein (E) is at least one selected from the group consisting of N-decanoylproline, N-lauroylsarcosine, N-cocoyl alanine, N-cocoyl valine, N-cocoyl threonine and N-octanoyl-N-methyl-β-alanine.
[32] The composition of any of [27] to [31], wherein 0.2-20 parts by weight of (E) is contained per 1 part by weight of (A).
[33] The composition of any of [27] to [32], which is a gelling agent.
[34] The composition of any of [27] to [33], wherein the redissolution temperature is not more than 80° C.
[35] A composition comprising the composition of any of [27] to [34] and (C) an oil agent.
[36] The composition of [35], wherein the (C) oil agent is at least one selected from the group consisting of liquid paraffin, cyclopentasiloxane, cetyl ethylhexanoate, cetyl palmitate, almond oil, wheat germ oil, jojoba oil, meadowfoam oil, macadamia nut oil and synthetic wax.
[37] The composition of [35] or [36], comprising (A) 0.1-30 wt %, (E) 0.01-80 wt %, and (C) 1-99.89 wt %, relative to the total weight of the composition.
[38] The composition of any of [35] to [37], further comprising (D) an emulsifier.
[39] The composition of [38], wherein (D) emulsifier is at least one selected from the group consisting of polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polysorbate 60, sorbeth-30 tetraoleate, glyceryl stearate (SE) and PEG-15 hydrogenated castor oil isostearate.
[40] The composition of [39], comprising (A) 0.1-30 wt %, (E) 0.01-80 wt %, (C) 1-99.79 wt % and (D) 0.1-80 wt %, relative to the total weight of the composition.
[41] The composition of any of [35] to [40], wherein the composition is a gel.
[42] The composition of any of [35] to [41], wherein the composition is used for cosmetic, perfumery, quasi-drug, aromatic, toiletry product, candle or a painting material.
[43] The composition of any of [27] to [42], wherein coloration is suppressed.
[44] The composition of any of [27] to [42], wherein a bitter taste is suppressed.
[45] A method for producing a composition comprising the following (A) and (E), comprising a step of dissolving (A) in (E) at not more than 100° C.:
(A) at least one kind of N-acyl acidic amino acid dialkylamide represented by the formula (I):

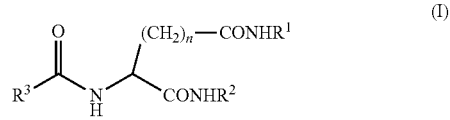

wherein $R^1$ and $R^2$ are each independently a straight chain or branched chain alkyl group having 1-7 carbon atoms, $R^3$ is a straight chain or branched chain alkyl group having 3-15 carbon atoms, and n is 1 or 2, (E) N-acylamino acid.
[46] The method of [45], further comprising a step of dissolving, in (C) an oil agent at not more than 100° C., a dissolution product obtained by dissolving (A) in (E).
[47] The method of [46], further comprising a step of adding (D) an emulsifier.

Effect of the Invention

When the gelling agent composition of the present invention s used for producing cosmetics and perfumery, a conventional treatment at a very high temperature is not necessary, easy production is possible, and production steps of cosmetics and the like can be simplified drastically.

According to the present invention, a highly stable gel composition in which a sweating phenomenon is suppressed can be provided.

According to the present invention, components degraded at a high temperature and components volatilized at a high temperature such as flavor can also be added to cosmetics and the like.

According to the present invention, a composition with an extremely low expression rate of coloration or bitter taste due to degradation of components can be provided.

According to the present invention, a cosmetic with good elongation, and free of stickiness or low viscosity at a high temperature can be provided.

Description of Embodiments

The present invention relates to a composition containing (A) N-acyl acidic amino acid dialkylamide and (B) fatty acid having 3-22 carbon atoms, or fatty acid having 3-22 carbon atoms and higher alcohol having 8-22 carbon atoms (to be referred to as composition I or gelling agent composition) and a composition in which (C) oil agent or (C) and (D) emulsifier is/are added to composition I (to be referred to as composition II or gel composition) and production methods thereof.

Composition I is obtained by combining (A) with poor solubility with (B). It is superior in handling property due to the low redissolution temperature and can reduce degradation of the components.

(A) N-Acyl Acidic Amino Acid Dialkylamide

In the present invention, N-acyl acidic amino acid dialkylamide (A) is represented by the formula (I):

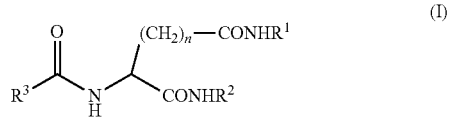

wherein $R^1$ and $R^2$ are each independently a straight chain or branched chain alkyl group having 1-7 carbon atoms. Examples of the straight chain or branched chain alkyl group having 1-7 carbon atoms include methyl group, ethyl group, isopropyl group, propyl group, butyl group, isobutyl group, sec-butyl group, tert-butyl group, pentyl group, sec-pentyl group, tert-pentyl group, isopentyl group, hexyl group, and heptyl group and the like. Since an effective gel strength can be exhibited with a small amount, a straight chain or branched chain alkyl group having 3-5 carbon atoms is preferable, and a butyl group is more preferable. It is more preferable that both $R^1$ and $R^2$ be straight chain or branched chain alkyl groups having 3-5 carbon atoms, and it is further preferable that both $R^1$ and $R^2$ be butyl groups.

In the formula, $R^3$ is a straight chain or branched chain alkyl group having 3-15 carbon atoms. Examples of the straight chain or branched chain alkyl group having 3-15 carbon atoms include propyl group, isopropyl group, butyl group, isobutyl group, sec-butyl group, tert-butyl group, pentyl group, sec-pentyl group, tert-pentyl group, isopentyl group, hexyl group, heptyl group, 1-ethylpentyl group, octyl group, 2-ethylhexyl group, tert-octyl group, nonyl group, isononyl group, decyl group, isodecyl group, undecyl group, dodecyl group, tridecyl group, isotridecyl group, tetradecyl group, and pentadecyl group and the like. Since an effective gel strength can be exhibited with a small amount, a straight chain or branched chain alkyl group having 5-13 carbon atoms is preferable, a straight chain or branched chain alkyl group having 7-11 carbon atoms is more preferable, and a 1-ethyl pentyl group or an undecyl group is most preferable.

n is 1 or 2. When n is 1, (A) is N-acyl aspartic acid dialkylamide, and when n is 2, (A) is N-acyl glutamic acid dialkylamide. Since an effective gel strength can be exhibited with a small amount, n is preferably 2 (N-acylglutamic acid dialkylamide).

Specific examples of the N-acyl acidic amino acid dialkylamide (A) include diisopropyl N-hexanoyl glutamide, dibutyl N-hexanoyl glutamide, di-sec-butyl N-hexanoyl glutamide, diisobutyl N-hexanoyl glutamide, diisopropyl N-octanoyl glutamide, dibutyl N-octanoyl glutamide, di-sec-butyl N-octanoyl glutamide, diisobutyl N-octanoyl glutamide, dimethyl N-2-ethyl hexanoyl glutamide, diethyl N-2-ethylhexanoyl glutamide, dipropyl N-2-ethylhexanoyl glutamide, diisopropyl N-2-ethylhexanoyl glutamide, dibutyl N-2-ethylhexanoyl glutamide, di-sec-butyl N-2-ethylhexanoyl glutamide, diisobutyl N-2-ethylhexanoyl glutamide, dipentyl N-2-ethylhexanoyl glutamide, dihexyl N-2-ethylhexanoyl glutamide, diisopropyl N-decanoyl glutamide, dibutyl N-decanoyl glutamide, di-sec-butyl N-decanoyl glutamide, diisobutyl N-decanoyl glutamide, dimethyl N-lauroyl glutamide, diethyl N-lauroyl glutamide, dipropyl N-lauroyl glutamide, diisopropyl N-lauroyl glutamide, dibutyl N-lauroyl glutamide, di-sec-butyl N-lauroyl glutamide, diisobutyl N-lauroyl glutamide, dipentyl N-lauroyl glutamide, dihexyl N-lauroyl glutamide, diisopropyl N-palmitoyl glutamide, dibutyl N-palmitoyl glutamide, di-sec-butyl N-palmitoyl glutamide, diisobutyl N-palmitoyl glutamide, diisopropyl N-myristoyl glutamide, dibutyl N-myristoyl glutamide, di-sec-butyl N-myristoyl glutamide, diisobutyl N-myristoyl glutamide, diisopropyl N-2-ethylhexanoyl aspartamide, dibutyl N-2-ethylhexanoyl aspartamide, di-sec-butyl N-2-ethylhexanoyl aspartamide, diisobutyl N-2-ethylhexanoyl aspartamide, diisopropyl N-lauroyl aspartamide, dibutyl N-lauroyl aspartamide, di-sec-butyl N-lauroyl aspartamide, and diisobutyl N-lauroyl aspartamide, preferably, diisopropyl N-2-ethylhexanoyl glutamide, dibutyl N-2-ethylhexanoyl glutamide, di-sec-butyl N-2-ethylhexanoyl glutamide, diisobutyl N-2-ethylhexanoyl glutamide, diisopropyl N-lauroyl glutamide, dibutyl N-lauroyl glutamide, di-sec-butyl N-lauroyl glutamide and diisobutyl N-lauroyl glutamide. More preferred are dibutyl N-2-ethylhexanoyl glutamide and dibutyl N-lauroyl glutamide. As (A), one or more kinds of N-acyl acidic amino acid dialkylamides can also be used.

As (A), dibutyl N-2-ethylhexanoyl glutamide (A1) and dibutyl N-lauroyl glutamide (A2) are preferable. When (A1) and (A2) are used, the weight ratio thereof (A1):(A2) is not particularly limited. It is generally 1:1000-100:1, preferably 1:100-20:1, more preferably 1:10-10:1, further preferably 2:3.

The N-acyl acidic amino acid dialkylamide represented by the formula (I) may be a stereoisomer such as optical isomer, diastereomer and the like, a mixture of any stereoisomers, or racemate.

(B) fatty acid having 3-22 carbon atoms or fatty acid having 3-22 carbon atoms and higher alcohol having 8-22 carbon atoms In the present invention, (B) is fatty acid having 3-22 carbon atom or a mixture of the fatty acid and higher alcohol having 8-22 carbon atoms.

The number of carbon atoms of the fatty acid is generally 3-22, preferably 3-20, particularly preferably 8-18, from the aspects of the stability of formulation, compatibility with an oil agent and lowering of the dissolution temperature of the composition.

In (B) in the present invention, the ratio of the organic value (OV) and inorganic value (IV) (IV/OV=IOB (Inorganic Organic Balance) (hereinafter to be abbreviated as IOB value)), which is an index of the polarity of fatty acid, is generally not less than 0.3.

To lower the dissolution temperature of the composition, IOB value is preferably not less than 0.35, more preferably not less than 0.4. While the upper limit is not particularly limited, it is generally not more than 6, preferably not more than 5.

The IOB value can be calculated from the molecular structure of the compound based on the idea of conceptual diagram (Koda Yoshio et al., "new version conceptual diagram.—foundation and application" new version first printing, Japan, Tokyo, SANKYO SHUPPAN CO., Ltd., October 2008, p. 13-26).

The fatty acid is not particularly limited, and saturated fatty acid and unsaturated fatty acid can be mentioned.

Examples of the saturated fatty acid include straight chain saturated fatty acids such as lactic acid, butanoic acid, pentanoic acid, hexanoic acid (caproic acid), heptanoic acid, octanoic acid (caprylic acid), nonanoic acid, decanoic acid (capric acid), dodecanoic acid (lauric acid), tetradecanoic acid (myristic acid), pentadecanoic acid, hexadecanoic acid (palmitic acid), heptadecanoic acid, octadecanoic acid (stearic acid), icosanoic acid (arachidic acid), henicosyl acid, docosanoic acid (behenic acid); and branched chain saturated fatty acids such as isostearic acid, 2-hexyldecanoic acid, 2-ethylhexanoic acid, isononanoic acid, 12-hydroxystearic acid. Among these, lactic acid, capric acid, lauric acid, myristic acid, isostearic acid, 2-hexyldecanoic acid, 2-ethylhexanoic acid, isononanoic acid and the like are preferable, lactic acid, capric acid, lauric acid, myristic acid, isostearic acid are more preferable, capric acid, myristic acid, isostearic acid, lactic acid are further preferable, myristic acid, isostearic acid are particularly preferable, myristic acid is most preferable.

Examples of the unsaturated fatty acid include 9-hexadecenoic acid (pulmitoleic acid), cis-9-octadecenoic acid (oleic acid), 11-octadecenoic acid (vaccenic acid), cis,cis-9, 12-octadecadienoic acid (linoleic acid), 9,12,15-octadecatrienoic acid ((9,12,15)-linolenic acid), 5,8,11,14-eicosatetraenoic acid (arachidonic acid). Among these, linoleic acid is preferable.

In the present invention, (B) may include a fatty acid having 3-22 carbon atoms and a higher alcohol.

As the higher alcohol for (B), an alcohol having 8-22 carbon atoms can be mentioned and an alcohol having 12-18 carbon atoms is preferable.

Specific examples thereof include lauryl alcohol, myristyl alcohol, 2-octyldodecanol, oleyl alcohol, 2-hexyldecyl alcohol, isostearyl alcohol and the like. Isostearyl alcohol, 2-hexyldecyl alcohol, 2-octyldodecanol and the like are preferable, and 2-hexyldecyl alcohol, 2-octyldodecanol are more preferable.

The content of the higher alcohol is generally 0.1-30 parts by weight, preferably 0.5-25 parts by weight, more preferably 0.5-20 parts by weight, per 1 part by weight of a fatty acid having 3-22 carbon atoms. It is more preferably m not less than 1.5 parts by weight, further preferably not less than 2 parts by weight.

(B) in the composition I of the present invention is preferably a mixture of at least one fatty acid selected from the group consisting of myristic acid and isostearic acid, and at least one higher alcohol selected from the group consisting of isostearyl alcohol, 2-hexyldecyl alcohol and 2-octyldodecanol.

The content of (B) in the composition I of the present invention is generally not more than 20 parts by weight, preferably not more than 10 parts by weight, more preferably not more than 4 parts by weight, and generally not less than 0.8 parts by weight, preferably not less than 1 part by weight, more preferably not less than 1.5 parts by weight, further preferably not less than 2 parts by weight, per 1 part by weight of (A), from the aspects of the stability of composition I and lowering of the dissolution temperature of composition I.

In another embodiment, the content of (B) in the composition I of the present invention is generally not more than 20 parts by weight, preferably not more than 10 parts by weight, more preferably not more than 4 parts by weight, and generally not less than 0.2 parts by weight, preferably not less than 0.5 parts by weight, more preferably not less than 0.8 parts by weight, further preferably not less than 1 part by weight, per 1 part by weight of (A), from the aspects of the stability of composition I and lowering of the dissolution temperature of composition I.

The content of (A) in composition I containing (A) and (B) of the present invention is generally not less than 0.1 wt %, preferably not less than 1 wt %, more preferably not less than 3 wt %, further preferably not less than 20 wt %. It is generally not more than 70 wt %, preferably not more than 40 wt %, more preferably not more than 30 wt %, relative to the total weight of composition I, from the aspects of the dissolution temperature during preparation of composition I and exhibition of sufficient gelling ability when formulated into cosmetics and the like.

The content of (B) in composition I containing (A) and (B) of the present invention is generally not more than 99 wt %, preferably not more than 95 wt %, more preferably not more than 90 wt %, and generally not less than 0.5 wt %, preferably not less than 1 wt %, more preferably not less than 10 wt %, more preferably not less than 20 wt %, relative to the total weight of composition I, from the aspects of the stability of the composition and lowering of the dissolution temperature of the composition.

In another embodiment, the content of (B) in composition I containing (A) and (B) of the present invention is generally not more than 99 wt %, preferably not more than 95 wt %, more preferably not more than 90 wt %, and generally not less than 0.05 wt %, preferably not less than 0.5 wt %, more preferably not less than 1 wt %, further preferably not less than 4 wt %, particularly preferably not less than 10 wt %, most preferably not less than 60 wt %, relative to the total weight of composition I, from the aspects of the stability of the composition and lowering of the dissolution temperature of the composition.

Specific preferable example of composition I is a composition containing (A) (A1):(A2)=2:3 and (B) myristic acid or isostearic acid (unneutralized) in which the content of (A) is not less than 20 wt % and the content of (B) is 10-20 wt %, relative to the total weight of composition I.

Specific another preferable example of composition I is a composition containing (A) (A1):(A2)=2:3 and (B) a mixture of at least one fatty acid selected from myristic acid and isostearic acid (unneutralized) and at least one higher alcohol selected from isostearyl alcohol, 2-hexyldecyl alcohol and 2-octyldodecanol in which the content of (A) is not less than 20 wt % and the content of (B) is 10-20 wt % of fatty acid and not less than 50 wt % for higher alcohol, relative to the total weight of composition I.

In the present invention, (A) is uniformly dissolved in (B) at generally not more than 100° C., preferably not more than 95° C., more preferably not more than 90° C.

Examples of the form (shape) of composition I containing (A) and (B) of the present invention include liquid, powder, solid, gel and cream. Among these, powder, solid, gel or liquid is preferable, more preferably solid or gel.

In the present specification, the temperature at which composition I as solid or gel is heated again to give a uniform solution is indicated as "redissolution temperature".

The redissolution temperature of composition I containing (A) and (B) of the present invention is not more than 100° C., preferably not more than 80° C., more preferably not more than 70° C., further preferably less than 70° C., particularly preferably not more than 65° C., most preferably not more than 60° C. The lower limit is not particularly set as long as dissolution is available, and it is generally not less than 20° C.

The composition I of the present invention may contain other additives as long as the above-mentioned (A) and (B) are contained and the effect of the present invention is not impaired.

Composition II obtained by mixing the above-mentioned composition I with (C) oil agent or (C) and (D) emulsifier is also one embodiment of the present invention.

(C) Oil Agent (C) in the present invention can be used without particularly restriction as long as it is an oil agent other than fatty acid and higher alcohol and generally used for cosmetic, pharmaceutical products and the like. Examples thereof include liquid oil agent, semisolid oil agent, solid oil agent and the like, with preference given to a liquid oil agent.

Specifically, liquid oil agent such as straight chain or branched hydrocarbon oil such as liquid paraffin, light isoparaffin, liquid isoparaffin, hydrogenated polyisobutene, squalane, squalene and the like; vegetable oils such as shea butter, almond oil, jojoba oil, olive oil, jojoba seed oil, maize germ oil, wheat germ oil, meadowfoam oil, sunflower oil, macadamia nut oil and the like; animal-derived fats and oils such as liquid lanolin and the like; ester oils such as fatty acid ester, polyhydric alcohol fatty acid ester (e.g., isopropyl myristate, cetyl ethylhexanoate, ethylhexyl palmitate, cetyl palmitate, isopropyl palmitate, tri(caprylic acid/capric acid) glyceryl, triisostearin, triethylhexanoin and the like); acylamino acid esters such as isopropyl lauroyl sarcosine (Eldew (registered trade mark) SL-205), N-lauroyl-L-glutamic acid di(cholesteryl/octyldodecyl), hexyldecyl myristoyl methyl aminopropionate, dihexyldecyl lauroyl glutamate, diisostearyl lauroyl glutamate, dioctyldodecyl lauroyl glutamate, lauroyl glutamic acid bis(hexyldecyl/octyldodecyl), dioctyldodecyl lauroyl glutamate, dioctyldodecyl stearoyl glutamate and the like; phytosterol esters such as N-lauroyl-L-glutamic acid di(phytosteryl/2-octyldodecyl) and the like; silicone oil such as cyclopentasiloxane, dimethylpolysiloxane, dimethylcyclopolysiloxane, methylphenylpolysiloxane, methyl m hydrogen polysiloxane, higher alcohol denatured organopolysiloxane, bisphenylpropyldimethicone and the like, silicone oil of fluorine oil such as fluoropolyether, perfluoro alkylethersilicone and the like, and the like;

semisolid oil agent such as cholesteryl esters such as cholestryl isostearate, cholestryl hydroxystearate, macadamia nut oil fatty acid cholesteryl, N-lauroyl-L-glutamic acid di(cholesteryl/behenyl/octyldodecyl) and the like; phytosterol esters such as N-lauroyl-L-glutamic acid di(phytosteryl/behenyl/2-octyldodecyl), myristoyl methyl-β-alanine (phytosteryl/decyltetradecyl)isostearic acid phytosteryl, phytosteryl oleate and the like; dipentaerythrityl fatty acid esters such as dipentaerythrityl hexaoxystearate, dipentaerythrityl rosinate and the like; triglycerides such as tri(caprylic acid/capric acid)glyceryl, tri(capuryl/capric/myristic/stearic acid)glycerides and the like; partially hydrogenated triglycerides such as hydrogenated oil and the like; lanolin, lanosterols, petrolatum and the like;

solid oil agents such as animal-derived wax, plant-derived wax, mineral wax, synthetic wax, specifically, rice bran wax, carnauba wax, candelilla wax, beeswax, spermaceti, ceresin, solid paraffin, microcrystalline wax, polyethylene wax, polyolefinwax and the like.

Among these, from the aspect of broad utility, hydrocarbon oils such as petrolatum, solid paraffin, liquid paraffin, hydrogenated polyisobutene and the like; fatty acid ester oils such as cetyl ethylhexanoate, cetyl palmitate, ethylhexyl palmitate, isopropyl myristate, isopropyl palmitate, tri(caprylic acid/capric acid) glycerides, triethylhexanoin, triisostearin and the like; vegetable oil such as rhea butter, almond oil, wheat germ oil, jojoba seed oil, jojoba oil, olive oil, meadowfoam oil, macadamia nut oil and the like; silicone oil such as cyclopentasiloxane, bisphenylpropyldimethicone and the like; phytosterol esters such as N-lauroyl-L-glutamic acid di(phytosteryl/2-octyldodecyl) and the like, acylamino acid ester oil such as isopropyl lauroyl sarcosine and the like, synthetic wax and the like are preferable, liquid paraffin, cyclopentasiloxane, cetyl ethylhexanoate, cetyl palmitate, almond oil, wheat germ oil, jojoba oil, meadowfoam oil, macadamia nut oil, synthetic wax and the like are more preferable, and liquid paraffin, cetyl ethylhexanoate, wheat germ oil and the like are further preferable.

The content of (C) in the composition II of the present invention is generally not less than 1 wt %, preferably not less than 5 wt %, more preferably 6 wt %, further preferably not less than 10 wt %, furthermore preferably not less than 20 wt %, particularly preferably not less than 40 wt %, most preferably not less than 50 wt %, the upper limit is generally not more than 99.9 wt %, preferably not more than 95 wt %, more preferably not more than 90 wt %, further preferably not more than 85 wt %, relative to the total weight of composition II, since a stable composition with good texture and less sweating can be obtained.

To obtain stable composition II with low dissolution temperature and less sweating, the composition containing (A), (B) and (C) contains (A) 0.1-30 wt %, (B) 0.1-80 wt % and (C) 1-99.8 wt %, preferably contains (A) 0.2-15 wt %, (B) 0.2-40 wt % and (C) 5-95 wt %, more preferably contains (A) 0.5-10 wt %, (B) 0.5-20 wt % and (C) 6-90 wt %, relative to the total weight of composition II.

In another embodiment, to obtain stable composition II with low dissolution temperature and less sweating, the composition containing (A), (B) and (C) contains (A) 0.1-30 wt %, (B) 0.01-80 wt % and (C) 1-99.89 wt %, preferably contains (A) 0.2-15 wt %, (B) 0.02-40 wt % and (C) 5-95 wt %, more preferably contains (A) 0.5-10 wt %, (B) 0.05-20 wt % and (C) 6-90 wt %, relative to the total weight of composition II.

In composition II of the present invention, the stability is improved and compatibility of oil can be enhanced by adding (D) emulsifier in addition to the above-mentioned (A)-(C).

(D) Emulsifier

The emulsifier in the present invention is not particularly limited as long as it is used for cosmetics, pharmaceutical products and the like, and nonionic emulsifiers can be mentioned.

Among the nonionic emulsifiers, nonionic emulsifiers generally having HLB 5-16 or HLB 5-17 are used from the aspect of compatibility with oil. Among those, emulsifiers having HLB 8-17 are preferable, emulsifiers having HLB 8-16 are more preferable, emulsifiers having HLB 10-16 are further preferable to reduce sweating of formulation and improve stability. Also, emulsifiers having HLB 5-8 are preferably used in view of the compatibility with oil.

It is also possible to use a mixture of a nonionic surfactant having a low HLB and a surfactant having a high HLB.

Examples of the emulsifier with HLB 10-16 include sorbeth-60 tetraoleate (tetraoleic acid polyoxyethylene(60) sorbit), PEG(polyethylene glycol)-8 glyceryl isostearate, PEG(polyethylene glycol)-7 glyceryl cocoate, polyglyceryl-10 dioleate, polyglyceryl-10 diisostearate, polyglyceryl-10 trilaurate, hexaglyceryl tricaprylate, polyglyceryl-10 cocoate, polyglyceryl-3 cocoate, PEG(polyethylene glycol)-40 glyceryl triisostearate, PEG(polyethylene glycol)-40 glyceryl isostearate, PEG(polyethylene glycol)-50 hydrogenated castor oil isostearate, polysorbate 60, sorbeth-30 tetraoleate, glyceryl stearate (SE: self-emulsifying type). Examples of the emulsifier with HLB 17 include PEG (polyethylene glycol)-100 stearate.

Examples of the emulsifier with HLB 5—less than 10 include polyglyceryl-2 stearate, polyglyceryl-2 oleate, polyglyceryl-2 sesquicaprylate, PEG(polyethylene glycol)-20 glyceryl triisostearate, PEG(polyethylene glycol)-15 hydrogenated castor oil isostearate, PEG(polyethylene glycol)-6 sorbitan oleate.

Among these, polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polyglyceryl-2 oleate, polysorbate 60, sorbeth-30 tetraoleate, glyceryl stearate (SE), PEG-15 hydrogenated castor oil isostearate is preferable, polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polysorbate 60, sorbeth-30 tetraoleate, glyceryl stearate (SE), PEG-15 hydrogenated castor oil isostearate are more preferable.

The content of (D) in the composition II of the present invention is generally not less than 0.1 wt %, preferably not less than 5 wt %, more preferably 12 wt %, further preferably not less than 15 wt %, and the upper limit is generally not more than 80 wt %, preferably not more than 50 wt %, more preferably not more than 40 wt %, further preferably not more than 30 wt %, relative to total weight composition II, from the aspects of the stability of the composition (effect of eliminating sweating) and improved compatibility with oil.

From the aspects of the stability and cleansing function of composition II, the composition containing (A), (B), (C) and (D) generally contains (A) 0.1-30 wt %, (B) 0.1-80 wt %, (C) 1-99.7 wt % and (D) 0.1-80 wt %, preferably contains (A) 0.2-15 wt %, (B) 0.2-40 wt %, (C) 2-95 wt % and (D) 1-68 wt %, more preferably contains (A) 0.5-10 wt %, (B) 0.5-20 wt %, (C) 5-90 wt % and (D) 5-50 wt %, relative to the total weight of composition II.

In another embodiment, the composition containing (A), (B), (C) and (D) generally contains (A) 0.1-30 wt %, (B) 0.01-80 wt %, (C) 1-99.79 wt % and (D) 0.1-80 wt %, preferably contains (A) 0.2-15 wt %, (B) 0.02-40 wt %, (C) 2-95 wt %, and (D) 1-68 wt %, more preferably contains (A) 0.5-10 wt %, (B) 0.05-20 wt %, (C) 5-90 wt % and (D) 5-50 wt %, relative to the total weight of composition II, from the aspects of the stability and cleansing function of composition II.

While the form (shape) of the composition II of the present invention is not particularly limited, it is, for example, gel, liquid, particle, solid, stick, sphere, sheet or the like. Among these, gel, solid or sphere is preferable.

The pH at the time of dissolution of the composition of the present invention is generally more than pH 2 and less than 10, preferably not less than 3, more preferably not less than 4, further preferably not more than 8, more preferably not more than 7.5.

The temperature at which composition II containing components (A)-(D) of the present invention is uniformly dissolved is generally not more than 100° C., preferably not more than 90° C., more preferably not more than 80° C. Therefore, when used for producing cosmetics and perfumery, a conventional treatment at a very high temperature is not necessary, cosmetic and the like can be produced easily, and production steps of cosmetics and the like can be simplified drastically.

In the present invention, the constitutions of composition I and composition II can suppress coloration of the composition observed during preservation or immediately after production. Coloration is expressed due to degradation of components. In the case of composition I, coloration derived from degradation of (B) is observed and, in the case of composition II, coloration derived from degradation of (B), (C), (D), perfume, polyhydric alcohol, surfactant other than (D) and the like is observed.

In the present invention, the constitutions of composition I and composition II can suppress a bitter taste of the compositions. The bitter taste of composition in the case of composition I is, for example, a bitter taste derived from (A) and the bitter taste in the case of composition II is, for example, a bitter taste derived from (A) and (C).

The composition of the present invention can also contain components generally used for cosmetic agents such as various chelating agents, antiperspirant active ingredient, surfactants other than nonionic emulsifiers, various additives, various powders, gelling agent other than A and the like within the range where the effect of the present invention is not inhibited.

While various chelating agents are not particularly limited, preferable examples include a chelator selected from the group consisting of triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, 8-hydroxyquinoline-5-sulfonic acid, glycine, 2,2'-pyridylethylenediamine, aurintricarboxylic acid, xylenol orange, 5-sulfosalicyl acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N, N,N',N'-tetraacetic acid, acetylacetone, and salts thereof and a mixture thereof and the like.

Examples of the antiperspirant active ingredient include one kind selected from the group consisting of aluminum chlorohydrate, aluminum chloride, aluminum chlorohydrate allantoinate, aluminum sulfate, zinc oxide, zinc para-phenolsulfonate, and zirconium aluminum complex produced by reacting zirconylchloride with aluminum hydroxide and aluminumchlorohydroxide, and a mixture thereof. As used herein, the antiperspirant active ingredient refers to a component that suppresses sweating by causing strong adstriction of the skin.

Examples of the surfactant other than nonionic emulsifier include anionic surfactant such as N-long chain fatty acid acyl-N-methyltaurine salt, alkylsulfate and alkyleneoxide adduct thereof, fatty acid amide ether sulfate, metal salt or weak base salt of fatty acid, sulfosuccinic acid-based surfactant, alkyl phosphate and alkyleneoxide adduct thereof, alkylethercarboxylic acid, and the like; cationic surfactant such as aliphatic amine salt (alkyl ammonium chloride, dialkyl ammonium chloride and the like), aromatic quaternary ammonium salt (quaternary ammonium salt thereof, benzalkonium salt thereof and the like), fatty acid acyl arginine ester, and the like; and amphoteric surfactant (betaine type surfactant (carboxybetaine and the like), aminocarboxylic acid type surfactant, imidazoline type surfactant and the like, and the like.

Examples of the various additives include amino acids such as glycine, alanine, serine, threonine, arginine, glutamic acid, aspartic acid, isoleucine, leucine, valine and the like; water-soluble polymer such as pyrrolidonecarboxylic acid and sodium or zinc salt thereof, polyglutamic acid, polyamino acid including polyaspartic acid and a salt thereof, gum arabics, alginates, xanthan gum, hyaluronic acid, hyaluronic acid salt, chitin, chitosan, water-soluble chitin, carboxyvinyl polymer, carboxymethylcellulose, hydroxyethylcellulose, hydroxypropyltrimethylammonium chloride, polychlorodimethylmethylenepiperidium, polyvinylpyrrolidone derivative, quaternary ammonium cationized protein, collagen decomposed product and a derivative thereof, acylated protein and the like; sugar alcohol such as mannitol and the like and alkylene oxide adduct thereof; animals and plants extract, nucleic acid, vitamin, enzyme, anti-inflammatory agent, antimicrobial agent, preservative, antioxidant, ultraviolet absorber, adiaphoretic, pigment, dye, oxidation dye, pH adjuster, pearly agent, wetting agent, polyhydric alcohol such as 1,3-butyleneglycol and the like, and the like.

Examples of the various powders include resin powder such as nylon beads, silicone beads and the like, nylon powder, metal fatty acid soap, yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, titanium oxide fine particles, zinc oxide fine particles, iron oxide fine particles and the like can be mentioned, which may be further subjected to a surface treatment such as silicone treatment, fluorine compound treatment, silane coupling agent treatment, silane treatment organic titanate treatment, acylation lysine treatment, fatty acid treatment, metal soap treatment, oil treatment, amino acid treatment and the like.

The gelling agent other than (A) is not particularly limited as long as it is a gelling agent other than (A) of the present invention. For example, a gelling agent composed of a dextrin derivative, a gelling agent composed of a high molecular polymer having a plurality of amide bonds or a derivative thereof can be mentioned. Examples of the gelling agent composed of a dextrin derivative include (palmitic acid/hexyldecanoic acid)dextrin, dextrin palmitate, palmitic acid/ethylhexyl acid)dextrin, dextrin myristate, inulin stearate. Examples of the gelling agent composed of a high molecular polymer or a derivative thereof include polyamide-3, polyamide-8, polyamide-5 and the like.

The composition I of the present invention can be used as a base of cosmetic, perfumery, pharmaceutical product, quasi-drug and the like, a texture modifier, a thickener, a stabilizer or a gelling agent. The base refers to a component among the materials of cosmetic and the like, which is mainly used for giving a shape to a product and also called an excipient.

Furthermore, the composition II of the present invention can be used as it is, or after blending with the aforementioned components, as cosmetic, perfumery, quasi-drug, aromatic, toiletry product, candle or painting material.

The shape of cosmetic, perfumery, pharmaceutical product or quasi-drug containing the composition II of the present invention is not particularly limited. For example, paste, gel, cream, particle, solid, stick, sphere, sheet can be mentioned. Among these, paste, gel, solid, sphere are preferable, paste, gel are more preferable, and the dissolution state thereof may be transparent or opaque.

Specific examples of the cosmetic, perfumery and quasi-drug include solid preparations such as adiaphoretic, chapstick, lip rouge, sun protectant, solid foundation, concealer, foundation primer, cleansing agent and the like, gel or gel dispersions or emulsions such as facial cleanser, cleansing gel, milky lotion, massage cream, cold cream, moisture gel, facial mask, after shaving gel, milky liquid foundation, blush, mascara, shampoo, rinse, hair-growth drug, treatment, conditioner, tic, set lotion, hair cream, hair wax, hair mousse, permanent wave solution, hair dye, hair coloring, hair manicure, sunscreen oil, hand soap, mouthwash and the like, aromatic, cataplasm and the like. Preferred are adiaphoretic, lip rouge, chapstick, cream, milky lotion and sun protectant, and more preferred are adiaphoretic, lip rouge, cream, milky lotion and sun protectant.

Specific examples of the pharmaceutical product include external preparations such as ointment, cream, gel and the like, adhesive preparation, suppository and the like.

Cosmetic, perfumery, pharmaceutical product and quasi-drug containing the composition II of the present invention can be produced according to a conventional method.

The present invention includes a composition containing (A) N-acyl acidic amino acid dialkylamide and (E) N-acylamino acid (to be referred to as composition III or gelling agent composition) and a composition containing composition III and (C) oil agent or (C) and (D) emulsifier (to be referred to as composition IV or gel composition), and production methods thereof. The N-acylamino acid in the present invention is preferably an unneutralized form.

Composition III is obtained by combining (A) with poor solubility and (E). It is superior in handling property due to the low redissolution temperature and can reduce degradation of the components.

As the acyl group of N-acylamino acid, a straight chain or branched chain acyl group induced from a saturated or unsaturated fatty acid having 8-22 carbon atoms can be used. Specific examples of the acyl group include octanoyl group, nonanoyl group, decanoyl group, undecanoyl group, lauroyl group, myristoyl group, palmitoyl group, stearoyl group, oleoyl group, linoleyl group, acyl group induced from mixed fatty acid derived from nature (e.g., coconut oil fatty acid, castor oil fatty acid, olive oil fatty acid, palm oil fatty acid) and the like. Preferred is an acyl group induced from octanoyl group, decanoyl group, lauroyl group or coconut oil fatty acid.

While the amino acid of N-acylamino acid is not particularly limited, neutral amino acid is preferable, and glycine, alanine, N-methyl-β-alanine, threonine, sarcosine, β-alanine, phenylalanine, proline, valine, leucine, isoleucine, serine, hydroxyproline, aminobutyric acid, aminocaproic acid and the like can be mentioned. These amino acids may be any of L form, D form and DL form. One kind of these may be used, or a mixture of two or more kinds selected from the above-mentioned group may be used. Among these, proline, alanine, valine, threonine, sarcosine, N-methyl-β-alanine are preferable.

Amino acid having an asymmetric carbon atom may be an optically active form or a racemate.

Specific examples of N-acylamino acid include N-decanoylproline, N-lauroylsarcosine, N-cocoyl alanine, N-cocoyl valine, N-cocoyl threonine, N-octanoyl-N-methyl-β-alanine.

Component (E) N-acylamino acid used in the present invention can be obtained, for example, by a known method. To be specific, it can be obtained by Schotten-Baumann reaction between neutral amino acid and fatty acid halide and the like.

The content of (E) in the composition III of the present invention is generally not more than 20 parts by weight, preferably not more than 10 parts by weight, more preferably not more than 4 parts by weight, and generally not less than 0.2 parts by weight, preferably not less than 0.5 parts by weight, more preferably not less than 0.8 parts by weight, further preferably not less than 1 part by weight, per 1 part by weight of (A), from the aspects of the stability of composition III and lowering of the dissolution temperature of composition III.

The content of (A) in the composition III containing (A) and (E) of the present invention is generally not less than 0.1 wt %, preferably not less than 1 wt %, more preferably not less than 3 wt %, relative to the total weight composition III, from the aspects of the dissolution temperature during preparation of composition I and exhibition of sufficient gelling ability when formulated into cosmetics and the like. It is generally not more than 70 wt %, preferably not more than 40 wt %, more preferably not more than 30 wt %.

The content of (E) in the composition III containing (A) and (E) of the present invention is generally not more than 99 wt %, preferably not more than 95 wt %, more preferably not more than 90 wt %, relative to the total weight composition III, from the aspects of the stability of the composition and lowering of the dissolution temperature of the composition. It is generally not less than 0.05 wt %, preferably not less than 0.5 wt %, more preferably not less than 1 wt %, further preferably not less than 4 wt %.

In the present invention, (A) is uniformly dissolved in (E) at generally not more than 100° C., preferably not more than 95° C., more preferably not more than 90° C.

The form (shape) of composition III containing (A) and (E) of the present invention is, for example, liquid, powder, solid, gel, cream or the like. Among these, powder, solid, gel or liquid is preferable, solid or gel is more preferable.

In the present specification, the temperature at which composition III as a solid or gel is heated again to give a uniform solution is referred to as "redissolution temperature".

The redissolution temperature of composition III containing (A) and (E) of the present invention is not more than 100° C., preferably not more than 80° C., more preferably not more than 70° C., further preferably less than 70° C., particularly preferably not more than 65° C., most preferably not more than 60° C. The lower limit is not particularly set as long as composition III can be dissolved and it is generally not less than 20° C.

The composition III of the present invention may contain other additives as long as the above-mentioned (A) and (E) are contained and the effect of the present invention is not impaired.

Composition IV obtained by mixing the above-mentioned composition III with the above-mentioned (C) oil agent or (C) and (D) emulsifier is also one embodiment of the present invention.

The content of (C) in the composition IV of the present invention is generally not less than 1 wt %, preferably not less than 5 wt %, more preferably 6 wt %, further preferably not less than 10 wt %, furthermore preferably not less than 20 wt %, particularly preferably not less than 40 wt %, most preferably not less than 50 wt %, the upper limit is generally not more than 99.9 wt %, preferably not more than 95 wt %, more preferably not more than 90 wt %, further preferably not more than 85 wt %, relative to the total weight of composition IV, since a stable composition with good texture and less sweating can be obtained.

To obtain stable composition IV with low dissolution temperature and less sweating, the composition containing (A), (E) and (C) contains (A) 0.1-30 wt %, (E) 0.01-80 wt % and (C) 1-99.89 wt %, preferably contains (A) 0.2-15 wt %, (E) 0.02-40 wt % and (C) 5-95 wt %, more preferably contains (A) 0.5-10 wt %, (E) 0.05-20 wt % and (C) 6-90 wt %, relative to the total weight of composition IV.

In composition IV of the present invention, the stability is improved and compatibility of oil can be enhanced by adding (D) emulsifier in addition to the above-mentioned (A), (E) and (C).

The content of (D) in the composition IV of the present invention is generally not less than 0.1 wt %, preferably not less than 5 wt %, more preferably 12 wt %, further preferably not less than 15 wt %, and the upper limit is generally not more than 80 wt %, preferably not more than 50 wt %, more preferably not more than 40 wt %, further preferably not more than 30 wt %, relative to total weight composition IV, from the aspects of the stability of the composition (effect of eliminating sweating) and improved compatibility with oil.

The composition containing (A), (E), (C) and (D) generally contains (A) 0.1-30 wt %, (E) 0.01-80 wt %, (C) 1-99.79 wt % and (D) 0.1-80 wt %, preferably contains (A) 0.2-15 wt %, (E) 0.02-40 wt %, (C) 2-95 wt % and (D) 1-68 wt %, more preferably contains (A) 0.5-10 wt %, (E) 0.05-20 wt %, (C) 5-90 wt % and (D) 5-50 wt %, relative to the total weight of composition IV, from the aspects of the stability and cleansing function of composition IV.

While the form (shape) of the composition IV of the present invention is not particularly limited, it is, for example, gel, liquid, particle, solid, stick, sphere, sheet or the like. Among these, gel, solid or sphere is preferable.

The pH at the time of dissolution of the compositions III and IV of the present invention is generally more than pH 2 and less than 10, preferably not less than 3, more preferably not less than 4, further preferably not more than 8, more preferably not more than 7.5.

The temperature at which composition IV containing components (A), (E), (C) and (D) of the present invention is uniformly dissolved is generally not more than 100° C., preferably not more than 90° C., more preferably not more than 80° C. Therefore, when used for producing cosmetics and perfumery, a conventional treatment at a very high temperature is not necessary, cosmetic and the like can be produced easily, and production steps of cosmetics and the like can be simplified drastically.

In the present invention, the constitutions of composition III and composition IV can suppress coloration of the composition observed during preservation or immediately after production. Coloration is expressed due to degradation of components. In the case of composition III, coloration derived from degradation of (B) is observed and, in the case of composition IV, coloration derived from degradation of (E), (C), (D), perfume, polyhydric alcohol, surfactant other than (D) and the like is observed.

In the present invention, the constitutions of composition III and composition IV can suppress a bitter taste of the compositions. The bitter taste of composition in the case of composition III is, for example, a bitter taste derived from (A) and the bitter taste in the case of composition IV is, for example, a bitter taste derived from (A) and (C).

The compositions III and IV of the present invention can also contain components generally used for cosmetic agents described in the above-mentioned compositions I and II within the range where the effect of the present invention is not inhibited.

The composition III of the present invention can be used as a base of cosmetic, perfumery, pharmaceutical product, quasi-drug and the like, a texture modifier, a thickener, a stabilizer or a gelling agent. The base refers to a component among the materials of cosmetic and the like, which is mainly used for giving a shape to a product and also called an excipient.

Furthermore, the composition IV of the present invention can be used as it is, or after blending with the aforementioned components, as cosmetic, perfumery, quasi-drug, aromatic, toiletry product, candle or painting material.

The shape of cosmetic, perfumery, pharmaceutical product or quasi-drug containing the composition IV of the present invention is not particularly limited. For example, paste, gel, cream, particle, solid, stick, sphere, sheet can be mentioned. Among these, paste, gel, solid, sphere are preferable, paste, gel are more preferable, and the dissolution state thereof may be transparent or opaque.

Specific examples of the cosmetic, perfumery and quasi-drug are the same as those recited for the above-mentioned composition I.

Cosmetic, perfumery, pharmaceutical product and quasi-drug containing the composition IV of the present invention can be produced according to a conventional method.

The present invention also includes a method for producing a composition comprising (A) and (B), comprising a step of dissolving (A) in (B) at not more than 100° C. (production method of composition I).

Generally, 1 past by weight of (A) is dissolved in not more than 20 parts by weight, preferably not more than 10, parts by weight, more preferably not more than 4 parts by weight, and generally not less than 0.8 parts by weight, preferably not less than 1 part by weight, more preferably not less than 2 parts by weight, of (B).

The dissolution temperature is generally not more than 100° C., preferably not more than 98° C., more preferably not more than 95° C., further preferably not more than 90° C. The lower limit is generally not less than 20° C., preferably not less than 40° C.

The time necessary for dissolution is the time necessary for becoming uniform. It is generally 10-120 min, preferably 20-90 min, more preferably 30-60 min. Agitation is applied as necessary. A step for cooling the obtained uniformly dissolved solution may also be included.

The obtained composition I can be used as a gelling agent. The redissolution temperature of the composition I is not more than 100° C., preferably not more than 80° C., more preferably not more than 70° C., further preferably less than 70° C., particularly preferably not more than 65° C., most preferably not more than 60° C. The lower limit is generally not less than 20° C. The definition and the like of each component are as described above.

The present invention further includes a method for producing a composition containing (A)-(C), including steps of the following (1) and (2) (production method of composition II):

(1) a step of dissolving (A) in (B) at not more than 100° C.
(2) a step of mixing with (dissolving in) (C) a dissolution product (composition I as solid, gel or liquid) obtained by dissolving (A) in (B) at not more than 100° C.

This method may include, after the above-mentioned step (1), a step of redissolving, at not more than 80° C. after cooling, the dissolution product obtained by dissolving (A) in (B) (composition I).

In (2), the total amount of the dissolution product of (A) and (B) is generally 0.1-70 wt %, preferably 1-50 wt %, more preferably 5-40 wt %, relative to the total weight of (A), (B) and (C).

In (2), the temperature of mixing (dissolving) is generally not more than 100° C., preferably not more than 90° C., more preferably not more than 80° C. The lower limit is generally not less than 20° C., preferably not less than 30° C., more preferably not less than 40° C.

The mixing (dissolving) is performed by, for example, heating the mixture using an oil bath or a heater.

The time necessary for mixing (dissolving) in (2) is the time necessary for becoming uniform. It is generally 10-120 min, preferably 20-60 min, more preferably 30-40 min. Agitation is applied as necessary, and when the solution becomes uniform, it is cooled to give a composition.

The obtained composition can be used as a gelling agent. The definition and the like of each component are as described above.

The above-mentioned production method may further include (3) a step of adding (D).

The amount of (D) is generally 0.1-80 wt %, preferably 1-68 wt %, more preferably 5-50 wt %, relative to the total weight of composition containing (A)-(D).

The timing of addition of (D) may be before or after the above-mentioned (2). (D) may be added to (C), or (D) may be added to the dissolution product obtained in (2). A step of adding (D) to (C) is preferable.

In (3), the temperature of mixing (dissolving) is generally not more than 100° C., preferably not more than 90° C., more preferably not more than 80° C. The lower limit is generally not less than 20° C., preferably not less than 30° C., more preferably not less than 40° C.

The time necessary for mixing (dissolving) in (3) is the time necessary for becoming uniform. It is generally 10-120 min, preferably 20-60 min, more preferably 30-40 min.

Agitation is applied as necessary, and when the solution becomes uniform, it is cooled to give a composition. The definition and the like of each component are as described above.

The present invention also includes a method for suppressing coloration of a composition containing (A) and (B), comprising a step of dissolving (A) in (B) at not more than 100° C. (method for suppressing coloration of composition I).

The present invention also includes a method for suppressing a bitter taste of a composition containing (A) and (B), comprising a step of dissolving (A) in (B) at not more than 100° C. (method for suppressing bitter taste of composition I).

The definition and the like of each component and conditions are as described above.

The present invention also includes a method for suppressing coloration of a composition containing (A)-(C), comprising a step of mixing (dissolving) (A) in (B) at not more than 100° C., and a step of mixing (C) with a dissolution product obtained by dissolving (A) in (B) (method for suppressing coloration of composition II).

The present invention also includes a method for suppressing a bitter taste of a composition containing (A)-(C), comprising a step of mixing (dissolving) (A) in (B) at not more than 100° C., and a step of mixing (C) with a dissolution product obtained by dissolving (A) in (B) (method for suppressing bitter taste of composition II).

The definition and the like of each component and conditions are as described above.

The present invention also includes a method for producing a composition comprising (A) and (E), comprising a step of dissolving (A) in (E) at not more than 100° C. (production method of composition III).

Generally, 1 part by weight of (A) is dissolved in not more than 20 parts by weight, preferably not more than 10 parts by weight, more preferably not more than 4 parts by weight, and generally not less than 0.8 parts by weight, preferably not less than 1 part by weight, more preferably not less than 2 parts by weight, of (E).

The dissolution temperature is generally not more than 100° C., preferably not more than 98° C., more preferably not more than 95° C., further preferably not more than 90° C. The lower limit is generally not less than 20° C., preferably not less than 40° C.

The time necessary for dissolution is the time necessary for becoming uniform. It is generally 10-120 min, preferably 20-90 min, more preferably 30-60 min. Agitation is applied as necessary. A step for cooling the obtained uniformly dissolved solution may also be included.

The obtained composition III can be used as a gelling agent. The redissolution temperature of the composition III is not more than 100° C., preferably not more than 80° C., more preferably not more than 70° C., further preferably less than 70° C., particularly preferably not more than 65° C., most preferably not more than 60° C. The lower limit is generally not less than 20° C. The definition and the like of each component are as described above.

The present invention further includes a method for producing a composition containing (A), (E) and (C), including steps of the following (1) and (2) (production method of composition II):
(1) a step of dissolving (A) in (E) at not more than 100° C.
(2) a step of mixing with (dissolving in) (C) a dissolution product (composition I as solid, gel or liquid) obtained by dissolving (A) in (E) at not more than 100° C.

This method may include, after the above-mentioned step (1), a step of redissolving, at not more than 80° C. after cooling, the dissolution product obtained by dissolving (A) in (E) (composition I).

In (2), the total amount of the dissolution product of (A) and (E) is generally 0.1-70 wt %, preferably 1-50 wt %, more preferably 5-40 wt %, relative to the total weight of (A), (E) and (C).

In (2), the temperature of mixing (dissolving) is generally not more than 100° C., preferably not more than 90° C., more preferably not more than 80° C. The lower limit is generally not less than 20° C., preferably not less than 30° C., more preferably not less than 40° C.

The mixing (dissolving) is performed by, for example, heating the mixture using an oil bath or a heater.

The time necessary for mixing (dissolving) in (2) is the time necessary for becoming uniform. It is generally 10-120 min, preferably 20-60 min, more preferably 30-40 min. Agitation is applied as necessary, and when the solution becomes uniform, it is cooled to give a composition.

The obtained composition can be used as a gelling agent. The definition and the like of each component are as described above.

The above-mentioned production method may further include (3) a step of adding (D).

The amount of (D) is generally 0.1-80 wt %, preferably 1-68 wt %, more preferably 5-50 wt %, relative to the total weight of composition containing (A), (E), (C) and (D).

The timing of addition of (D) may be before or after the above-mentioned (2). (D) may be added to (C), or (D) may be added to the dissolution product obtained in (2). A step of adding (D) to (C) is preferable.

In (3), the temperature of mixing (dissolving) is generally not more than 100° C., preferably not more than 90° C., more preferably not more than 80° C. The lower limit is generally not less than 20° C., preferably not less than 30° C., more preferably not less than 40° C.

The time necessary for mixing (dissolving) in (3) is the time necessary for becoming uniform. It is generally 10-120 min, preferably 20-60 min, more preferably 30-40 min. Agitation is applied as necessary, and when the solution becomes uniform, it is cooled to give a composition. The definition and the like of each component are as described above.

The present invention also includes a method for suppressing coloration of a composition containing (A) and (E), comprising a step of dissolving (A) in (E) at not more than 100° C. (method for suppressing coloration of composition III).

The present invention also includes a method for suppressing a bitter taste of a composition containing (A) and (E), comprising a step of dissolving (A) in (E) at not more than 100° C. (method for suppressing bitter taste of composition III).

The definition and the like of each component and conditions are as described above.

The present invention also includes a method for suppressing coloration of a composition containing (A), (E) and (C), comprising a step of mixing (dissolving) (A) in (E) at not more than 100° C., and a step of mixing (C) with a dissolution product obtained by dissolving (A) in (E) (method for suppressing coloration of composition IV).

The present invention also includes a method for suppressing a bitter taste of a composition containing (A), (E) and (C), comprising a step of mixing (dissolving) (A) in (E) at not more than 100° C., and a step of mixing (C) with a dissolution product obtained by dissolving (A) in (E) (method for suppressing bitter taste of composition IV).

The definition and the like of each component and conditions are as described above.

EXAMPLES

While the present invention is explained in further detail by illustrating Examples, the present invention is not limited to the following Examples.
Evaluation of Redissolution Temperature An appropriate amount of component (B) was measured into a glass vial, and an appropriate amount of component (A) was added to component (B). The mixture was heated and stirred in an oil bath to uniformly dissolve component (A) in component (B). The uniformly dissolved solution was cooled by placing at room temperature for not less than 3 hr. The mixture in solid or gel was heated and stirred in an oil bath, and the temperature at which a uniform solution was obtained again was measured by a thermometer and evaluated as a redissolution temperature.

As component (A), an amino acid-based gelling agent "GP-1" manufactured by Ajinomoto Co., Inc. was used as dibutyl N-lauroyl-L-glutamide, an amino acid-based gelling agent "EB-21" manufactured by Ajinomoto Co., Inc. was used as dibutyl N-2-ethylhexanoyl glutamide (hereinafter the same), and prepared at GP-1:EB-21=3:2 (Experimental Example 1).

In Experimental Example 2, they were used at a ratio of GP-1:EB-21=1:3-1:4.

In Experimental Example 1 and Experimental Example 2, a redissolution temperature of 60° C. or lower was evaluated as "A" (very preferable), a redissolution temperature exceeding 60° C. and not higher than 70° C. was evaluated as "B" (preferable) and a redissolution temperature exceeding 70° C. was evaluated as "C" (unpreferable).
Compatibility with Oil Each (2 g) of the various oil agents shown in Table 1 was measured in a separate, transparent glass vial, component (B) as a solvent (1 g) was added to each oil agent, and they were mixed in an oil bath at 60° C. for 1 hr. After standing for one day, the appearance was determined by visual observation.

As the diagnostic criteria of the compatibility of 6 categories of the oil agents in the following Table and solvent, separation from at least three categories of oil agents was evaluated as "D" (not preferable), separation from at least two categories of oil agents was evaluated as "C" (not very preferable), separation from one category of oil agent was evaluated as "B" (preferable), and uniform dissolution of all categories of oil agents was evaluated as "A" (very preferable).

TABLE 1

| category of oil agent (classification) | display name of oil agent |
|---|---|
| non-polar oil agent | liquid paraffin |
| silicone oil agent | cyclopentasiloxane |
| ester oil agent | isopropyl myristate |
| oil agent for cleansing oil | cetyl ethylhexanoate |
| triglyceride oil agent | almond oil |
| | tri(caprylic acid/capric acid)glyceryl |
| amino acid-based oil agent | lauroyl glutamic acid di(phytosteryl/octyldodecyl) |

Experimental Example 1

Mixtures (20 g) of (A) and (B) at proportions (wt %) shown in Tables 2-1, 2-2 and 2-3 were placed in glass vials, and the dissolution temperature and redissolution temperature were measured and evaluated as described above. The compatibility with the oil agent of (B) was evaluated as described above. The results are shown in Tables 2-1 to 2-3.

As component (A), an amino acid-based gelling agent "GP-1" manufactured by Ajinomoto Co., Inc. was used as dibutyl N-lauroyl-L-glutamide, an amino acid-based gelling agent "EB-21" manufactured by Ajinomoto Co., Inc. was used as dibutyl N-2-ethylhexanoyl glutamide (hereinafter the same), and prepared at GP-1:EB-21=3:2.

TABLE 2-1

| | component | Example 1-1 | Example 1-2 | Example 1-3 | Example 1-4 | Example 1-5 | Example 1-6 | Example 1-7 |
|---|---|---|---|---|---|---|---|---|
| A | dibutyl lauroyl glutamide (GP-1) | 12 | 12 | 12 | 12 | 12 | 12 | 12 |
| A | dibutyl ethylhexanoyl glutamide (EB-21) | 8 | 8 | 8 | 8 | 8 | 8 | 8 |
| B | isostearic acid | 80 | — | — | — | — | — | — |
| B | 2-hexyldecanoic acid | — | 80 | — | — | — | — | — |
| B | 2-ethylhexanoic acid | — | — | 80 | — | — | — | — |
| B | isononanoic acid | — | — | — | 80 | — | — | — |
| B | myristic acid | — | — | — | — | 80 | — | — |
| B | lauric acid | — | — | — | — | — | 80 | — |
| B | capric acid | — | — | — | — | — | — | 80 |
| | total (wt %) | 100 | 100 | 100 | 100 | 100 | 100 | 100 |
| | dissolution temperature (° C.) | 90 | 90 | 65 | 70 | 85 | 75 | 70 |
| | redissolution temperature (° C.) | 65 | 63 | 25 | 50 | 60 | 50 | 45 |
| | qualitative evaluation of redissolution temperature | B | B | A | A | A | A | A |
| | compatibility of various oil agents and solvents | A | A | A | A | A | A | A |

TABLE 2-2

| | component | Ex. 1-8 | Ex. 1-9 | Ex. 1-10 | Ex. 1-11 | Ex. 1-12 | Ex. 1-13 | Ex. 1-14 | Ex. 1-15 | Ex. 1-16 | Ex. 1-17 |
|---|---|---|---|---|---|---|---|---|---|---|---|
| A | dibutyl lauroyl glutamide (GP-1) | 12 | 9 | 9 | 9 | 6 | 6 | 6 | 10.2 | 18 | 24 |
| A | dibutyl ethylhexanoyl glutamide (EB-21) | 8 | 6 | 6 | 6 | 4 | 4 | 4 | 6.8 | 12 | 16 |
| B | 2-octyldodecanol | — | — | — | — | 75 | — | — | — | — | — |
| B | 2-hexyldecyl alcohol | — | 35 | — | — | — | — | — | — | — | — |
| B | isostearyl alcohol | — | — | 35 | — | — | 85 | 80 | — | — | — |
| B | isostearic acid | — | 50 | 50 | 85 | — | — | 10 | 83 | — | — |
| B | myristic acid | — | — | — | — | 15 | 5 | — | — | — | — |
| B | capric acid | — | — | — | — | — | — | — | — | 70 | — |
| B | hexanoic acid | 80 | — | — | — | — | — | — | — | — | — |
| B | lactic acid | — | — | — | — | — | — | — | — | — | 60 |
| | total (wt %) | 100 | 100 | 100 | 100 | 100 | 100 | 100 | 100 | 100 | 100 |
| | dissolution temperature (° C.) | 65 | 90 | 90 | 85 | 85 | 80 | 80 | 90 | 90 | 85 |
| | redissolution temperature (° C.) | 45 | 65 | 65 | 60 | 60 | 60 | 60 | 65 | 65 | 65 |

TABLE 2-2-continued

| component | | Ex. 1-8 | Ex. 1-9 | Ex. 1-10 | Ex. 1-11 | Ex. 1-12 | Ex. 1-13 | Ex. 1-14 | Ex. 1-15 | Ex. 1-16 | Ex. 1-17 |
|---|---|---|---|---|---|---|---|---|---|---|---|
| | qualitative evaluation of redissolution temperature | A | B | B | A | A | A | A | B | B | B |
| | compatibility of various oil agents and solvents | A | A | A | A | A | A | A | A | A | C |

TABLE 2-3

| | Comp. Ex. 1-1 | Comp. Ex. 1-2 | Comp. Ex. 1-3 | Comp. Ex. 1-4 | Comp. Ex. 1-5 | Comp. Ex. 1-6 | Comp. Ex. 1-7 | Comp. Ex. 1-8 |
|---|---|---|---|---|---|---|---|---|
| dibutyl lauroyl glutamide (GP-1) | 12 | 12 | 12 | 12 | 12 | 9 | 18 | 24 |
| dibutyl ethylhexanoyl glutamide (EB-21) | 8 | 8 | 8 | 8 | 8 | 6 | 12 | 16 |
| 2-octyldodecanol | 80 | — | — | — | — | 85 | 70 | — |
| oleyl alcohol | — | 80 | — | — | — | — | — | — |
| pentyleneglycol | — | — | — | — | 80 | — | — | — |
| 2-hexyldecyl alcohol | — | — | 80 | — | — | — | — | — |
| isostearyl alcohol | — | — | — | 80 | — | — | — | 60 |
| total (wt %) | 100 | 100 | 100 | 100 | 100 | 100 | 100 | 100 |
| dissolution temperature (° C.) | 125 | 110 | 110 | 110 | 80 | 110 | 150 | 140 |
| redissolution temperature (° C.) | 95 | 85 | 85 | 85 | 65 | 90 | 125 | 120 |
| qualitative evaluation of redissolution temperature | D | D | D | D | B | D | D | D |
| compatibility of various oil agents and solvents | A | A | A | A | D | A | A | A |

As shown in Tables 2-1, 2-2 and 2-3, when fatty acid or fatty acid and higher alcohol were used as the solvent, (A) could be dissolved at not more than 90° C. and it was confirmed that the redissolution temperature was as low as 70° C. or below. On the other hand, the dissolution temperature with higher alcohol alone was as high as 100° C. or above, and the redissolution temperature was also higher than 80° C. When pentylene glycol was mixed with various oil agents, it was separated over time and compatibility with the oil agents was not preferable. Thus, it was found that even though the dissolution temperature of the gelling agent could be lowered by utilizing polyol, since polyol has poor compatibility with non-polar oil agents, it causes phase separation from oil when added to the oil (Comparative Example 1-5).

Experimental Example 2

Mixtures (20 g) of (A) and (B) at proportions (wt %) shown in Table 3 were placed in glass vials, and the dissolution temperature and redissolution temperature were measured and evaluated as described above. In addition, the compatibility with the oil agent of (B) was evaluated as described above. The results are shown in Table 3.

TABLE 3

| component | | Comparative Example 2-1 | Comparative Example 2-2 | Example 2-1 | Example 2-2 | Example 2-3 |
|---|---|---|---|---|---|---|
| A | dibutyl lauroyl glutamide (GP-1) | 5 | 5 | 5 | 3 | 6 |
| A | dibutyl ethylhexanoyl glutamide (EB-21) | 15 | 15 | 15 | 9 | 24 |
| B | lactic acid | — | — | — | — | 70 |
| B | capric acid | — | — | 80 | — | — |
| B | myristic acid | — | — | — | 88 | — |
| B | 2-octyldodecanol | 80 | — | — | — | — |
| B | isostearyl alcohol | — | 80 | — | — | — |
| | total (wt %) | 100 | 100 | 100 | 100 | 100 |
| | dissolution temperature (° C.) | 135 | 120 | 75 | 80 | 80 |
| | redissolution temperature (° C.) | 115 | 100 | 70 | 70 | 70 |
| | qualitative evaluation of redissolution temperature | D | D | B | B | B |
| | compatibility of various oil agents and solvents | A | A | A | A | C |

As shown in Table 3, when fatty acid was used as the solvent, high doses of (A) could be dissolved at not more than 90° C. and it was confirmed that the redissolution temperature was as low as 70° C. or below. On the other hand, the dissolution temperature with higher alcohol alone was as high as 120° C. or above, and the redissolution temperature was also higher than 100° C. or above.

Experimental Example 3

According to the proportions (wt %) shown in Table 4, component (B) was measured into a glass vial such that the total amount of a mixture of (A)-(D) was 20 g. Component (A) was added to component (B), and the mixture was heated and stirred in an oil bath to uniformly dissolve component (A) in component (B). The uniformly dissolved solution was cooled by placing at room temperature for not less than 3 hr. The uniform mixture of (A) and (B) that became solid or gel by cooling was heated and stirred in an oil bath at the redissolution temperature to give a uniform solution again. Component (C) or a mixture of component (C) and component (D) was measured into a separate glass vial and the mixture was uniformly mixed and dissolved. Finally, a mixed solution of (B) and (A) was added to component (C) or a mixed solution of component (C) and component (D) and the mixture was mixed by stirring at 80° C. The thus-obtained various compositions composed of a mixture of (A)-(D) were evaluated according to the following criteria. When mixing was not attainable even by stirring at 80° C., the mixture of (A)-(D) was uniformly mixed by heating at a higher temperature.

Confirmation of Transparency

The uniform solution obtained by heating and stirring was cooled for not less than 3 hr at room temperature (25° C.). The transparency of the mixture in the glass vial was confirmed (25° C.) by visual observation. A transparent solution was evaluated as "A" (preferable) and a cloud gel was evaluated as "B" (unpreferable).

Evaluation of Sweating of Composition

The uniform solution obtained by heating and stirring was cooled for not less than 3 hr at room temperature. The obtained solid or gel mixture was stored in an apparatus, in which the temperature can be continuously changed in a cycle of from −5° C. to 40° C., for the time period of 3 cycles. Thereafter, the gel mixture was taken out from the apparatus and stored in an environment of ordinary temperature and ordinary humidity for 12 hr. The surface of the gel mixture was visually observed (25° C.). A droplet confirmed on the surface was evaluated as "B" (unpreferable) due to sweating, and the absence of confirmation was evaluated as "A" (preferable) without sweating.

Uniform Mixing Temperature of Mixture of (A)-(D) being not More than 80° C.

A mixture of (A)-(D) which was prepared by the method of the above-mentioned Experimental Example 3 and could be uniformly mixed at 80° C. was evaluated as "A" (preferable), and a mixture of (A)-(D) which could not be uniformly mixed at 80° C. and was confirmed to contain granules and solid in the solution was evaluated as "B" (unpreferable).

The results are shown in Tables 4-1 and 4-2.

TABLE 4-1

| component | component | Example 3-1 | Example 3-2 | Example 3-3 | Example 3-4 | Example 3-5 | Example 3-6 | Example 3-7 | Example 3-8 | Example 3-9 | Example 3-10 | Example 3-11 |
|---|---|---|---|---|---|---|---|---|---|---|---|---|
| C | liquid paraffin | 25 | 25 | 25 | 25 | 90 | — | — | 25 | 25 | 25 | 25 |
| C | cetyl ethylhexanoate | 40 | — | 40 | — | — | 90 | — | 40 | — | 40 | — |
| C | wheat germ oil | — | 40 | — | 40 | | — | 90 | — | 40 | — | 40 |
| D | PEG-15 hydrogenated castor oil isostearate (HLB 6) | 25 | 25 | — | — | — | — | — | 25 | 25 | — | — |
| D | polyglyceryl-10 dioleate (HLB 11) | — | — | 25 | 25 | — | — | — | — | — | 25 | 25 |
| A + B | formulation of Examples 1-1 to 1-8 | 10 | 10 | 10 | 10 | 10 | 10 | 10 | — | — | — | — |
| A + B | formulation of Examples 2-1 to 2-2 | — | — | — | — | — | — | — | 10 | 10 | 10 | 10 |
| | total (wt %) | 100 | 100 | 100 | 100 | 100 | 100 | 100 | 100 | 100 | 100 | 100 |
| | confirmation of transparency | A | A | A | A | A | A | A | A | A | A | A |
| | evaluation of sweating of formulation | A | A | A | A | A | A | A | A | A | A | A |
| | uniform mixing temperature of formulation is 80° C. or below | A | A | A | A | A | A | A | A | A | A | A |

TABLE 4-2

| component | component | Comp. Ex. 3-1-1 | Comp. Ex. 3-1-2 | Comp. Ex. 3-1-3 | Comp. Ex. 3-1-4 | Comp. Ex. 3-1-5 | Comp. Ex. 3-1-6 | Comp. Ex. 3-2 | Comp. Ex. 3-3 | Comp. Ex. 3-4 | Comp. Ex. 3-5 | Comp. Ex. 3-6 | Comp. Ex. 3-7 | Comp. Ex. 3-8 |
|---|---|---|---|---|---|---|---|---|---|---|---|---|---|---|
| C | liquid paraffin | 25 | 25 | 25 | 25 | 25 | 25 | 25 | 25 | 25 | 25 | 90 | — | — |
| C | cetyl ethylhexanoate | 40 | 40 | 40 | 40 | 40 | 40 | 40 | — | 40 | — | — | 90 | |
| C | wheat germ oil | — | — | — | — | — | — | — | 40 | — | 40 | — | — | 90 |
| D | PEG-15 hydrogenated castor oil isostearate (HLB 6) | 25 | 25 | 25 | 25 | 25 | 25 | 25 | 25 | — | — | — | — | — |
| D | polyglyceryl-10 dioleate (HLB 11) | — | — | — | — | — | — | — | — | 25 | 25 | — | — | — |
| A + B | formulation of Comparative Example 1-1 | 10 | — | — | — | — | — | — | — | — | — | — | — | — |
| A + B | formulation of Comparative Example 1-2 | — | 10 | — | — | — | — | — | — | — | — | — | — | — |
| A + B | formulation of Comparative Example 1-3 | — | — | 10 | — | — | — | — | — | — | — | — | — | — |
| A + B | formulation of Comparative Example 1-4 | — | — | — | 10 | — | — | — | — | — | — | — | — | — |
| A + B | formulation of Comparative Example 1-5 | | | | | — | — | 10 | 10 | 10 | 10 | 10 | 10 | 10 |
| A + B | formulation of Comparative Example 2-1 | — | — | — | — | 10 | — | — | — | — | — | — | — | — |
| A + B | formulation of Comparative Example 2-2 | — | — | — | — | — | 10 | — | — | — | — | — | — | — |
| | total (wt %) | 100 | 100 | 100 | 100 | 100 | 100 | 100 | 100 | 100 | 100 | 100 | 100 | 100 |
| | confirmation of transparency | A | A | A | A | A | B | B | B | B | B | B | B | B |
| | evaluation of sweating of formulation | A | B | A | A | A | B | B | B | B | B | B | B | B |
| | uniform mixing temperature of formulation is 80° C. or below | B | B | B | B | B | A | A | A | A | A | A | A | A |

As shown in Table 4-1, it was confirmed that the compositions of the Examples could be uniformly mixed at not more than 80° C. and were free of sweating phenomenon, and stable gel compositions were obtained. Since the same results were obtained for all of the A+B compositions of Examples 1-1 to 1-8, the results of eight compositions are shown together in one. The same applies to the results of 2-1 to 2-2.

On the other hand, as shown in Table 4-2, even though the dissolution temperature of the gel compositions could be lowered by utilizing polyol, since polyol has poor compatibility with non-polar oil agents, it causes phase separation from oil when added to the oil. Thus, it was found that the stability of the composition was degraded when polyol was used as a solvent (Comparative Examples 3-2 to 3-8).

Experimental Example 4

The IOB value (inorganic value/organic value) which is an index of the polarity of various solvents was calculated by the existing method (Koda Yoshio et al., "new version conceptual diagram.—foundation and application" new version first printing, Japan, Tokyo, SANKYO SHUPPAN CO., Ltd., October 2008, p. 13-26). The IOB value of each solvent is shown in Table 5.

TABLE 5

| | fatty acids | IOB = inorganic value (I)/organic value (O) |
|---|---|---|
| Example 4-1 | isostearic acid | 0.43 |
| Example 4-2 | myristic acid | 0.54 |
| Example 4-3 | capric acid | 0.75 |
| Example 4-4 | isononanoic acid | 0.94 |
| Example 4-5 | 2-ethylhexanoic acid | 1 |
| Example 4-6 | 12-hydroxystearic acid | 0.69 |
| Example 4-7 | lactic acid | 5 |
| Comparative Example 4-1 | 2-octyldodecanol | 0.26 |
| Comparative Example 4-2 | 2-hexyldecyl alcohol | 0.32 |

Experimental Example 5

Production Method of Formulation (Example 5) Shown in Table 6:

The solid mixture of component group i which was prepared in advance by dissolving uniformly was redissolved by heating at 70° C. The component group ii was separately mixed with heating at 80° C., component group i was added to component group ii, and the mixture was uniformly mixed at 80° C. iii was dissolved in advance, and iii and iv were mixed with heating at 80° C. i+ii was added to iii+iv while stirring by a homomixer (3000 rpm, 80±3° C., 3 min). The mixture was cooled to 30° C. to give a product.

TABLE 6

| | Example 5 | (wt %) |
|---|---|---|
| i | GP-1 | 1.2 |
| | EB-21 | 0.8 |
| | isostearyl alcohol | 6.0 |
| | myristic acid | 5.0 |
| ii | polysorbate 60 | 2.0 |
| | sorbeth-30 tetraoleate | 0.5 |
| | glyceryl stearate (SE) | 0.5 |
| | cetyl palmitate | 3.0 |
| | liquid paraffin | 3.0 |
| | preservative (phenoxyethanol) | 0.3 |
| iii | polyhydric alcohol (1,3-butyleneglycol) | 7.0 |
| | flavor (limonene and linalool) | q.s. |
| iv | water | balance |
| | Total (wt %) | 100 |

Sensory Evaluation

Good spreadability and absence of stickiness of Example 5 were evaluated by six expert panelists according to the following criteria.

<Good Spreadability>

| | |
|---|---|
| 1) spreadability is very good | 4 points |
| 2) spreadability is good | 3 points |
| 3) spreadability is not very good | 2 points |
| 4) spreadability is not good | 1 point |

<Absence of Stickiness>

| | |
|---|---|
| 1) no stickiness | 4 points |
| 2) not sticky | 3 points |
| 3) a little sticky | 2 points |
| 4) very sticky | 1 point |

Based on the average evaluation points by the expert panelists, the following determination was made. The results are shown in Table 7.
(A) very preferable: evaluation average points 3.5 or above
(B) rather preferable: evaluation average points 2.5 points to less than 3.5
(C) not very preferable: evaluation average points 1.5 to less than 2.5
(D) not preferable: evaluation average points less than 1.5

Evaluation of Viscosity Reduction at High Temperature

Final products were heated to 40° C. and decrease in viscosity was determined using a B-type viscometer (Digital Viscometer, manufactured by Tokyo Keiki, rotor No. 4, 30 rpm, 30 sec, 25° C.). When the range of decrease in viscosity was within 10% of the viscosity at room temperature, the reduction in viscosity of the formulation at high temperature was judged to be preferable (A). When the decrease in viscosity was larger than 10%, the reduction in viscosity was judged to be unpreferable (B). The results are shown in Table 7.

TABLE 7

| evaluation item | evaluation |
|---|---|
| good spreadability | A |
| absence of stickiness | A |
| viscosity decrease at high temperature | A |

Experimental Example 6

Evaluation of Degradation of Component

An appropriate amount of component (B) was measured into a glass vial, and an appropriate amount of component (A) was added to component (B). The mixture was heated and stirred in an oil bath to uniformly dissolve component (A) in component (B). The uniformly dissolved solution was cooled by placing at room temperature for not less than 3 hr. Thereafter, each formulation in Table 8 was dissolved at each redissolution temperature and cooled at room temperature for not less than 3 hr. Such redissolution-cooling operation was repeated 5 times. The dissolution temperature and redissolution temperature were measured and shown in Table 8. As dissolved component (A), an amino acid-based gelling agent "GP-1" manufactured by Ajinomoto Co., Inc. was used as dibutyl N-lauroyl-L-glutamide, an amino acid-based gelling agent "EB-21" manufactured by Ajinomoto Co., Inc. was used as dibutyl N-2-ethylhexanoyl glutamide (hereinafter the same), and prepared at GP-1:EB-21=3:2. As for the obtained mixture, six expert panelists visually confirmed coloration of the formulation shown in Table 8 and evaluated according to the following criteria. In addition, about 3 mg of the formulation of Table 8 was put on the tongue and placed in the mouth. The bitterness felt after 30 seconds was evaluated according to the following criteria.

<Absence of Coloration>

| | |
|---|---|
| 1) absence of coloration | 4 points |
| 2) no coloration | 3 points |
| 3) a little coloration | 2 points |
| 4) high coloration | 1 point |

<Absence of Bitter Taste>

| | |
|---|---|
| 1) no bitter taste | 4 points |
| 2) not much bitter taste | 3 points |
| 3) a little bitter taste was felt | 2 points |
| 4) considerable bitter taste was felt | 1 point |

Based on the average evaluation points by the expert panelists, the following determination was made. The results are shown in Table 8.
(A) very preferable: evaluation average points 3.5 or above
(B) rather preferable: evaluation average points 2.5 points to less than 3.5
(C) not very preferable: evaluation average points 1.5 to less than 2.5
(D) not preferable: evaluation average points less than 1.5

TABLE 8

| component | | Example 6-1 | Example 6-2 | Comp. Example 6-1 | Comp. Example 6-2 |
|---|---|---|---|---|---|
| A | dibutyl lauroyl glutamide (GP-1) | 12 | 12 | 12 | 12 |
| A | dibutyl ethylhexanoyl glutamide (EB-21) | 8 | 8 | 8 | 8 |
| B | isostearic acid | 80 | — | — | — |
| B | myristic acid | — | 80 | — | — |
| B | oleyl alcohol | — | — | 80 | — |
| B | 2-octyldodecanol | — | — | — | 80 |
| | total (wt %) | 100 | 100 | 100 | 100 |
| | dissolution temperature (° C.) | 90 | 85 | 110 | 120 |
| | redissolution temperature (° C.) | 65 | 60 | 90 | 100 |
| | evaluation of coloration | A | A | D | A |
| | evaluation of bitter taste | A | A | C | C |

Experimental Example 7

Mixtures (20 g) of (A) and (E) at proportions (wt %) shown in Table 9 were placed in glass vials, and the dissolution temperature and redissolution temperature were measured and evaluated in the same manner as in Experimental Example 1. The compatibility with the oil agent of (E) was evaluated in the same manner as in Experimental Example 1. The results are shown in Table 9.

As component (A), an amino acid-based gelling agent "GP-1" manufactured by Ajinomoto Co., Inc. was used as dibutyl N-lauroyl-L-glutamide, an amino acid-based gelling agent "EB-21" manufactured by Ajinomoto Co., Inc. was used as dibutyl N-2-ethylhexanoyl glutamide (hereinafter the same), and prepared at GP-1:EB-21=3:2.

As shown in Table 9, when acylamino acid was used as the solvent, (A) could be dissolved at not more than 90° C. and it was confirmed that the redissolution temperature was as low as 70° C. or below.

Reference formulation examples using the above-mentioned composition I are shown below. These formulations have high stability, the formulations other than Reference formulation 2 have very high transparency, and can impart very smooth texture when in use. In addition, these formulations can be produced at a temperature not higher than 100° C.

TABLE 9

| component | | Example 1-18 | Example 1-19 | Example 1-20 | Example 1-21 | Example 1-22 | Example 1-23 |
|---|---|---|---|---|---|---|---|
| A | dibutyl lauroyl glutamide (GP-1) | 12 | 12 | 12 | 12 | 12 | 12 |
| A | dibutyl ethylhexanoyl glutamide (EB-21) | 8 | 8 | 8 | 8 | 8 | 8 |
| E | N-decanoylproline | 80 | — | — | — | — | — |
| E | N-lauroylsarcosine | — | 80 | — | — | — | — |
| E | N-cocoyl alanine | — | — | 80 | — | — | — |
| E | N-cocoyl valine | — | — | — | 80 | — | — |
| E | N-cocoyl threonine | — | — | — | — | 80 | — |
| E | N-octanoyl-N-methyl-β-alanine | — | — | — | — | — | 80 |
| | total (wt %) | 100 | 100 | 100 | 100 | 100 | 100 |
| | dissolution temperature (° C.) | 80 | 90 | 90 | 90 | 90 | 75 |
| | redissolution temperature (° C.) | 50 | 70 | 70 | 70 | 60 | 65 |
| | qualitative evaluation of redissolution temperature | ⊙ | ○ | ○ | ○ | ⊙ | ○ |
| | compatibility of various oil agents and solvents | ⊙ | ⊙ | ⊙ | ⊙ | ⊙ | ⊙ |

TABLE 10-1

Reference formulation 1
natural lip formulation:

| | | |
|---|---|---|
| component C | squalane | 63.2 |
| component B | hexyldecanol | 16 |
| component B | myristic acid | 4 |
| component A | dibutyl lauroyl glutamide (GP-1) | 3 |
| component A | dibutyl ethylhexanoyl glutamide (EB-21) | 2 |
| other gelling agent | dextrin palmitate | 1.8 |
| component C | meadowfoam oil | 5 |
| component C | almond oil | 2 |
| component C | macadamia nut oil | 2 |
| component C | jojoba oil | 1 |
| | total (wt %) | 100 |

TABLE 10-2

Reference formulation 2
petrolatum stick formulation:

| | | |
|---|---|---|
| component C | petrolatum | 60 |
| component C | meadowfoam oil | 5 |
| component C | squalane | 2 |
| component B | octyldodecanol | 18 |
| component B | myristic acid | 2 |
| component A | dibutyl lauroyl glutamide (GP-1) | 1.5 |
| component A | dibutyl ethylhexanoyl glutamide (EB-21) | 1 |
| component C | synthetic wax | 2.5 |
| other gelling agent | dextrin palmitate | 2 |
| component C | almond oil | 2 |
| component C | macadamia nut oil | 2 |
| component C | jojoba oil | 1 |
| component C | lauroyl glutamic acid di(phytosteryl/octyldodecyl) | 1 |
| | total (wt %) | 100 |

TABLE 10-3

Reference formulation 3
lip tint formulation:

| | | |
|---|---|---|
| component B | hexyldecanol | 16 |
| component B | myristic acid | 4 |
| component A | dibutyl lauroyl glutamide (GP-1) | 3 |
| component A | dibutyl ethylhexanoyl glutamide (EB-21) | 2 |
| component C | hydrogenated polyisobutene | 50.9 |
| component C | triisostearin | 17 |
| component C | lauroyl glutamic acid di(phytosteryl/octyldodecyl) | 5 |
| component C | cyclopentasiloxane | 2 |
| dye | Red 218 | 0.08 |
| pH adjuster | citric acid | 0.02 |
| | total (wt %) | 100 |

TABLE 10-4

Reference formulation 4
clear lipstick formulation:

| | | |
|---|---|---|
| component B | octyldodecanol | 16 |
| component B | myristic acid | 4 |
| component A | dibutyl lauroyl glutamide (GP-1) | 3 |
| component A | dibutyl ethylhexanoyl glutamide (EB-21) | 2 |

TABLE 10-4-continued

Reference formulation 4
clear lipstick formulation:

| | | |
|---|---|---|
| component C | hydrogenated polyisobutene | 51 |
| component C | triisostearin | 17 |
| component C | lauroyl glutamic acid di(phytosteryl/octyldodecyl) | 5 |
| component C | cyclopentasiloxane | 2 |
| | total (wt %) | 100 |

TABLE 10-5

Reference formulation 5
sun care stick formulation:

| | | |
|---|---|---|
| component C | di(capuryl/capric acid)BG | 23.5 |
| component C | diisostearyl malate | 10 |
| other gelling agent | dextrin palmitate | 3 |
| UV absorber | ethylhexyl methoxycinnamate | 10 |
| UV absorber | bisethylhexyloxyphenolmethoxyphenyltriazine | 6 |
| UV absorber | ethylhexyl salicylate | 5 |
| UV absorber | octocrylene | 5 |
| component C | bisphenylpropyldimethicone | 2 |
| component C | almond oil | 1 |
| component C | meadowfoam oil | 5 |
| component C | macadamia nut oil | 2 |
| component C | squalane | 1 |
| component C | lauroyl glutamic acid di(phytosteryl/octyldodecyl) | 1 |
| component B | hexyldecanol | 16 |
| component B | myristic acid | 4 |
| component A | dibutyl lauroyl glutamide (GP-1) | 3 |
| component A | dibutyl ethylhexanoyl glutamide (EB-21) | 2 |
| | flavor | 0.5 |
| | total (wt %) | 100 |

INDUSTRIAL APPLICABILITY

Using the composition of the present invention, cosmetics and the like with beautiful appearance can be produced easily without damaging the components to be blended in cosmetic, perfumery, quasi-drug and the like.

DESCRIPTION

Title of the Invention: GEL COMPOSITION

TECHNICAL FIELD

The present invention relates to a composition containing N-acyl acidic amino acid dialkylamide, more specifically a gel composition, and a production method thereof.

BACKGROUND ART

Molecules of amino acid derivatives having three or more amide bonds such as dibutyl N-lauroyl-L-glutamide and dibutyl N-2-ethylhexanoyl glutamide are capable of gelling oils and are used for shape stabilization and texture improvement of solid cosmetics and liquid cosmetics. When gelling an oil by using an amino acid-based gelling agent having many amide bonds, it is necessary to first uniformly dissolve these molecules in oil. However, it is known that heating at very high temperature is necessary to uniformly dissolve these gelling agents in oil and the handling in manufacturing is difficult (patent document 1').

To blend a gel having a certain degree of strength, it is necessary to add a gelling agent at not less than a certain concentration to oil. When the concentration of the gelling agent in the oil is higher, the temperature of heating necessary to dissolve the gelling agent becomes higher.

For example, the dissolution temperature of dibutyl N-2-ethylhexanoyl glutamide in general oils such as liquid paraffin is as high as 150° C. (when 1 wt % of gelling agent is dissolved) –180° C. (when 2 wt % of gelling agent is dissolved). Uniform mixing in an oily base requires dissolution by heating at a very high temperature condition of not less than 150° C. When dibutyl N-2-ethylhexanoyl glutamide is added to an oily cosmetic base, therefore, other ingredients are problematically degraded or inactivated or evaporated by the influence of heat.

To solve this problem, attempts have been made to gelate oil or an oil-containing formulation by previously dissolving a gelling agent in a solvent superior in dissolving gelling agents and adding this solution into the oil. As a solvent for dissolving a gelling agent, higher alcohols, for example, isostearyl alcohol, 2-octyldodecanol and oleyl alcohol have been used. In addition, polyol-type solvents, particularly, diol solvent, has also been used (patent documents 2', 3'). Even when these solvents are used, the dissolution temperature of the gelling agent is 100° C.-120° C., and a high temperature is necessary.

Incidentally, it has been reported that a dissolution temperature of a gelling agent can be lowered to 70° C.-100° C. by simultaneously utilizing dipropyleneglycol as polyol and octyldodecanol as a higher alcohol (patent document 4', [0073] etc.). However, with this technique, the total concentration of the gelling agent that can be dissolved in the mixed solvent is small, and not less than 12 wt % of a gelling agent (total amount of gelling agent/total amount of solvent=12 wt %) could not be dissolved (patent document 4', Example 1). When a gelling agent is dissolved by this technique, however, 26-30 wt % of a solvent problematically remains in the formulation as a solvent of the gelling agent (Examples 1 and 2 of patent document 4'). Furthermore, when polyol is used as a solvent, problems also occur such as a decrease in the stability of the formulation and the like.

Further studies have been made to lower the dissolution temperature of the gelling agent by using 3-methoxy-3-methylbutanol which is a lower alcohol (Example 3 of patent document 5'). In this case, however, the concentration of the gelling agent that can be dissolved is limited. That is, only 10 wt % of a gelling agent could be dissolved in 90 wt % of a solvent. Furthermore, 3-methoxy-3-methylbutanol has a boiling point of 174° C. and cannot be removed easily from the formulation.

It is known that lower alcohol such as ethanol is used in emulsion cosmetic which is a cosmetic containing water (patent documents 6', 7'). In patent document 6', however, dissolution of not less than 20 wt % of a gelling agent at not more than 80° C. or uniform dissolution of a formulation at not more than 80° C. was not realized. In patent document 7', not less than 20 wt % of water was contained in the gel composition, the final form was in a liquid form, and a gel composition having high breaking strength was not obtained.

As mentioned above, in the conventional technique, when a powder of a gelling agent is added to a solvent and mixed by heating at 80° C. or below, dissolution of not less than 20 wt % of the gelling agent in the solvent is considered to be difficult. In view of the merit that the concentration of a solvent remaining in the final formulation can be reduced by dissolving a gelling agent at a higher concentration in a solvent, it is desired to dissolve a gelling agent at a high concentration in a solvent. In the production of cosmetic and the like, dissolution of a gelling agent at a temperature of 80° C. or below is a preferable condition. Thus, the development of a technique for dissolving a high concentration of a gelling agent at a lower temperature and blending same has been desired (patent document 4').

Document List

Patent Documents patent document 1': WO2013/118921
patent document 2': WO2011/112799
patent document 3': U.S. Pat. No. 8,999,304
patent document 4': US20090317345
patent document 5': WO2003102104
patent document 6': US20120264742
patent document 7': U.S. Pat. No. 8,591,871

SUMMARY OF THE INVENTION

Problems to be Solved by the Invention

The problem of the present invention is to provide a gelling agent mixture optimal for the production of gel cosmetics and the like by dissolving a high concentration of a gelling agent at a lower temperature.

Means of Solving the Problems

In view of the above-mentioned problems, the present inventors have conducted intensive studies and found for the first time that, when a solvent having a low boiling point (not more than 120° C.) is used, a high dose of a gelling agent can be dissolved at a temperature considerably lower than that in general solvents, and that when an oil is gelled using a gelling agent dissolved in the solvent, a gel formulation (composition) with good stability (free of sweating) can be formed. Surprisingly, moreover, they have found that the gel formulation (composition) after removal of the solvent has extremely high strength, which resulted in the completion of the present invention.

That is, the present invention includes the following embodiments.
[1] A composition comprising
(A') at least one kind of N-acyl acidic amino acid dialkylamide represented by the formula (I):

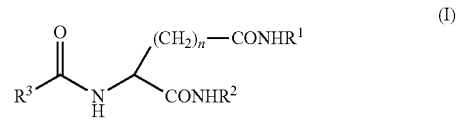

wherein $R^1$ and $R^2$ are each independently a straight chain or branched chain alkyl group having 1-7 carbon atoms, $R^3$ is a straight chain or branched chain alkyl group having 3-15 carbon atoms, and n is 1 or 2), and (B') a solvent having a boiling point of not more than 120° C., and having a water content of not more than 2 wt % relative to the total weight of the composition.
[2] The composition of [1], wherein N-acyl acidic amino acid dialkylamide represented by the formula (I) is at least one kind selected from the group consisting of dibutyl N-2-ethylhexanoyl glutamide and dibutyl N-lauroyl glutamide.

[3] The composition of [1], wherein N-acyl acidic amino acid dialkylamide represented by the formula (I) comprises dibutyl N-2-ethylhexanoyl glutamide and dibutyl N-lauroyl glutamide.

[4] The composition of any of [1]-[3], wherein (B') is a lower alcohol.

[4-1] The composition of [4], wherein (B') is at least one kind of lower alcohol selected from the group consisting of ethanol, 1-propanol, isopropyl alcohol, tert-butyl alcohol, 1-butyl alcohol and 2-butyl alcohol.

[4-2] The composition of [4], wherein (B') is at least one kind of lower alcohol selected from the group consisting of ethanol, isopropyl alcohol and tert-butyl alcohol.

[5] The composition of any of [1] to [4], comprising 0.1-6 parts by weight of (B') per 1 part by weight of (A').

[6] The composition of any of [1] to [5], having a water content of 0.1-1.5 wt % relative to the total weight of the composition.

[6-1] The composition of any of [1] to [5], wherein the composition is a gel.

[6-2] The composition of any of [1] to [5], wherein the composition is a gelling agent.

[7] The composition of any of [1] to [6], wherein the redissolution temperature is not more than 80° C.

[8] A gel composition comprising the composition of any of [1] to [7] and (C') an oil agent.

[8-1] The gel composition of [8], wherein the (C') oil agent is at least one selected from the group consisting of liquid paraffin, cetyl ethylhexanoate, isopropyl myristate, tri(caprylic acid/capric acid)glyceryl, wheat germ oil and shea butter.

[9] The gel composition of [8], comprising (A') 0.1-20 wt %, (B') 0.15-50 wt % and (C') 20-99.7 wt %, relative to the total weight of the gel composition.

[10] The gel composition of [8] or [9], further comprising (D') an emulsifier.

[10-1] The gel composition of [10], wherein (D') emulsifier is at least one selected from the group consisting of polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polysorbate 60, sorbeth-30 tetraoleate, glyceryl stearate (SE) and PEG-15 hydrogenated castor oil isostearate.

[11] The gel composition of [10], comprising (A') 0.1-10 wt %, (B') 0.15-15 wt %, (C') 30-89 wt % and (D') 2-68 wt %, relative to the total weight of the gel composition.

[12] The composition of any of [1] to [11], wherein the composition is used for cosmetic, perfumery or quasi-drug.

[13] A composition comprising the above-mentioned components (A') and (B'), wherein a content of (A') on charging is 10-60 wt % and a content of (B') on charging is 40-90 wt %.

[14] A gel composition comprising the above-mentioned components (A'), (B') and (C'), wherein a content of (A') on charging is 0.5-10 wt % and a content of (B') on charging is 0.5-50 wt %, and a content of (C') on charging is 30-99 wt %.

[15] The gel composition of [14], further comprising the above-mentioned (D'), wherein a content of (C') on charging is 30-95 wt % and a content of (D') on charging is 2-68 wt %.

[16] A method for producing a composition comprising the above-mentioned (A') and (B'), comprising a step of dissolving (A') in (B') at not more than 85° C.

[17] The method of [16], wherein the amount of (A') in the step of dissolving (A') in (B') at not more than 85° C. is 10-60 wt % relative to the total weight of (A') and (B').

[18] The method of [16] or [17], wherein the composition containing (A') and (B') is a gel composition comprising (A'), (B') and (C') an oil agent, the method further comprising a step of dissolving, in (C') the oil agent, a dissolution product obtained by dissolving (A') in (B'), wherein the amount of (A') and (B') in the step is 0.1-60 wt % relative to the total weight of (A'), (B') and (C').

[19] The method of [18], comprising a step of adding 0.1-70 wt % of (D') an emulsifier relative to the total weight of the gel composition.

[20] The method of [18] or [19], comprising a step of removing (B') at not more than 120° C. from the gel composition.

[21] A composition obtained by the production method of any of the above-mentioned [16] to [20].

[22] A gel composition obtained by dissolving dibutyl N-2-ethylhexanoyl glutamide and dibutyl N-lauroyl glutamide in ethanol at not more than 85° C., dissolving the dissolution product in (C') and (D'), and removing ethanol from the obtained dissolution product.

Effect of the Invention

The gel composition of the present invention can be applied to various products since the solvent in the composition can be easily removed as necessary.

By removing the solvent, a gel product having a higher gel strength can be provided.

According to the present invention, a highly stable gel composition in which a sweating (sweating phenomenon) is suppressed can be provided.

According to the present invention, a gel composition capable of blending even components degraded at a high temperature and components volatilized at a high temperature such as flavor to cosmetics and the like can be provided.

When the gel composition of the present invention s used for producing cosmetics and perfumery, a conventional treatment at a very high temperature is not necessary, easy production is possible, and production steps of cosmetics and the like can be simplified drastically.

Description of Embodiments

The present invention relates to a composition comprising containing (A') N-acyl acidic amino acid dialkylamide and (B') a solvent having a boiling point of 120° C. or below, and having a water content of not more than 2 wt %.

(A') N-acyl acidic amino acid dialkylamide

In the present invention, N-acyl acidic amino acid dialkylamide (A') is represented by the formula (I):

$$R^3 \underset{\underset{H}{|}}{\overset{\overset{O}{\|}}{C}} N \overset{(CH_2)_n-CONHR^1}{\underset{CONHR^2}{\diagdown}} \quad (I)$$

wherein $R^1$ and $R^2$ are each independently a straight chain or branched chain alkyl group having 1-7 carbon atoms. Examples of the straight chain or branched chain alkyl group having 1-7 carbon atoms include methyl group, ethyl group, isopropyl group, propyl group, butyl group, isobutyl group, sec-butyl group, tert-butyl group, pentyl group, sec-pentyl group, tert-pentyl group, isopentyl group, hexyl group, and heptyl group and the like. Since an effective gel strength can be exhibited with a small amount, a straight chain or branched chain alkyl group having 3-5 carbon atoms is preferable, and a butyl group is more preferable. It is more preferable that both $R^1$ and $R^2$ be straight chain or branched chain alkyl groups having 3-5 carbon atoms, and it is further preferable that both $R^1$ and $R^2$ be butyl groups.

In the formula, $R^3$ is a straight chain or branched chain alkyl group having 3-15 carbon atoms. Examples of the straight chain or branched chain alkyl group having 3-15 carbon atoms include propyl group, isopropyl group, butyl group, isobutyl group, sec-butyl group, tert-butyl group, pentyl group, sec-pentyl group, tert-pentyl group, isopentyl group, hexyl group, heptyl group, 1-ethylpentyl group, octyl group, 2-ethylhexyl group, tert-octyl group, nonyl group, isononyl group, decyl group, isodecyl group, undecyl group, dodecyl group, tridecyl group, isotridecyl group, tetradecyl group, and pentadecyl group and the like. Since an effective gel strength can be exhibited with a small amount, a straight chain or branched chain alkyl group having 5-13 carbon atoms is preferable, a straight chain or branched chain alkyl group having 7-11 carbon atoms is more preferable, and a 1-ethyl pentyl group or an undecyl group is most preferable.

n is 1 or 2. When n is 1, (A') is N-acyl aspartic acid dialkylamide, and when n is 2, (A') is N-acyl glutamic acid dialkylamide. Since an effective gel strength can be exhibited with a small amount, n is preferably 2 (N-acylglutamic acid dialkylamide).

Specific examples of the N-acyl acidic amino acid dialkylamide (A') include diisopropyl N-hexanoyl glutamide, dibutyl N-hexanoyl glutamide, di-sec-butyl N-hexanoyl glutamide, diisobutyl N-hexanoyl glutamide, diisopropyl N-octanoyl glutamide, dibutyl N-octanoyl glutamide, di-sec-butyl N-octanoyl glutamide, diisobutyl N-octanoyl glutamide, dimethyl N-2-ethyl hexanoyl glutamide, diethyl N-2-ethylhexanoyl glutamide, dipropyl N-2-ethylhexanoyl glutamide, diisopropyl N-2-ethylhexanoyl glutamide, dibutyl N-2-ethylhexanoyl glutamide, di-sec-butyl N-2-ethylhexanoyl glutamide, diisobutyl N-2-ethylhexanoyl glutamide, dipentyl N-2-ethylhexanoyl glutamide, dihexyl N-2-ethylhexanoyl glutamide, diisopropyl N-decanoyl glutamide, dibutyl N-decanoyl glutamide, di-sec-butyl N-decanoyl glutamide, diisobutyl N-decanoyl glutamide, dimethyl N-lauroyl glutamide, diethyl N-lauroyl glutamide, dipropyl N-lauroyl glutamide, diisopropyl N-lauroyl glutamide, dibutyl N-lauroyl glutamide, di-sec-butyl N-lauroyl glutamide, diisobutyl N-lauroyl glutamide, dipentyl N-lauroyl glutamide, dihexyl N-lauroyl glutamide, diisopropyl N-palmitoyl glutamide, dibutyl N-palmitoyl glutamide, di-sec-butyl N-palmitoyl glutamide, diisobutyl N-palmitoyl glutamide, diisopropyl N-myristoyl glutamide, dibutyl N-myristoyl glutamide, di-sec-butyl N-myristoyl glutamide, diisobutyl N-myristoyl glutamide, diisopropyl N-2-ethylhexanoyl aspartamide, dibutyl N-2-ethylhexanoyl aspartamide, di-sec-butyl N-2-ethylhexanoyl aspartamide, diisobutyl N-2-ethylhexanoyl aspartamide, diisopropyl N-lauroyl aspartamide, dibutyl N-lauroyl aspartamide, di-sec-butyl N-lauroyl aspartamide, and diisobutyl N-lauroyl aspartamide, preferably, diisopropyl N-2-ethylhexanoyl glutamide, dibutyl N-2-ethylhexanoyl glutamide, di-sec-butyl N-2-ethylhexanoyl glutamide, diisobutyl N-2-ethylhexanoyl glutamide, diisopropyl N-lauroyl glutamide, dibutyl N-lauroyl glutamide, di-sec-butyl N-lauroyl glutamide and diisobutyl N-lauroyl glutamide. More preferred are dibutyl N-2-ethylhexanoyl glutamide and dibutyl N-lauroyl glutamide.

As (A'), one or more kinds of N-acyl acidic amino acid dialkylamides can also be used.

As (A'), dibutyl N-2-ethylhexanoyl glutamide (A'1) and dibutyl N-lauroyl glutamide (A'2) are preferable. When (A'1) and (A'2) are used, the weight ratio thereof (A'1):(A'2) is not particularly limited. It is generally 1:20-20:1, preferably 1:9-9:1, more preferably 1:4-4:1, further preferably 2:3.

The N-acyl acidic amino acid dialkylamide represented by the formula (I) may be a stereoisomer such as optical isomer, diastereomer and the like, a mixture of any stereoisomers, or racemate.

(B') Solvent Having Boiling Point of not More than 120° C.

(B') in the present invention is an organic solvent having a boiling point of not more than 120° C. at normal pressure. When the boiling point of the solvent is too low, the solvent is difficult to handle in the production step, and a solvent having a low boiling point sometimes lacks preservation stability. Thus, the boiling point is generally not more than 120° C., preferably not more than 100° C., more preferably not more than 85° C., and the lower limit is generally not less than 5° C., preferably not less than 25° C., more preferably not less than 40° C.

(B') in the present invention is not particularly limited as long as it has a boiling point of not more than 120° C., and a solvent generally used for cosmetic, pharmaceutical product and the like is preferable, and alcohol can be mentioned.

As alcohol, lower alcohol is preferable, and monovalent lower alcohol is more preferable.

The lower alcohol is preferably an alcohol having not more than 5 carbon atoms. From the aspects of dissolution property, easy removal of the solvent and the like, an alcohol having not more than 4 carbon atoms is more preferable. Specifically, ethanol (78.4° C.), 1-propanol (97° C.), isopropyl alcohol (2-propanol) (82.4° C.), tert-butyl alcohol (82.4° C.), 1-butyl alcohol (117.4° C.), 2-butyl alcohol (98° C.) and the like can be mentioned, ethanol, isopropyl alcohol, tert-butyl alcohol are preferable, and ethanol is more preferable.

The values in the above-mentioned parentheses show a boiling point of each solvent at normal pressure. These solvents may be used alone or in combination.

The content of (B') in the composition I of the present invention is generally not more than 6 parts by weight, preferably not more than 2 parts by weight, more preferably not more than 0.6 parts by weight, and generally not less than 0.01 parts by weight, preferably not less than 0.05 part by weight, more preferably not less than 0.1 parts by weight, per 1 part by weight of (A'), from the aspects of low dissolution temperature, flame retardancy and stability of the composition.

From the aspects of stability of the composition and low dissolution temperature, the composition containing (A') and (B') generally contains (A') 0.1-60 wt % and (B') 0.1-90 wt %, preferably (A') 1-40 wt % and (B') 0.5-80 wt %, more preferably (A') 1-30 wt % and (B') 0.5-80 wt %, further preferably (A') 5-20 wt % and (B') 1-70 wt %, relative to the total weight of the composition.

For example, when (A') is a gelling agent at (A'1):(A'2)=2:3 and (B') is ethyl alcohol, a composition containing not less than 30 wt % of (A') and 60 wt % of (B') is preferable.

In the present invention, the composition containing (A') and (B') has a water content of generally not more than 2 wt %, preferably 0.1-1.5 wt %, more preferably 0.5-1 wt %, relative to the total weight of the composition.

In the present invention, the composition containing (A') and (B') is uniformly dissolved at generally not more than 85° C., more preferably not more than 80° C.

A gel composition containing a composition containing (A') and (B') and (C') an oil agent (hereinafter sometimes to be abbreviated as the gel composition of the present invention) is also encompassed in the present invention.

(C') Oil agent (C') in the present invention can be used without particularly restriction as long as it is an oil agent used for cosmetic, pharmaceutical products and the like. Examples thereof include liquid oil agent, semisolid oil agent, solid oil agent and the like, with preference given to a liquid oil agent.

Specifically, liquid oil agent such as straight chain or branched hydrocarbon oil such as liquid paraffin, light isoparaffin, liquid isoparaffin, squalane, squalene and the like; vegetable oils such as shea butter, almond oil, jojoba oil, olive oil, jojoba seed oil, maize germ oil, wheat germ oil, meadowfoam oil, sunflower oil and the like; animal-derived fats and oils such as liquid lanolin and the like; ester oils such as fatty acid ester, polyhydric alcohol fatty acid ester (e.g., isopropyl myristate, cetyl ethylhexanoate, ethylhexyl palmitate, cetyl palmitate, isopropyl palmitate, tri(caprylic acid/capric acid)glyceryl, triethylhexanoin and the like); acylamino acid esters such as isopropyl lauroyl sarcosine (Eldew (registered trade mark) SL-205), N-lauroyl-L-glutamic acid di(cholesteryl/octyldodecyl), hexyldecyl myristoyl methyl aminopropionate, dihexyldecyl lauroyl glutamate, diisostearyl lauroyl glutamate, dioctyldodecyl lauroyl glutamate, lauroyl glutamic acid bis(hexyldecyl/octyldodecyl), dioctyldodecyl lauroyl glutamate, dioctyldodecyl stearoyl glutamate and the like; phytosterol esters such as N-lauroyl-L-glutamic acid di(phytosteryl/2-octyldodecyl) and the like; silicone oil such as cyclopentasiloxane, dimethylpolysiloxane, dimethylcyclopolysiloxane, methylphenylpolysiloxane, methyl hydrogen polysiloxane, higher alcohol denatured organopolysiloxane and the like, silicone oil of fluorine oil such as fluoropolyether, perfluoro alkylethersilicone and the like, and the like;

semisolid oil agent such as cholesteryl esters such as cholestryl isostearate, cholestryl hydroxystearate, macadamia nut oil fatty acid cholesteryl, N-lauroyl-L-glutamic acid di(cholesteryl/behenyl/octyldodecyl) and the like; phytosterol esters such as N-lauroyl-L-glutamic acid di(phytosteryl/behenyl/2-octyldodecyl), myristoylmethyl-β-alanine (phytosteryl/decyltetradecyl)isostearic acid phytosteryl, phytosteryl oleate and the like; dipentaerythrityl fatty acid esters such as dipentaerythrityl hexaoxystearate, dipentaerythrityl rosinate and the like; triglycerides such as tri(caprylic acid/capric acid)glyceryl, tri(capuryl/capric/myristic/stearic acid) glycerides and the like; partially hydrogenated triglycerides such as hydrogenated oil and the like; lanolin, lanosterols, petrolatum and the like;

solid oil agents such as animal-derived wax, plant-derived wax, mineral wax, synthetic wax, specifically, rice bran wax, carnauba wax, candelilla wax, beeswax, spermaceti, ceresin, solid paraffin, microcrystalline wax, polyethylene wax, polyolefinwax and the like.

Among these, from the aspect of broad utility, hydrocarbon oils such as petrolatum, solid paraffin, liquid paraffin and the like; silicone oil such as cyclopentasiloxane and the like; fatty acid ester oils such as cetyl ethylhexanoate, ethylhexyl palmitate, isopropyl myristate, isopropyl palmitate, tri(caprylic acid/capric acid)glyceryl, triethylhexanoin and the like; vegetable oils such as shea butter, almond oil, wheat germ oil, jojoba seed oil, olive oil, meadowfoam oil and the like; phytosterol esters such as N-lauroyl-L-glutamic acid di(phytosteryl/2-octyldodecyl) and the like, acylamino acid ester oil such as isopropyl lauroylsarcosine and the like, and the like are preferable, liquid paraffin, cetyl ethylhexanoate, isopropyl myristate, tri(caprylic acid/capric acid) glyceryl, wheat germ oil, shea butter and the like are preferable, and cetyl ethylhexanoate, isopropyl myristate, tri(caprylic acid/capric acid)glyceryl, and wheat germ oil are more preferable.

Among these, fatty acid ester oil such as ethylhexyl palmitate, isopropyl myristate, isopropyl palmitate, tri(caprylic acid/capric acid)glycerides, triethylhexanoin and the like, mineral oil such as liquid paraffin and the like, vegetable oil such as wheat germ oil and the like, shea butter and the like are preferable from the aspects of stability of the composition and a light sense of use.

The content of (C') in the gel composition of the present invention is generally not less than 20 wt %, preferably not less than 30 wt %, more preferably 40 wt %, further preferably not less than 50 wt %, and the upper limit is generally not more than 99.9 wt %, preferably not more than 95 wt %, more preferably not more than 90 wt %, further preferably not more than 85 wt %, relative to the total weight of the gel composition, since a stable gel composition with a low dissolution temperature, a high gel strength and less sweating can be obtained.

The gel composition generally contains (A') 0.1-20 wt %, (B') 0.15-50 wt % and (C') 20-99.7 wt %, preferably (A') 0.5-8 wt %, (B') 0.5-12 wt % and (C') 30-95 wt %, more preferably (A') 1-5 wt %, (B') 0.75-5 wt % and (C') 50-90 wt %, relative to the total weight of the gel composition containing (A')+(B')+(C'), since a stable gel composition with a low dissolution temperature, a high gel strength and less sweating can be obtained.

In the gel composition of the present invention, the stability (no sweating) of the gel composition can be improved by adding (D') emulsifier in addition to the above-mentioned (A')-(C').

(D') Emulsifier (D') in the present invention is not particularly limited as long as it is used for cosmetics, pharmaceutical products and the like, and nonionic emulsifiers can be mentioned.

Among the nonionic emulsifiers, nonionic emulsifiers generally having HLB 5-16 or HLB 5-17 are used from the aspect of compatibility with oil. Among those, from the aspect of less sweating of formulation and improved stability, emulsifiers having HLB 8-17 are preferable, emulsifiers having HLB 8-16 are more preferable, emulsifiers having HLB 10-16 are further preferable.

It is also possible to use a mixture of a nonionic surfactant having a low HLB and a surfactant having a high HLB.

Examples of the emulsifier with HLB 10-16 include sorbeth-60 tetraoleate (tetraoleic acid polyoxyethylene(60) sorbit), PEG-8 glyceryl isostearate, PEG(polyethylene glycol)-7 glyceryl cocoate, polyglyceryl-10 dioleate, polyglyceryl-10 diisostearate, polyglyceryl-10 trilaurate, hexaglyceryl tricaprylate, polyglyceryl-10 cocoate, polyglyceryl-3 cocoate, PEG(polyethylene glycol)-40 glyceryl triisostearate, PEG(polyethylene glycol)-40 glyceryl isostearate, PEG(polyethylene glycol)-50 hydrogenated castor oil isostearate, polysorbate 60, sorbeth-30 tetraoleate, glyceryl stearate (SE: self-emulsifying type). Examples of the emulsifier with HLB 17 include PEG(polyethylene glycol)-100 stearate.

Examples of the emulsifier with HLB 5—less than 10 include polyglyceryl-2 stearate, polyglyceryl-2 oleate, polyglyceryl-2 sesquicaprylate, PEG(polyethylene glycol)-

20 glyceryl triisostearate, PEG(polyethylene glycol)-15 hydrogenated castor oil isostearate, PEG-6 sorbitan oleate.

Among these, polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polyglyceryl-2 oleate, polysorbate 60, sorbeth-30 tetraoleate, glyceryl stearate (SE: self-emulsifying type), PEG-15 hydrogenated castor oil isostearate is preferable, polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polysorbate 60, sorbeth-30 tetraoleate, glyceryl stearate (SE: self-emulsifying type), PEG-15 hydrogenated castor oil isostearate are more preferable, and polyglyceryl-10 dioleate, polyglyceryl-10 cocoate, PEG-40 glyceryl triisostearate and polysorbate 60 are particularly preferable.

The content of (D') in the gel composition of the present invention is generally not less than 2 wt %, preferably not less than 5 wt %, more preferably 10 wt %, further preferably not less than 15 wt %, and the upper limit is generally not more than 80 wt %, preferably not more than 50 wt %, more preferably not more than 40 wt %, further preferably not more than 30 wt %, relative to the total weight of the gel composition, from the aspects of the stability and cleansing function of the composition.

The gel composition generally contains (A') 0.1-10 wt %, (B') 0.15-15 wt %, (C') 30-89 wt % and (D') 2-68 wt %, preferably (A') 0.5-8 wt %, (B') 0.5-12 wt %, (C') 40-87 wt % and (D') 5-50 wt %, more preferably (A') 1-5 wt %, (B') 0.75-5 wt %, (C') 50-80 wt % and (D') 15-30 wt %, relative to the total weight of the gel composition containing (A')+(B')+(C')+(D'), from the aspects of the stability of the composition and removal of dirt on the skin.

In the gel composition of the present invention, (B') may be removed from the gel composition depending on the object of use. (B') can be removed easily by only heating at not more than 120° C., preferably not more than 110° C., more preferably not more than 100° C. For example, to increase gel strength, the content of (B') is preferably 0.01-1 wt %, more preferably 0.05-0.5 wt %, relative to the total weight of the gel composition.

While the form (shape) of the gel composition of the present invention is not particularly limited, it is, for example, particle, solid, stick, sphere, sheet or the like. Among these, solid or sphere is preferable.

The composition and gel composition of the present invention are characteristically produced by blending components (A') and (B'), (A')-(C'), (A')-(D') at the below-mentioned dose at the time of charging. For example, the object gel composition can be obtained by dissolving (A') in (B') at the below-mentioned temperature, adding a part or the total amount of the solution to (C') or (C') and (D') heated in advance at a certain temperature, stirring the mixture with heating until a uniform solution is formed, and thereafter cooling the mixture.

In the composition containing components (A') and (B'), the contents at the time of charging are generally (A') 10-60 wt % and (B') 40-90 wt %, preferably (A') 20-50 wt % and (B') 50-80 wt %, more preferably (A') 30-40 wt % and (B') 60-70 wt %, relative to the total weight of the composition containing (A') and (B').

In the gel composition containing components (A')-(C'), the contents at the time of charging are generally (A') 0.5-10 wt %, (B') 0.5-50 wt % and (C') 30-99 wt %, preferably (A') 1-8 wt %, (B') 1-40 wt % and (C') 40-98 wt %, more preferably (A') 2-5 wt %, (B') 2-25 wt % and (C') 60-96 wt %, relative to the total weight of the composition containing (A')-(C').

In the gel composition containing components (A')-(D'), the contents at the time of charging are generally (A') 0.5-10 wt %, (B') 0.5-49 wt %, (C') 30-95 wt % and (D') 2-68 wt %, preferably (A') 1-8 wt %, (B') 1-40 wt %, (C') 40-90 wt % and (D') 5-50 wt %, more preferably (A') 2-5 wt %, (B') 2-20, (C') 50-80 wt % and (D') 12-30 wt %, relative to the total weight of the composition containing (A')-(D').

The pH at the time of charging of the composition of the present invention is generally more than pH 3 and less than 9, preferably not less than 4, more preferably not less than 5, further preferably not more than 8, more preferably not more than 7.5.

In the present specification, the temperature at which the composition of the present invention as solid or gel is heated again to give a uniform solution is indicated as "redissolution temperature".

The redissolution temperature (melting point) of the composition containing (A') and (B') of the present invention is generally not more than 80° C., preferably not more than 78° C., more preferably not more than 75° C. Therefore, when used for producing cosmetics and perfumery, a conventional treatment at a very high temperature is not necessary, cosmetic and the like can be produced easily, and production steps of cosmetics and the like can be simplified drastically.

In addition, the gel composition of the present invention can also contain components generally usable for cosmetics such as a gelling agent other than (A') of the present invention, various chelating agents, antiperspirant active ingredient, surfactants other than nonionic emulsifiers, various additives, various powders, and the like within the range where the effect of the present invention is not inhibited.

While various chelating agents are not particularly limited, preferable examples include a chelator selected from the group consisting of triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicyl acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone, and salts thereof and a mixture thereof and the like.

Examples of the antiperspirant active ingredient include one kind selected from the group consisting of aluminum chlorohydrate, aluminum chloride, aluminum chlorohydrate allantoinate, aluminum sulfate, zinc oxide, zinc para-phenolsulfonate, and zirconium aluminum complex produced by reacting zirconylchloride with aluminum hydroxide and aluminumchlorohydroxide, and a mixture thereof. As used herein, the antiperspirant active ingredient refers to a component that suppresses sweating by causing strong adstriction of the skin.

Examples of the surfactant other than nonionic emulsifier include anionic surfactant such as N-long chain acylamino acid salts such as N-long chain acylglutamate, N-long chain acylglycine salt, N-long chain acylalanine salt, N-long chain acyl-N-methyl-β-alanine salt and the like, N-long chain fatty acid acyl-N-methyltaurine salt, alkylsulfate and alkyleneoxide adduct thereof, fatty acid amide ether sulfate, metal salt or weak base salt of fatty acid, sulfosuccinic acid-based surfactant, alkyl phosphate and alkyleneoxide adduct thereof, alkylethercarboxylic acid, and the like; non-ionic surfactants such as ether type surfactants such as glycerolether and alkyleneoxide adduct thereof and the like, ether ester type surfactants such as alkylene oxide adduct of glycerolester, alkylene oxide adduct of sorbitan ester, polyoxyalkylene fatty acid ester and the like, ester type surfactants such as glycerol fatty acid ester, fatty acid polyglycerolester, sorbitan fatty acid ester, sucrose fatty acid ester and the like, alkylglucosides such as (caprylyl/capuryl) glucoside and the like, hydrogenated castor oil pyroglutamic acid diester and ethylene oxide adduct thereof, nitrogen-containing type non-ionic surfactants such as fatty acid alkanolamide and the like, and the like; cationic surfactant such as aliphatic amine salt (alkyl ammonium chloride, dialkyl ammonium chloride and the like), aromatic quaternary ammonium salt (quaternary ammonium salt thereof, benzalkonium salt thereof and the like), fatty acid acyl arginine ester, and the like; and amphoteric surfactant such as betaine type surfactant (carboxybetaine and the like), aminocarboxylic acid type surfactant, imidazoline type surfactant and the like, and the like.

Examples of the various additives include amino acids such as glycine, alanine, serine, threonine, arginine, glutamic acid, aspartic acid, isoleucine, leucine, valine and the like; water-soluble polymer such as polyamino acid including polyglutamic acid and polyaspartic acid and a salt thereof, gum arabics, alginates, xanthan gum, chitin, chitosan, water-soluble chitin, carboxyvinyl polymer, carboxymethylcellulose, hydroxyethylcellulose, hydroxypropyltrimethylammonium chloride, polychlorodimethylmethylenepiperidium, polyvinylpyrrolidone derivative, quartenary ammonium cationized protein, collagen decomposed product and a derivative thereof, acylated protein and the like; sugar alcohol such as mannitol and the like and alkylene oxide adduct thereof; animals and plants extract, nucleic acid, vitamin, enzyme, anti-inflammatory agent, antimicrobial agent, preservative, antioxidant, ultraviolet absorber, adiaphoretic, pigment, dye, oxidation dye, pH adjuster, pearly agent, wetting agent and the like, and the like.

Examples of the various powders include resin powder such as nylon beads, silicone beads and the like, nylon powder, metal fatty acid soap, yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, titanium oxide fine particles, zinc oxide fine particles, iron oxide fine particles, acylamino acid such as acyllysine, acylglutamic acid, acylarginine, acylglycine and the like, and the like can be mentioned, which may be further subjected to a surface treatment such as silicone treatment, fluorine compound treatment, silane coupling agent treatment, silane treatment organic titanate treatment, acylation lysine treatment, fatty acid treatment, metal soap treatment, oil treatment, amino acid treatment and the like.

The composition or gel composition of the present invention can be used as it is or as cosmetic, perfumery or quasi-drug after blending the aforementioned components.

The composition or gel composition of the present invention can be used as a base of cosmetic, perfumery, pharmaceutical product, quasi-drug and the like, a texture modifier, a thickener, a stabilizer or a gelling agent. The base refers to a component among the materials of cosmetic and the like, which is mainly used for giving a shape to a product and also called an excipient.

The shape of cosmetic, perfumery, pharmaceutical product or quasi-drug containing the composition II of the present invention is not particularly limited. For example, gel, particle, solid, stick, sphere, sheet can be mentioned. Among these, gel, solid, sphere are preferable, and gel is more preferable.

Specific examples of the cosmetic, perfumery and quasi-drug include solid preparations such as adiaphoretic, chapstick, lip rouge, sun protectant, solid foundation, concealer, foundation primer, cleansing agent and the like, gel or gel dispersions or emulsions such as facial cleanser, cleansing gel, massage cream, cold cream, moisture gel, facial mask, after shaving gel, milky liquid foundation, blush, mascara, shampoo, rinse, hair-growth drug, treatment, conditioner, tic, set lotion, hair cream, hair wax, hair mousse, permanent wave solution, hair dye, hair coloring, hair manicure, sunscreen oil, hand soap and the like, aromatic, cataplasm and the like.

Preferred are adiaphoretic, lip rouge, chapstick, and sun protectant, and more preferred are adiaphoretic, lip rouge, sun protectant, cleansing agent, massage cream, hair coloring agent, and hair wax.

In another embodiment, it is preferably adiaphoretic, lip rouge, chapstick, sun protectant, cleansing agent, massage cream, hair coloring agent or hair wax, and adiaphoretic, lip rouge, sun protectant, cleansing agent, massage cream, hair coloring agent or hair wax is more preferable.

Specific examples of the pharmaceutical product include external preparations such as ointment, cream, gel and the like, adhesive preparation, suppository and the like.

Cosmetic, perfumery, pharmaceutical product and quasi-drug containing the composition or gel composition of the present invention can be produced according to a conventional method.

The present invention also includes a method for producing a composition containing (A') and (B'), comprising a step of dissolving (A') in (B') at not more than 85° C. As described for the above-mentioned compositions, the water content of the composition containing (A') and (B') is not more than 2 wt %.

Generally, the amount of (A') in the step is 10-60 wt %, preferably 20-50 wt %, more preferably 30-40 wt %, relative to the total weight of (A') and (B').

The dissolution temperature is generally not more than 85° C., preferably not more than 83° C., more preferably not more than 80° C. The lower limit is generally not less than 20° C., preferably not less than 40° C.

The dissolving is performed by, for example, heating the mixture using an oil bath or a heater.

The time necessary for dissolution is the time necessary for becoming uniform. It is generally 10-120 min, preferably 20-90 min, more preferably 30-60 min. Agitation is applied as necessary. When the mixture becomes uniform, it is cooled to give a gel composition. The definition and the like of each component are as described above.

The above-mentioned production method further contains a step of dissolving the obtained dissolution product of (A') and (B') in (C') at not more than 85° C.

In the production method of the gel composition containing (A'), (B') and (C') oil agent, which further contains a step of dissolving, in (C') oil agent, a dissolution product obtained by dissolving (A') in (B'), generally, the amounts of (A') and (B') is 0.1-60 wt %, preferably 5-55 wt %, more preferably 10-50 wt %, further preferably 12-45 wt %, relative to the total weight of (A'), (B') and (C').

The dissolution temperature is generally not more than 85° C., more preferably not more than 80° C. The lower limit is generally not less than 20° C., preferably not less than 35° C., more preferably not less than 40° C.

The time necessary for dissolution is the time necessary for becoming uniform. It is generally 10-120 min, preferably 20-60 min, more preferably 30-40 min. Agitation is applied as necessary. When the mixture becomes uniform, it is cooled to give a gel composition. The definition and the like of each component are as described above.

The above-mentioned production method may further include a step of adding (D').

Generally, (D') is added to the gel composition at 0.1-70 wt %, preferably 2-50 wt %, more preferably 5-30 wt %, particularly preferably 12-25 wt %, based on the total weight of the gel composition containing (A') (D').

As the timing of addition of (D'), it may be added to (C') before or after dissolving (A') and (B'). That is, the obtained composition prepared with (A') and (B') may be dissolved in a mixture of (C') added with (D'), or (D') may be added after dissolving the composition of (A') and (B') in (C'). It is preferable to dissolve in the mixture of (C') added with (D').

The dissolution temperature is generally not more than 85° C., more preferably not more than 80° C., and the lower limit is generally not less than 20° C., preferably not less than 35° C., more preferably not less than 40° C.

The time necessary for dissolution is the time necessary for becoming uniform. It is generally 10-120 min, preferably 20-60 min, more preferably 30-40 min. Agitation is applied as necessary. When the mixture becomes uniform, it is cooled to give a gel composition. The definition and the like of each component are as described above.

The production method of the present invention may further contain a step of heating the gel composition at not more than 120° C. and removing (B') from the gel composition. The heating temperature is generally not more than 120° C., preferably not more than 120° C., more preferably not more than 100° C., and the lower limit is not less than 80° C., from the aspects of removal rate of the solvent and stability of the starting materials. The heating can be performed by a method known per se.

Removal of (B') means reducing the content of (B') in the gel composition or removing the total amount. It specifically means removing 10-99 wt %, preferably 50-95 wt %, more preferably 80-90 wt %, of the original content of (B'). The content of (B') after removal in the gel composition is 0-5 wt %, preferably 0.01-1 wt %, more preferably 0.05-0.5 wt %.

The time necessary for removal is generally 10-180 min, preferably 20-120 min, more preferably 30-60 min. Agitation is applied as necessary. When the mixture becomes uniform, it is cooled to give a gel composition.

The step of removing (B') may be performed after dissolving (C') or after dissolving (C') and (D'), and removal after dissolving (C') and (D') is preferable.

Particularly, when the weight ratio of content (A') to content (C') {((A')/(C'))×100} is generally 10 or below, preferably not more than 5, more preferably not more than 3, a gel composition with a high strength can be obtained by this step by using a smaller amount of (A').

The definition and the like of each component are as described above.

EXAMPLE

While the present invention is explained in further detail by illustrating Examples, the present invention is not limited to the following Examples.

Experimental Example 1

Mixtures (20 g) of (A') and (B') at proportions (wt %) shown in Table 1 were placed in glass vials, and mixed in an oil bath at a predetermined temperature until they were uniformly dissolved. When the mixture was not dissolved, the temperature was gradually raised with stirring until it was dissolved. The temperature of uniform mixing was measured by a thermometer, and the temperature at which (A') was dissolved in (B') was taken as a dissolution temperature.

Evaluation of Dissolution Temperature

A dissolution temperature of not more than 85° C. was evaluated as "(○) preferable", and a temperature exceeding 85° C. was evaluated as "(x) unpreferable".

Evaluation of Coloration

Various components were placed in transparent glass vials, and mixed in an oil bath at a predetermined temperature until they were uniformly dissolved. White paper was put behind the container and the degree of solution coloration was confirmed by visual observation.

When the solution was transparent or white, it was evaluated as "(○) preferable", and coloration to yellow or brown was evaluated as "(x) unpreferable".

When a component already having a color before heating was blended, coloration of the final blended product was not confirmed and it was rated as (–).

As component (A'), an amino acid-based gelling agent "GP-1" manufactured by Ajinomoto Co., Inc. was used as dibutyl N-lauroyl-L-glutamide, an amino acid-based gelling agent "EB-21" manufactured by Ajinomoto Co., Inc. was used as dibutyl N-2-ethylhexanoyl glutamide (hereinafter the same), and prepared at GP-1:EB-21=3:2.

The results are shown in Table 1A.

TABLE 1A

| component | | Formulation No. | | | | | | | | | | |
| --- | --- | --- | --- | --- | --- | --- | --- | --- | --- | --- | --- | --- |
| | | Comp. Ex. 1-1 | Comp. Ex. 1-2 | Comp. Ex. 1-3 | Ex. 1-1 | Ex. 1-2 | Ex. 1-3 | Ex. 1-4 | Ex. 1-5 | Ex. 1-6 | Ex. 1-7 |
| B' | solvent used | 2-octyl-dodecanol | oleyl glycol | pentylene alcohol | ethanol | ethanol | ethanol | ethanol | ethanol | isopropyl alcohol | tert-butyl alcohol |
| | solvent (wt %) | 80 | 80 | 80 | 80 | 60 | 50 | 45 | 43 | 60 | 70 |
| A' | gelling agent (wt %) | 20 | 20 | 20 | 20 | 40 | 50 | 55 | 57 | 40 | 30 |
| | total (wt %) | 100 | 100 | 100 | 100 | 100 | 100 | 100 | 100 | 100 | 100 |
| | dissolution temperature (° C.) | 120 | 85 | 110 | 55 | 65 | 72 | 78 | 80 | 75 | 75 |
| | evaluation of dissolution temperature | x | x | x | ○ | ○ | ○ | ○ | ○ | ○ | ○ |
| | redissolution temperature (° C.) | 100 | 90 | 90 | 50 | 60 | 68 | 75 | 78 | 70 | 70 |
| | evaluation of coloration | ○ | ○ | x | ○ | ○ | ○ | ○ | ○ | ○ | ○ |

As shown in Table 1A, it was confirmed that the dissolution temperature decreases by dissolving in a lower alcohol such as ethanol and the like.

Experimental Example 2

Mixtures (20 g) of (A') and (B') at proportions shown in Table 2A were placed in glass vials, mixed in an oil bath at a predetermined temperature until they were uniformly dissolved, and evaluated by the same method as in Experimental Example 1. The temperature at which (A') was dissolved in various solvents when the ratio of (A') was changed and the results of coloration are shown in Table 2A.

Evaluation of Sweating

A solid gel was stored in an apparatus, in which the temperature can be continuously changed in a cycle of from −5° C. to 40° C., for the time period of 3 cycles. Thereafter, the sample was taken out from the apparatus and stored in an environment of ordinary temperature and ordinary humidity for 12 hr. A droplet confirmed on the surface by visual observation was judged to mean presence of sweating of the gel composition and evaluated as "x" (unpreferable). A gel composition for which a droplet was hardly confirmed on the gel surface by visual observation even after a similar operation was judged to hardly have sweating, and evaluated as "(○) (preferable)". Furthermore, a gel composition for

TABLE 2A

| component | | Comp. Ex. 1-1-1 | Comp. Ex. 1-2-1 | Comp. Ex. 1-3-1 | Ex. 1-2-1 | Ex. 1-2-2 | Ex. 1-2-3 | Ex. 1-2-4 | Ex. 1-2-5 | Ex. 1-2-6 | Ex. 1-2-7 |
|---|---|---|---|---|---|---|---|---|---|---|---|
| A' | EB-21:GP-1 | 3:1 | 3:1 | 3:1 | 3:1 | 2.5:1 | 2:1 | 1:1 | 4:1 | 7:1 | 11:1 |
| A' | EB-21 | 30 | 30 | 30 | 30 | 28.6 | 26.7 | 20 | 28 | 26.25 | 22 |
| A' | GP-1 | 10 | 10 | 10 | 10 | 11.4 | 13.3 | 20 | 7 | 3.75 | 2 |
| B' | ethanol | | | | 60 | 60 | 60 | 60 | 65 | 70 | 76 |
| B' | 2-octyldodecanol | 60 | — | — | — | — | — | — | — | — | — |
| B' | pentyleneglycol | — | 60 | — | — | — | — | — | — | — | — |
| B' | oleyl alcohol | — | — | 60 | — | — | — | — | — | — | — |
| | total | 100 | 100 | 100 | 100 | 100 | 100 | 100 | 100 | 100 | 100 |
| | dissolution temperature (° C.) | 140 | 105 | 135 | 80 | 78 | 75 | 70 | 80 | 80 | 75 |
| | evaluation of dissolution temperature | x | x | x | ○ | ○ | ○ | ○ | ○ | ○ | ○ |
| | evaluation of coloration | ○ | ○ | x | ○ | ○ | ○ | ○ | ○ | ○ | ○ |

As shown in Table 2A, it was confirmed that the dissolution temperature decreases by dissolving any ratio of (A') in ethanol.

Experimental Example 3

At the proportions (wt %) shown in Table 2A, (A')-(B') were mixed and heated in advance to give uniform solutions. (C')-(D') at proportions (wt %) shown in Table 3 were placed in glass vials, and heated in an oil bath at a predetermined temperature. To the heated mixture was added a uniform mixture of A and B at the proportion shown in Table 3 and the mixture was mixed until it was uniformly dissolved. The amounts of the mixture of (A') and (B'), and (C'), (D') were measured and added such that the total amount of the mixture at the time of charging was 20 g. The dissolution temperature and coloration were evaluated by the same method as in Experimental Example 1.

The uniformly dissolved solution was cooled at room temperature for not less than 3 hr to give a solid or gel mixture. The sample was evaluated as follows.

which a droplet was not confirmed on the gel surface by visual observation even after a similar operation was judged to have no sweating, and evaluated as "(◎) very preferable".

The results are shown in Table 3A.

Measurement of Breaking Strength of Gel

The breaking strength of the gel was measured by FUDOH Rheometer D-series (manufactured by Rheotech Co., Ltd.). A gel composition with a flat surface set in the machine together with the container, and the measurement was performed using an adapter having a diameter of 10 mm under the conditions of an entrance speed of 6 cm/min and a load of 200 g. The breaking strength value was automatically calculated by the machine.

A breaking strength value of less than 160 g/cm² was judged to mean that a strong gel was formed and evaluated as "(○) preferable", not more than 100 g/cm² and less than 160 g/cm² was judged to mean that a gel with a certain strength was formed and evaluated as "(Δ) not very preferable", and less than 100 g/cm² was judged to be (x) unpreferable. In the Table, (−) means that evaluation was not performed.

The results are shown in Table 3A.

TABLE 3A-1

| component | component | Example 2-1-1 | Example 2-2-1 | Example 2-3-1 | Example 2-4-1 | Example 2-4-2 | Example 2-5-1 | Example 2-6-1 |
|---|---|---|---|---|---|---|---|---|
| C' | liquid paraffin | 25 | 25 | 25 | 25 | 35 | — | — |
| C' | cetyl ethylhexanoate | 40 | — | 40 | — | — | — | — |
| C' | wheat germ oil | — | 40 | — | 40 | 40 | 91 | 96 |
| D' | PEG-15 hydrogenated castor oil isostearate (HLB 6) | 20 | 20 | — | — | — | — | — |

TABLE 3A-1-continued

| component | component | Example 2-1-1 | Example 2-2-1 | Example 2-3-1 | Example 2-4-1 | Example 2-4-2 | Example 2-5-1 | Example 2-6-1 |
|---|---|---|---|---|---|---|---|---|
| D' | polyglyceryl-10 dioleate (HLB 11) | — | — | 20 | 20 | 20 | 5 | — |
| A' + B' | mixture of Example 1-1 | 15 | 15 | 15 | 15 | — | — | — |
| A' + B' | mixture of Example 1-2 | — | — | — | — | 5 | — | — |
| A' + B' | mixture of Example 1-2-7 | — | — | — | — | — | 4 | 4 |
| | total (wt %) | 100 | 100 | 100 | 100 | 100 | 100 | 100 |
| | evaluation of sweating | ○ | ○ | ○ | ○ | ○ | ⊙ | ○ |
| | evaluation of coloration | ○ | — | ○ | — | — | — | — |
| | qualitative evaluation of breaking strength | ○ | ○ | ○ | ○ | ○ | — | — |
| | evaluation of dissolution temperature | ○ | ○ | ○ | ○ | ○ | ○ | ○ |
| | breaking strength (g/cm²) of gel | 161.13 | 216.62 | 165.79 | 193.65 | 223.3 | — | — |

TABLE 3A-2

| component | component | Comp. Ex. 2-1-1 | Comp. Ex. 2-1-2 | Comp. Ex. 2-1-3 | Comp. Ex. 2-2-1 | Comp. Ex. 2-2-2 | Comp. Ex. 2-2-3 | Comp. Ex. 2-3-1 | Comp. Ex. 2-3-2 | Comp. Ex. 2-3-3 | Comp. Ex. 2-4-1 | Comp. Ex. 2-4-2 | Comp. Ex. 2-4-3 | Comp. Ex. 2-5-1 |
|---|---|---|---|---|---|---|---|---|---|---|---|---|---|---|
| C' | liquid paraffin | 25 | 25 | 25 | 25 | 35 | 25 | 25 | 35 | 25 | 25 | 35 | 25 | — |
| C' | cetyl ethylhexanoate | 40 | 40 | 40 | — | — | — | 40 | 40 | 40 | — | — | — | — |
| C' | wheat germ oil | — | — | — | 40 | 40 | 40 | — | — | — | 40 | 40 | 40 | 90 |
| D' | PEG-15 hydrogenated castor oil isostearate (HLB 6) | 20 | 20 | 20 | 20 | 20 | 20 | — | — | — | — | — | — | — |
| D' | polyglyceryl-10 dioleate (HLB 11) | — | — | — | — | — | — | 20 | 20 | 20 | 20 | 20 | 20 | 5 |
| A' + B' | mixture of Comparative Example 1-1 | 15 | — | — | 15 | — | — | 15 | — | — | 15 | — | — | — |
| A' + B' | mixture of Comparative Example 1-3 | — | 5 | — | — | 5 | — | — | 5 | — | — | 5 | — | — |
| A' + B' | mixture of Comparative Example 1-2 | — | — | 15 | — | — | 15 | — | — | 15 | — | — | 15 | 4 |
| | total (wt %) | 100 | 100 | 100 | 100 | 100 | 100 | 100 | 100 | 100 | 100 | 100 | 100 | 100 |
| | evaluation of sweating | ○ | × | ○ | ○ | × | ○ | ○ | × | ○ | ○ | × | ○ | × |
| | evaluation of coloration | ○ | ○ | × | — | — | — | ○ | ○ | × | — | — | — | — |
| | qualitative evaluation of breaking strength | Δ | × | Δ | Δ | Δ | Δ | Δ | × | Δ | Δ | × | Δ | — |
| | evaluation of dissolution temperature | × | ○ | × | × | ○ | × | × | ○ | × | × | ○ | × | × |
| | breaking strength (g/cm²) of gel | 124.46 | 98.8 | 120.6 | 134.52 | 121.44 | 115.47 | 150.04 | 53.21 | 107.09 | 155.32 | 87.37 | 145.05 | — |

As shown in Table 3A-1, it was confirmed that the compositions of the Examples were free of sweating phenomenon and superior in breaking strength.

Experimental Example 4

Removal of Solvent and Evaluation of Removal Rate:
At the proportions (wt %) shown in Table 4A, (A')-(B') were mixed and heated in advance to give uniform solutions. (C') at proportions (wt %) shown in Table 4A was placed in glass vials, and heated in an oil bath at a predetermined temperature (115° C.). To the heated mixture was added a uniform mixture of A' and B' and the mixture was mixed until it was uniformly dissolved. The amounts of the mixture of (A') and (B'), and (C') were measured and added such that the total amount of the mixture at the time of charging was 20 g. To remove the solvent at the time of warming, the lid of the vial was opened and the mixture was heated for 40 minutes in the state of an open system. The difference in the total composition weight between before heating and after heating was calculated as the weight of the removed solvent, and the removal rate of the solvent was calculated from the following formula.

Removal rate (%) of solvent=(amount of solvent removed from formulation(composition)/amount of solvent added to formulation(composition))×100

The mixture was cooled for not less than 3 hr at room temperature after removal of the solvent and the breaking strength of the solid or gel mixture was similarly measured as in Experimental Example 3.

The results are shown in Table 4A.

TABLE 4A

| | | formulation No. | | | |
|---|---|---|---|---|---|
| component | | Comparative Example 3-1 | Comparative Example 3-2 | Comparative Example 3-3 | Example 3-1 |
| C' | liquid paraffin (wt %) | 90 | 90 | 90 | 96 |
| B' | solvent used | 2-octyldodecanol | pentyleneglycol | oleyl alcohol | ethanol |
| | solvent (wt %) | 8 | 8 | 8 | 2 |
| A' | gelling agent (wt %) | 2 | 2 | 2 | 2 |
| | wt % of gelling agent necessary relative to oil (gelling agent/oil agent * 100) | 2.22 | 2.22 | 2.22 | 2.08 |
| | solvent removal rate | <5% | <5% | <5% | 90% |
| | breaking strength (g/cm$^2$) | 77.11 | 0.87 | 66.32 | 190.9 |
| | qualitative evaluation of breaking strength | X | X | X | ○ |

Experimental Example 5

Removal of Solvent and Evaluation of Removal Rate:

At the proportions (wt %) shown in Table 5A, (A')-(B') were mixed and heated in advance to give uniform solutions. (C') at proportions (wt %) shown in Table 4A was placed in glass vials, and heated in an oil bath at a predetermined temperature (115° C.). To the heated mixture was added a uniform mixture of A' and B' and the mixture was mixed until it was uniformly dissolved. The amounts of the mixture of (A') and (B'), and (C') were measured and added such that the total amount of the mixture at the time of charging was 20 g. To remove the solvent at the time of warming, the lid of the vial was opened and the mixture was heated for 40 minutes in the state of an open system (Example 4-2). When the solvent was not removed, the mixture was heated with the lid of the vial closed (Example 4-1). The removal rate of the solvent was calculated in the same manner as in Experimental Example 4.

Removal rate (%) of solvent=(amount of solvent removed from formulation(composition)/amount of solvent added to formulation(composition))×100

The mixture was cooled for not less than 3 hr at room temperature after removal of the solvent and the breaking strength of the solid or gel mixture was similarly measured as in Experimental Example 3.

The results are shown in Table 5A.

TABLE 5A

| | | formulation No. | |
|---|---|---|---|
| component | | Example 4-1 | Example 4-2 |
| C' | wt % of oil agent (liquid paraffin) | 96 | 96 |
| B' | wt % of solvent (ethanol) | 2 | 3 |
| A' | the total amount of added gelling agent | 2 | 1 |

TABLE 5A-continued

| | | formulation No. | |
|---|---|---|---|
| component | | Example 4-1 | Example 4-2 |
| | wt % of gelling agent necessary relative to oil (gelling agent/oil agent * 100) | 2.08 | 1.04 |
| | solvent removal rate | <5% | 90% |
| | breaking strength (g/cm$^2$) | 77.83 | 84 |

Due to the removal of ethanol, formation of a gel having the same degree of strength was observed even when a smaller amount of a gelling agent was used.

TABLE 6A

Reference Formulation Example
soft gel formulation for cleansing:

| component C' | wheat germ oil | 27 |
|---|---|---|
| component C' | cetyl ethylhexanoate | 18 |
| component C' | isopropyl myristate | 11 |
| component C' | tri(caprylic acid/capric acid)glyceryl | 11 |
| component C' | shea butter | 11 |
| component D' | polyglyceryl-10 dioleate | 17 |
| component D' | polyglyceryl-2 oleate | 3 |
| component B' | ethanol | 1.2 |
| component A' | dibutyl ethylhexanoyl glutamide (EB-21) | 0.6 |
| component A' | dibutyl lauroyl glutamide (GP-1) | 0.2 |
| | total (wt %) | 100 |

INDUSTRIAL APPLICABILITY

Using the gel composition of the present invention, cosmetics perfumery, quasi-drug and the like can be produced easily without damaging the components to be blended in cosmetic and the like.

DESCRIPTION

Title of the Invention: SOFT GEL COMPOSITION

TECHNICAL FIELD

The present invention relates to a gelling agent containing N-acyl acidic amino acid dialkylamide and a gel composition containing the gelling agent.

BACKGROUND ART

Low molecules of amino acid derivatives having three or more amide bonds such as dibutyl N-lauroyl-L-glutamide and dibutyl N-2-ethylhexanoyl glutamide are capable of gelling oils and is particularly known as a gelling agent superior in producing a solid gel with a high strength (breaking strength value not less than 200 g/cm$^2$) by solidifying a liquid oil agent. For example, using these gelling agents, a gel composition having a high strength which can be molded into a stick shape or the like can be obtained (patent document 1"). In addition, by utilizing a mixture of these gelling agents, an emulsion composition can also be converted to a gel having a high strength, and an emulsion gel having a high strength which can be molded into a stick shape or the like can be obtained (patent document 2").

On the other hand, in the cosmetic field, a completely different application is considered for a soft solid gel having a low strength compared to a hard gel having a high strength. For example, a hard gel is necessary mainly for shape forming and shape stability, and cannot impart melting and softness of oil. If a liquid cosmetic composition can be turned into a soft gel, texture such as thickening and smoothness at the time of use of the formulation can be improved. Furthermore, in stick cosmetics such as lip and the like, it is known that a low strength of a gel composition is important for improving touch when in use (ability to be applied beautifully and evenly) (patent document 5", Chapter 14). In addition, if a cosmetic generally used as liquid can be solidified into a soft gel, convenience in use such as stability of shape and ease of carrying can be improved without degrading the sense of use (patent document 4").

As a technique for obtaining a stick gel composition having a low strength, a technique is known in which a block copolymer with a high melting point is blended in an oil agent having a low melting point at a proportion of not less than 12% by weight, and a gelling agent of dibutylamide N-lauroyl-L-glutamate and dibutylamide N-2-ethylhexanoyl glutamate at a ratio of 3:1-1:1 is further blended in the composition. However, it is considered to be difficult to obtain a gel composition with smooth texture from a gel composition containing a large amount of a high molecular weight polymer. When a high molecular weight polymer is blended at a high concentration, moreover, problems occur in that superior texture cannot be achieved since spreadability of the gel composition on application is degraded and the like. In addition, since block copolymers have low solubility, it is necessary to add 20 wt % of a solvent in the formulation to dissolve the polymer (patent document 5"). On the other hand, when a soft gel composition is made from a low molecular gelling agent alone, a stability problem occurs in that the gel composition sweats (patent document 5", Chapter 1). dibutyl N-2-ethylhexanoyl glutamide is used for a technique for producing a stable emulsion composition containing a large amount of water (patent document 3").

However, a gel composition having a shape cannot be produced using this technique, and the obtained composition was a liquid composition.

In the case of a soft cream-like cosmetic, it is more conveniently used by filling in a container like a jar rather than a stick, and such jar type cosmetic is often used by taking with a finger. For the sense of use of a jar type product, therefore, it is very important that the cosmetic has moderate softness and can be easily taken with a finger. With the existing techniques, however, production of a stable and soft gel composition free of sweating which can be easily taken with a finger from a jar type container is considered to be difficult.

Document List

Patent Documents patent document 1": JP 4174994 B2 patent document 2": U.S. Pat. No. 7,347,990 B2 patent document 3": U.S. Pat. No. 8,591,871 B2 patent document 4": WO 2016052072 A1 patent document 5": U.S. Pat. No. 9,272,039 B2

SUMMARY OF THE INVENTION

Problems to be Solved by the Invention

The present invention aims to provide a gelling agent and a gel composition, which are soft, stable, have a good sense of use, and are optimal for the production of cosmetics and the like.

Means of Solving the Problems

In view of the above-mentioned problem, the present inventors have conducted intensive studies and found that a gel composition obtained by adding a gelling agent obtained by blending two or more kinds of N-acyl acidic amino acid dialkylamide at a particular ratio to an oil agent is a stable composition which is soft, does not leave solid gel particles when applied to the skin, turns into a smooth and thick liquid and shows extremely low sweating phenomenon, which resulted in the completion of the present invention.

That is, the present invention includes the following embodiments.

[1] A gelling agent comprising (A") (A"-1) at least one kind of N-acyl acidic amino acid dialkylamide represented by the formula (I):

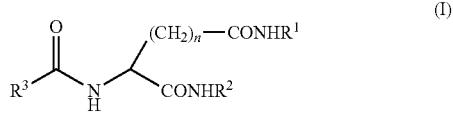

wherein R$^1$ and R$^2$ are each independently a straight chain or branched chain alkyl group having 1-7 carbon atoms, R$^3$ is a straight chain alkyl group having 3-15 carbon atoms, and n is 1 or 2, and (A"-2) at least one kind of N-acyl acidic amino acid dialkylamide represented by the formula (II):

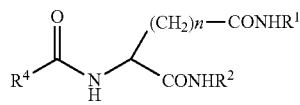

wherein $R^1$ and $R^2$ are each independently a straight chain or branched chain alkyl group having 1-7 carbon atoms, $R^4$ is a branched chain alkyl group having 3-15 carbon atoms, and n is 1 or 2, at a weight ratio (A"-1):(A"-2) of 1:1.5-1:1000.
[1-1] The gelling agent of [1], wherein $R^3$ is a straight chain alkyl group having 7-11 carbon atoms and $R^4$ is a branched chain alkyl group having 7-11 carbon atoms.
[2] The gelling agent of [1], wherein (A"-1) is dibutyl N-lauroyl glutamide.
[3] The gelling agent of [1] or [2], wherein (A"-2) is dibutyl N-2-ethylhexanoyl glutamide.
[4] The gelling agent of any one of [1] to [3], further comprising (B") at least one kind of solvent selected from the group consisting of alcohol, polyol, organic acid, organic amine, ether compound and silicone compound.
[4-1] The gelling agent of any one of [1] to [3], wherein (B") comprises at least one kind of solvent selected from the group consisting of ethanol, 2-octyldodecanol, oleyl alcohol, pentyleneglycol and myristic acid.
[4-2] The gelling agent of any one of [1] to [3], wherein (B") comprises at least one kind of solvent selected from the group consisting of ethanol, pentyleneglycol, dipropyleneglycol and 1,3-butyleneglycol.
[5] A gel composition comprising the gelling agent of any one of [1] to [4], and (C") an oil agent.
[6] The gel composition of [5], wherein (C") is at least one kind selected from the group consisting of an oil agent for cosmetics and an oil agent for pharmaceutical products.
[6-1] The gel composition of [5], wherein (C") is at least one kind selected from the group consisting of jojoba seed oil, wheat germ oil, isopropyl myristate, cetyl ethylhexanoate and tri(caprylic acid/capric acid)glyceryl.
[7] The gel composition of [5] or [6], wherein the total amount of the gelling agent of any one of [1] to [4] is 0.1-50 wt % relative to the total weight of the gel composition.
[8] The gel composition of any one of [5] to [7], further comprising (D") an emulsifier.
[8-1] The gel composition of [8], wherein (D") is an emulsifier with HLB 12-16.
[8-2] The gel composition of [8], wherein (D") is at least one selected from the group consisting of polyglyceryl-10 dioleate, polyglyceryl-10 cocoate, polyglyceryl-3 cocoate, PEG-40 glyceryl triisostearate and PEG-40 glyceryl isostearate.
[8-3] The gel composition of any one of [5] to [8-2], wherein the gel has a breaking strength of 15-150 g/cm$^2$.
[9] The gel composition of any one of [5] to [8-3], wherein the composition is a cosmetic, a perfumery or a quasi-drug composition.
[10] A cosmetic comprising the gel composition of any one of
[5] to [8-3].

Effect of the Invention

According to the present invention, a gel that turns into a soft, smooth liquid free of particles when applied can be provided.

According to the present invention, a stable gel with extremely less sweating phenomenon even at a high temperature or a low temperature can be provided.

Description of Embodiments

The present invention relates to a gelling agent containing (A") (A"-1) at least one kind of N-acyl acidic amino acid dialkylamide represented by the formula (I):

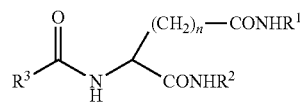

wherein $R^1$ and $R^2$ are each independently a straight chain or branched chain alkyl group having 1-7 carbon atoms, $R^3$ is a straight chain alkyl group having 3-15 carbon atoms, and n is 1 or 2, and
(A"-2) at least one kind of N-acyl acidic amino acid dialkylamide represented by the formula (II):

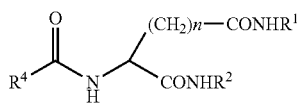

wherein $R^1$ and $R^2$ are each independently a straight chain or branched chain alkyl group having 1-7 carbon atoms, $R^4$ is a branched chain alkyl group having 3-15 carbon atoms, and n is 1 or 2, at a weight ratio (A"-1):(A"-2) of 1:1.5-1000.
(A") N-Acyl Acidic Amino Acid Dialkylamide
In the formula, $R^1$ and $R^2$ are each independently a straight chain or branched chain alkyl group having 1-7 carbon atoms. Examples of the straight chain or branched chain alkyl group having 1-7 carbon atoms include methyl group, ethyl group, isopropyl group, propyl group, butyl group, isobutyl group, sec-butyl group, tert-butyl group, pentyl group, sec-pentyl group, tert-pentyl group, isopentyl group, hexyl group, and heptyl group and the like. Since an effective gel strength can be exhibited with a small amount, a straight chain or branched chain alkyl group having 3-5 carbon atoms is preferable, and a butyl group is more preferable. It is more preferable that both $R^1$ and $R^2$ be straight chain or branched chain alkyl groups having 3-5 carbon atoms, and it is further preferable that both $R^1$ and $R^2$ be butyl groups.
In the formula, $R^3$ is a straight chain alkyl group having 3-15 carbon atoms.
Examples of the straight chain alkyl group having 3-15 carbon atoms include a propyl group, a butyl group, a pentyl group, a hexyl group, a heptyl group, an octyl group, a nonyl group, a decyl group, an undecyl group, a dodecyl group, a tridecyl group, a tetradecyl group, and a pentadecyl group and the like. Since an effective gel strength can be exhibited with a small amount, a straight chain alkyl group having 5-13 carbon atoms is preferable, a straight chain alkyl group having 7-11 carbon atoms is more preferable, and an undecyl group is most preferable.
In the formula, $R^4$ is a branched chain alkyl group having 3-15 carbon atoms.
Examples of the branched chain alkyl group having 3-15 carbon atoms include an isopropyl group, an isobutyl group, a sec-butyl group, a tert-butyl group, a sec-pentyl group, a tert-pentyl group, an isopentyl group, a 1-ethylpentyl group, an octyl group, a 2-ethylhexyl group, a tert-octyl group, an isononyl group, an isodecyl group, an isotridecyl group and the like. From the aspect that an effective gel strength can be exhibited with a small amount, preferred is a branched chain alkyl group having 5-13 carbon atoms, more preferred is a branched chain alkyl group having 7-11 carbon atoms, and most preferred is a 1-ethylpentyl group.

n is 1 or 2. When n is 1, (A") is N-acyl aspartic acid dialkylamide, and when n is 2, (A") is N-acyl glutamic acid dialkylamide. Since an effective gel strength can be exhibited with a small amount, n is preferably 2 (N-acylglutamic acid dialkylamide).

Specific examples of the N-acyl acidic amino acid dialkylamide (A"-1) include diisopropyl N-hexanoyl glutamide, dibutyl N-hexanoyl glutamide, di-sec-butyl N-hexanoyl glutamide, diisobutyl N-hexanoyl glutamide, diisopropyl N-octanoyl glutamide, dibutyl N-octanoyl glutamide, di-sec-butyl N-octanoyl glutamide, diisobutyl N-octanoyl glutamide, diisopropyl N-decanoyl glutamide, dibutyl N-decanoyl glutamide, di-sec-butyl N-decanoyl glutamide, diisobutyl N-decanoyl glutamide, dimethyl N-lauroyl glutamide, diethyl N-lauroyl glutamide, dipropyl N-lauroyl glutamide, diisopropyl N-lauroyl glutamide, dibutyl N-lauroyl glutamide, di-sec-butyl N-lauroyl glutamide, diisobutyl N-lauroyl glutamide, dipentyl N-lauroyl glutamide, dihexyl N-lauroyl glutamide, diisopropyl N-palmitoyl glutamide, dibutyl N-palmitoyl glutamide, di-sec-butyl N-palmitoyl glutamide, diisobutyl N-palmitoyl glutamide, diisopropyl N-myristoyl glutamide, dibutyl N-myristoyl glutamide, di-sec-butyl N-myristoyl glutamide, diisobutyl N-myristoyl glutamide, diisopropyl N-lauroyl aspartamide, dibutyl N-lauroyl aspartamide, di-sec-butyl N-lauroyl aspartamide, and diisobutyl N-lauroyl aspartamide, preferably, diisopropyl N-lauroyl glutamide, dibutyl N-lauroyl glutamide, di-sec-butyl N-lauroyl glutamide and diisobutyl N-lauroyl glutamide. More preferred is dibutyl N-lauroyl glutamide.

Specific examples of N-acyl acidic amino acid dialkylamide (A"-2) include dimethyl N-2-ethylhexanoyl glutamide, diethyl N-2-ethylhexanoyl glutamide, dipropyl N-2-ethylhexanoyl glutamide, diisopropyl N-2-ethylhexanoyl glutamide, dibutyl N-2-ethylhexanoyl glutamide, di-sec-butyl N-2-ethylhexanoyl glutamide, diisobutyl N-2-ethylhexanoyl glutamide, dipentyl N-2-ethylhexanoyl glutamide, dihexyl N-2-ethylhexanoyl glutamide, diisopropyl N-2-ethylhexanoyl aspartamide, dibutyl N-2-ethylhexanoyl aspartamide, di-sec-butyl N-2-ethylhexanoyl aspartamide, diisobutyl N-2-ethylhexanoyl aspartamide. Preferred are diisopropyl N-2-ethylhexanoyl glutamide, dibutyl N-2-ethylhexanoyl glutamide, di-sec-butyl N-2-ethylhexanoyl glutamide and diisobutyl N-2-ethylhexanoyl glutamide, and more preferred is dibutyl N-2-ethylhexanoyl glutamide.

As (A"), one or more kinds of (A"-1) and one or more kinds of (A"-2) from those mentioned above can be used in combination.

When (A"-1) dibutyl N-lauroyl glutamide (hereinafter sometimes to be abbreviated as GP-1) and (A"-2) dibutyl N-2-ethylhexanoyl glutamide (hereinafter sometimes to be abbreviated as EB-21) are used, the weight ratio (A"-1):(A"-2) is generally 1:1.5-1:1000, preferably 1:2-1:500, more preferably 1:2.5-1:100, from the aspect of the stability of the gel composition.

The N-acyl acidic amino acid dialkylamide represented by the formula (I) may be a stereoisomer such as optical isomer, diastereomer and the like, a mixture of any stereoisomers, or racemate.

(B") Solvent

The gelling agent of the present invention may further contain (B") a solvent. (B") is not particularly limited as long as it can dissolve (A"-1) and (A"-2), and those generally used for cosmetics, pharmaceutical products and the like can be mentioned. For example, alcohol, polyol(polyhydric alcohol), organic acid, organic amine, ether compound, silicone compound and the like can be mentioned.

Examples of the alcohol include lower alcohols such as isopropyl alcohol, t-butyl alcohol and ethanol, and higher alcohols such as 2-octyldodecanol, 2-hexyldecyl alcohol, lauroyl alcohol, isostearyl alcohol, 2-ethylhexanol, isononyl alcohol and oleyl alcohol. As lower alcohol, isopropyl alcohol, t-butyl alcohol and ethanol are preferable, and as higher alcohol, 2-hexyldecyl alcohol, lauroyl alcohol, oleyl alcohol and the like are preferable.

Examples of polyol(polyhydric alcohol) include pentyleneglycol, dipropyleneglycol, butyleneglycol (1,3-butanediol), propylene glycol (1,2-propanediol), 1,4-butanediol, 1,3-propanediol and the like, and polyols such as pentyleneglycol, dipropyleneglycol, 1,4-butanediol and the like are preferable.

In another embodiment, as polyol(polyhydric alcohol), polyols such as pentylene glycol, dipropylene glycol, 1,3-butylene glycol (1,3-butanediol), propylene glycol (1,2-propanediol), 1,4-butanediol, 1,3-propanediol and the like, and pentylene glycol, dipropylene glycol, 1,3-butanediol and the like are preferable.

Examples of the organic acid include lactic acid, capric acid, lauric acid, myristic acid, stearic acid, 12-hydroxystearic acid, ricinoleic acid, isostearic acid, 2-ethylhexanoic acid, isononanoic acid and the like, and lactic acid, capric acid, lauric acid, myristic acid, stearic acid, 12-hydroxystearic acid, ricinoleic acid, isostearic acid and the like are preferable. Among these, myristic acid and isostearic acid are more preferable.

Examples of the organic amine include monomethylamine hydrochloride, triethanolamine, lauryl dimethylamine N-oxide, oleyl dimethylamine N-oxide and the like, and organic amine such as triethanolamine and the like, and the like are preferable.

Examples of the ether compound include dimethylisosorbide, alkyl(C12-15) benzoate and the like, and alkyl(C12-15) benzoate and the like are preferable.

Examples of the silicone compound include cyclopentasiloxane, cyclohexasiloxane, amodimethicone and the like, and cyclohexasiloxane, amodimethicone and the like are preferable.

Among (B"), isopropyl alcohol, ethanol, oleyl alcohol, pentylene glycol, dipropylene glycol, 1,4-butanediol, lactic acid, capric acid, myristic acid, 12-hydroxystearic acid, isostearic acid, alkyl(C12-15) benzoate and cyclohexasiloxane are more preferable.

In another embodiment, among (B"), ethanol, 2-octyldodecanol, oleyl alcohol, pentylene glycol, dipropylene glycol, 1,3-butylene glycol and myristic acid are preferable, ethanol, pentylene glycol, dipropylene glycol and 1,3-butylene glycol are more preferable, and pentylene glycol, dipropylene glycol and 1,3-butylene glycol are more preferable.

The content of (B") in the gelling agent of the present invention is generally 0.5-9.5 parts by weight, preferably 0.6-9 parts by weight, more preferably 0.8-5 parts by weight, relative to the 1 part by total weight of (A"-1) and (A"-2) from the aspect that the uniform dissolution temperature of the formulation becomes low.

The shape of the gelling agent of the present invention is not particularly limited, and is, for example, liquid, gel, particle, solid, stick, sphere, sheet or the like. Of these, gel, solid, sphere and sheet are preferable.

(C") Oil Agent

A gel composition which is another embodiment of the present invention contains the above-mentioned gelling agent and (C") and can be generally obtained by dissolving the gelling agent in (C").

(C') in the present invention can be used without particularly restriction as long as it is an oil agent used for cosmetic, pharmaceutical products and the like. Examples thereof include liquid oil agent, semisolid oil agent, solid oil agent and the like, with preference given to a liquid oil agent.

Specifically, liquid oil agent such as straight chain or branched hydrocarbon oil such as liquid paraffin, light isoparaffin, liquid isoparaffin, squalane, squalene and the like; vegetable oils such as shea butter, almond oil, jojoba oil, olive oil, jojoba seed oil, maize germ oil, wheat germ oil, meadowfoam oil, sunflower oil, and the like; animal-derived fats and oils such as liquid lanolin and the like; ester oils such as fatty acid ester, polyhydric alcohol fatty acid ester (e.g., isopropyl myristate, cetyl ethylhexanoate, ethylhexyl palmitate, cetyl palmitate, isopropyl palmitate, tri(caprylic acid/capric acid)glyceryl, triethylhexanoin and the like);

acylamino acid esters such as isopropyl lauroyl sarcosine (Eldew (registered trade mark) SL-205), N-lauroyl-L-glutamic acid di(cholesteryl/octyldodecyl), hexyldecyl myristoyl methyl aminopropionate, dihexyldecyl lauroyl glutamate, diisostearyl lauroyl glutamate, dioctyldodecyl lauroyl glutamate, lauroyl glutamic acid bis(hexyldecyl/octyldodecyl), dioctyldodecyl lauroyl glutamate, dioctyldodecyl stearoyl glutamate and the like; phytosterol esters such as N-lauroyl-L-glutamic acid di(phytosteryl/2-octyldodecyl) and the like; silicone oil such as cyclopentasiloxane, dimethylpolysiloxane, dimethylcyclopolysiloxane, methylphenylpolysiloxane, methyl hydrogen polysiloxane, higher alcohol denatured organopolysiloxane, and the like, silicone oil of fluorine oil such as fluoropolyether, perfluoro alkylethersilicone and the like, and the like;

Semisolid oil agent such as cholesteryl esters such as cholestryl isostearate, cholestryl hydroxystearate, macadamia nut oil fatty acid cholesteryl, N-lauroyl-L-glutamic acid di(cholesteryl/behenyl/octyldodecyl) and the like; phytosterol esters such as N-lauroyl-L-glutamic acid di(phytosteryl/behenyl/2-octyldodecyl), myristoylmethyl-β-alanine (phytosteryl/decyltetradecyl)isostearic acid phytosteryl, phytosteryl oleate and the like; dipentaerythrityl fatty acid esters such as dipentaerythrityl hexaoxystearate, dipentaerythrityl rosinate and the like; triglycerides such as tri(caprylic acid/capric acid)glyceryl, tri(capuryl/capric/myristic/stearic acid) glycerides and the like; partially hydrogenated triglycerides such as hydrogenated oil and the like; lanolin, lanosterols, petrolatum and the like;

solid oil agents such as animal-derived wax, plant-derived wax, mineral wax, synthetic wax, specifically, rice bran wax, carnauba wax, candelilla wax, beeswax, spermaceti, ceresin, solid paraffin, microcrystalline wax, polyethylene wax, polyolefinwax and the like.

Among these, from the aspect of broad utility, hydrocarbon oil such as solid paraffin, liquid paraffin and the like, fatty acid ester oil such as cetyl ethylhexanoate, ethylhexyl palmitate, isopropyl myristate, isopropyl palmitate, tri(caprylic acid/capric acid)glyceryl, triethylhexanoin and the like, vegetable oil such as shea butter, almond oil, wheat germ oil, jojoba seed oil, olive oil, meadowfoam oil and the like, phytosterol esters such as N-lauroyl-L-glutamic acid di(phytosteryl/2-octyldodecyl) and the like, acylamino acid ester oil such as isopropyl lauroylsarcosine and the like, and the like are preferable.

In another embodiment, from the aspect of broad utility, hydrocarbon oils such as petrolatum, solid paraffin, liquid paraffin, and the like; silicone oil such as cyclopentasiloxane and the like; fatty acid ester oils such as cetyl ethylhexanoate, ethylhexyl palmitate, isopropyl myristate, isopropyl palmitate, tri(caprylic acid/capric acid)glyceryl, triethylhexanoin and the like; vegetable oils such as shea butter, almond oil, wheat germ oil, jojoba seed oil, olive oil, meadowfoam oil and the like; phytosterol esters such as N-lauroyl-L-glutamic acid di(phytosteryl/2-octyldodecyl) and the like, acylamino acid ester oil such as isopropyl lauroylsarcosine and the like, and the like are preferable, and jojoba seed oil, wheat germ oil, isopropyl myristate, cetyl ethylhexanoate and tri(caprylic acid/capric acid)glyceryl are more preferable.

The gel composition obtained by dissolving the gelling agent of the present invention in (C") generally contains a gelling agent 0.1-50 wt % and (C") 5-99.9 wt %, preferably 0.1-20 wt % and (C") 5-99.9 wt %, more preferably a gelling agent 0.5-15 wt % and (C") 15-99.5 wt %, further preferably a gelling agent 1-10 wt % and (C") 30-99.2 wt %, relative to the total weight of the gel composition, from the aspects of formation of a soft gel composition and improvement of the stability of the composition.

More specifically, from the aspects of formation of a soft gel composition, easy taking (easy scooping) when in use and improvement of stability of the composition, a composition containing (A"), (B") and (C") contains (A") 0.1-10 wt %, (B") 0-40 wt % and (C") 10-99.8 wt %, preferably (A") 0.2-5 wt %, (B") 0.2-25 wt % and (C") 20-98 wt %, more preferably (A") 0.5-3 wt %, (B") 0.5-20 wt % and (C") 30-95 wt %, relative to the total weight of the composition.

The breaking strength of the gel in the gel composition of the present invention is generally not more than 200 g/cm$^2$, preferably 15-150 g/cm$^2$, more preferably 15-70 g/cm$^2$. Here, the breaking strength of the gel is a value indicating the numerical value in g per unit square centimeter, which is the force required to break the gel, and can be measured using a gel compression-recovery measuring instrument such as FUDOH Rheometer D-series (manufactured by Rheotech Co., Ltd.).

(D") Emulsifier

The emulsifier in the present invention is not particularly limited as long as it is used for cosmetics, pharmaceutical products and the like, and nonionic emulsifiers can be mentioned.

Among the nonionic emulsifiers, emulsifiers generally having HLB 5-17 are generally used from the aspect of compatibility with oil. Particularly, an emulsifier having HLB 8-17 is preferable, and an emulsifier having HLB 10-16 is more preferable, from the aspects of reduction of sweating of the formulation and improvement of stability.

Examples of the emulsifier having HLB 5-8 include polyglyceryl-2 oleate, polyglyceryl-2 sesquicaprylate, PEG-20 glyceryl triisostearate, PEG-50 hydrogenated (hydrogenated) castor oil isostearate and the like, and polyglyceryl-2 oleate, PEG-50 hydrogenated castor oil isostearate are preferable.

Examples of the emulsifier having HLB 10-16 include PEG-8 glyceryl isostearate, polyglyceryl-10 cocoate, polyglyceryl-3 cocoate, PEG-7 glyceryl cocoate, polyglyceryl-10 dioleate, polyglyceryl-10 diisostearate, PEG-40 glyceryl triisostearate, PEG-40 glyceryl isostearate, polyglyceryl-10 trilaurate, hexaglyceryl tricaprylate and the like.

Among these, polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate and the like are preferably used.

In another embodiment, among the nonionic emulsifiers, nonionic emulsifiers generally having HLB 5-16 or HLB 5-17 are used from the aspect of compatibility with oil. Among those, from the aspect of less sweating of formulation and improved stability, emulsifiers having HLB 8-17 are preferable, emulsifiers having HLB 8-16 are more preferable, emulsifiers having HLB 10-16, and emulsifiers having HLB 12-16 are particularly preferable. It is also possible to use a mixture of a nonionic surfactant having a low HLB and a surfactant having a high HLB.

Examples of the emulsifier with HLB 10-16 include sorbeth-60 tetraoleate (tetraoleic acid polyoxyethylene(60) sorbit), PEG(polyethylene glycol)-8 glyceryl isostearate, PEG(polyethylene glycol)-7 glyceryl cocoate, polyglyceryl-10 dioleate, polyglyceryl-10 diisostearate, polyglyceryl-10 trilaurate, hexaglyceryl tricaprylate, polyglyceryl-10 cocoate, polyglyceryl-3 cocoate, PEG(polyethylene glycol)-40 glyceryl triisostearate, PEG(polyethylene glycol)-40 glyceryl isostearate, PEG(polyethylene glycol)-50 hydrogenated castor oil isostearate, polysorbate 60, sorbeth-30 tetraoleate, glyceryl stearate (SE: self-emulsifying type). Examples of the emulsifier with HLB 17 include PEG (polyethylene glycol)-100 stearate.

Examples of the emulsifier with HLB 5—less than 10 include polyglyceryl-2 stearate, polyglyceryl-2 oleate, polyglyceryl-2 sesquicaprylate, PEG(polyethylene glycol)-20 glyceryl triisostearate, PEG(polyethylene glycol)-15 hydrogenated castor oil isostearate, PEG(polyethylene glycol)-6 sorbitan oleate.

Among these, polyglyceryl-10 dioleate, PEG-8 glyceryl isostearate, polyglyceryl-10 cocoate, polyglyceryl-3 cocoate, PEG-40 glyceryl triisostearate, PEG-40 glyceryl isostearate, PEG-50 hydrogenated castor oil isostearate, polyglyceryl-2 oleate, PEG-15 hydrogenated castor oil isostearate, polysorbate 60, sorbeth-30 tetraoleate, glyceryl stearate (SE: self-emulsifying type) are preferable, polyglyceryl-10 dioleate, polyglyceryl-10 cocoate, polyglyceryl-3 cocoate, PEG-40 glyceryl triisostearate, PEG-40 glyceryl isostearate, PEG-50 hydrogenated castor oil isostearate, polyglyceryl-2 oleate, polysorbate 60, sorbeth-30 tetraoleate, glyceryl stearate (SE: self-emulsifying type) are more preferable, polyglyceryl-10 dioleate, polyglyceryl-10 cocoate, polyglyceryl-3 cocoate, PEG-40 glyceryl triisostearate, PEG-40 glyceryl isostearate are further preferable, and polyglyceryl-10 dioleate, polyglyceryl-10 cocoate, polyglyceryl-3 cocoate are particularly preferable.

The contents of the gelling agent of the present invention and (C") and (D") are generally gelling agent 0.1-50 wt %, (C") 5-99.8 wt % and (D") 0.1-80 wt %, preferably gelling agent 0.1-20 wt %, (C") 5-99.8 wt % and (D") 0.1-80 wt %, more preferably gelling agent 0.5-15 wt %, (C") 15-98.5 wt % and (D") 1-50 wt %, further preferably gelling agent 1-10 wt %, (C") 30-95 wt % and (D") 3-20 wt %, relative to the total weight of the gel composition, from the aspects of formation of a soft gel composition, easiness of taking when in use, sensory evaluation on application and improvement of stability of the formulation without stimulation.

More particularly, from the aspects of formation of a soft gel composition, easiness of taking when in use, sensory evaluation on application and improvement of stability of the formulation, a composition containing (A"), (B"), (C") and (D") generally contains (A") 0.1-10 wt %, (B") 0-40 wt %, (C") 10-99.7 wt % and (D") 0.1-80 wt %, preferably (A") 0.2-5 wt %, (B") 0.2-25 wt %, (C") 30-95 wt % and (D") 1-50 wt %, more preferably (A") 0.5-3 wt %, (B") 0.5-20 wt %, (C") 40-90 wt % and (D") 3-20 wt %, each relative to the total weight of the composition.

In the present invention, as preferable proportions of (A") and (D"), a composition containing not less than 0.5 wt % and not more than 2 wt % of (A") in which (A"-1):(A"-2) is 1:4-1:20, and about 3 wt % of (D") an emulsifier having HLB 10-17 can be mentioned.

While the form (shape) of the gel composition of the present invention is not particularly limited, it is, for example, gel, particle, solid, stick, sphere, sheet or the like. Among these, gel, solid, sphere or sheet is preferable.

While the production method of the gelling agent of the present invention is not particularly limited, for example, the object gelling agent can be obtained by stirring a mixture of (A") and (B") with heating until a uniform solution is formed, and thereafter cooling same as necessary. While the heating temperature varies depending on the kind and contents of (A") and (B"), it can be obtained by, for example, mixing-heating the mixture at 85-130° C. for 5-30 min in an oil bath or by a heater and leaving the mixture at room temperature.

The redissolution temperature (melting point) of the gel composition of the present invention is generally not more than 150° C., preferably not more than 130° C., more preferably not more than 110° C.

While the production method of the gel composition of the present invention is not particularly limited, the object gel composition can be obtained by, for example, mixing (A"), or a mixture of (A") and (B") with (C"), stirring the mixture with heating until a uniform solution is formed, and cooling the mixture as necessary. In addition, the object gel composition can be obtained by, for example, mixing (A"), or a mixture of (A") and (B") with a mixture containing (C") and (D"), stirring the mixture with heating until a uniform solution is formed, and cooling the mixture as necessary. While the heating temperature varies depending on the kind and contents of (A")-(D"), the gel composition can be obtained by, for example, mixing-heating the mixture in an oil bath or by using a heater at 85-130° C. for 5-30 min, and leaving the mixture at room temperature.

The dissolution temperature (melting point) of the gel composition of the present invention is generally not more than 150° C., preferably not more than 130° C., more preferably not more than 110° C.

In addition, the gel composition of the present invention can also contain components generally usable for cosmetics such as a gelling agent other than (A') of the present invention, humectant, flavor, various chelating agents, antiperspirant active ingredient, surfactants, various additives, various powders, and the like within the range where the effect of the present invention is not inhibited.

Examples of the moisturizer include glycerol, urea, PCA-Na (sodium pyrrolidonecarboxylate), hyaluronic acid, amino acid mixture, heparosan, ceramide and the like.

Examples of the flavor include linalool, limonene, menthol, peppermint oil, vanillin and the like.

While various chelating agents are not particularly limited, preferable examples include a chelator selected from the group consisting of triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicyl acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone, and salts thereof and a mixture thereof and the like.

Examples of the antiperspirant active ingredient include one kind selected from the group consisting of aluminum chlorohydrate, aluminum chloride, aluminum chlorohydrate allantoinate, aluminum sulfate, zinc oxide, zinc para-phenolsulfonate, and zirconium aluminum complex produced by reacting zirconylchloride with aluminum hydroxide and aluminumchlorohydroxide, and a mixture thereof. As used herein, the antiperspirant active ingredient refers to a component that suppresses sweating by causing strong adstriction of the skin.

Examples of the surfactant other than nonionic emulsifier include anionic surfactant such as N-long chain acylamino acid salts such as N-long chain acylglutamate, N-long chain acylglycine salt, N-long chain acylalanine salt, N-long chain acyl N-methyl-β-alanine salt and the like, N-long chain fatty acid acyl-N-methyltaurine salt, alkylsulfate and alkyleneoxide adduct thereof, fatty acid amide ether sulfate, metal salt or weak base salt of fatty acid, sulfosuccinic acid-based surfactant, alkyl phosphate and alkyleneoxide adduct thereof, alkylethercarboxylic acid, and the like; non-ionic surfactants such as ether type surfactants such as glycerolether and alkyleneoxide adduct thereof and the like, ether ester type surfactants such as alkylene oxide adduct of glycerolester, alkylene oxide adduct of sorbitan ester, polyoxyalkylene fatty acid ester and the like, ester type surfactants such as glycerol fatty acid ester, fatty acid polyglycerolester, sorbitan fatty acid ester, sucrose fatty acid ester and the like, alkylglucosides such as (caprylyl/capuryl) glucoside and the like, hydrogenated castor oil pyroglutamic acid diester and ethylene oxide adduct thereof, nitrogen-containing type non-ionic surfactants such as fatty acid alkanolamide and the like, and the like; cationic surfactant such as aliphatic amine salt (alkyl ammonium chloride, dialkyl ammonium chloride and the like), aromatic quaternary ammonium salt (quaternary ammonium salt thereof, benzalkonium salt thereof and the like), fatty acid acyl arginine ester, and the like; and amphoteric surfactant such as betaine type surfactant (carboxybetaine and the like), aminocarboxylic acid type surfactant, imidazoline type surfactant and the like, and the like.

Examples of the various additives include amino acids such as glycine, alanine, serine, threonine, arginine, glutamic acid, aspartic acid, isoleucine, leucine, valine and the like; water-soluble polymer such as polyamino acid including polyglutamic acid and polyaspartic acid and a salt thereof, gum arabics, alginates, xanthan gum, chitin, chitosan, water-soluble chitin, carboxyvinyl polymer, carboxymethylcellulose, hydroxyethylcellulose, hydroxypropyltrimethylammonium chloride, polychlorodimethylmethylenepiperidium, polyvinylpyrrolidone derivative, quartenary ammonium cationized protein, collagen decomposed product and a derivative thereof, acylated protein and the like; sugar alcohol such as mannitol and the like and alkylene oxide adduct thereof; animals and plants extract, nucleic acid, vitamin, enzyme, anti-inflammatory agent, antimicrobial agent, preservative, antioxidant, ultraviolet absorber, adiaphoretic, pigment, dye, oxidation dye, pH adjuster, pearly agent, wetting agent and the like, and the like.

Examples of the various powders include resin powder such as nylon beads, silicone beads and the like, nylon powder, metal fatty acid soap, yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, titanium oxide fine particles, zinc oxide fine particles, iron oxide fine particles, acylamino acid such as acyllysine, acylglutamic acid, acylarginine, acylglycine and the like, and the like can be mentioned, which may be further subjected to a surface treatment such as silicone treatment, fluorine compound treatment, silane coupling agent treatment, silane treatment organic titanate treatment, acylation lysine treatment, fatty acid treatment, metal soap treatment, oil treatment, amino acid treatment and the like.

The gel composition of the present invention can be used as it is or as cosmetic, perfumery or quasi-drug after blending the aforementioned components.

The gel composition of the present invention can be used as a base of cosmetic, perfumery, pharmaceutical product, quasi-drug and the like, a texture modifier, a thickener, a stabilizer or a gelling agent. The base refers to a component among the materials of cosmetic and the like, which is mainly used for giving a shape to a product and also called an excipient.

While the shape of the cosmetic, perfumery, pharmaceutical product and quasi-drug blended with the gel composition of the present invention is not particularly limited, for example, paste, gel, cream, particle, solid, stick, sphere, sheet and the like can be mentioned. Among these, paste, gel, solid, sphere and sheet are preferable.

Specific examples of the cosmetic, perfumery and quasi-drug include solid preparations such as adiaphoretic, chapstick, lip rouge, sun protectant, solid foundation, concealer, foundation primer, cleansing agent and the like, gel or gel dispersions or emulsions such as facial cleanser, cleansing gel, milky lotion, cream (massage cream, cold cream), moisture gel, facial mask, after shaving gel, milky liquid foundation, blush, mascara, shampoo, rinse, hair-growth drug, treatment, conditioner, tic, set lotion, hair cream, hair wax, hair mousse, permanent wave solution, hair dye, hair coloring, hair manicure, sunscreen oil, hand soap, and the like, aromatic, cataplasm and the like. Preferred are adiaphoretic, lip rouge, chapstick, cream, milky lotion, and sun protectant, and more preferred are adiaphoretic, lip rouge, cream, milky lotion, and sun protectant.

Specific examples of the pharmaceutical product include external preparations such as ointment, cream, gel and the like, adhesive preparation, suppository and the like.

Cosmetic, perfumery, pharmaceutical product and quasi-drug containing the gel composition of the present invention can be produced according to a conventional method.

EXAMPLE

While the present invention is explained in further detail by illustrating Examples, the present invention is not limited to the following Examples.

<Production Method of Gel>

A appropriate amount (wt %) of component A" was added to component B" at the ratio shown in Table 1B, and the mixture was heated and stirred in an oil bath to uniformly dissolve A" and B". An appropriate amount of the solution was added to solutions of an oil agent (component C") or an oil agent (component C") and an emulsifier (component D") previously heated and dissolved at the ratios shown in Tables 2B-6B, and the mixtures were heated and stirred until uniform dissolution. The solutions were filled in jar type 5 containers and stood at room temperature for 5 hr to give gel compositions.

Various blending examples of component A" and component B" in which the ratio of A"-1 and A"-2 components is different are shown in Table 1B.

TABLE 1B

|  |  | blend No. | | | | | | | | | | | |
| --- | --- | --- | --- | --- | --- | --- | --- | --- | --- | --- | --- | --- | --- |
|  |  | blend 1 | blend 2 | blend 3 | blend 4 | blend 5 | blend 6 | blend 7 | blend 8 | blend 9 | blend 10 | blend 11 | blend 12 |
| ratio → | EB-21:GP-1(A2:A1) → | 2:3 | 2:3 | 2:3 | 2:3 | 2:3 | 2:3 | 2.5:1 | 3:1 | 4:1 | 4:1 | 7:1 | 7:1 |
| component A" | dibutyl ethylhexanoyl glutamide (EB-21) | 16 | 20 | 8 | 8 | 8 | 8 | 14.3 | 30 | 32 | 16 | 17.5 | 17.5 |
|  | dibutyl lauroyl glutamide (GP-1) | 24 | 30 | 12 | 12 | 12 | 12 | 5.7 | 10 | 8 | 4 | 2.5 | 2.5 |
| component B" | ethanol | 60 | 50 |  |  |  |  |  | 60 | 60 |  |  |  |
| component B" | myristic acid |  |  | 80 |  |  |  |  |  |  |  |  | 80 |
| component B" | 2-octyldodecanol |  |  |  | 80 |  |  |  |  |  |  |  |  |
| component B" | oleyl alcohol |  |  |  |  | 80 |  |  |  |  |  |  |  |
| component B" | pentylene glycol |  |  |  |  |  | 80 | 80 |  |  | 80 | 80 |  |
|  | total (wt %) | 100 | 100 | 100 | 100 | 100 | 100 | 100 | 100 | 100 | 100 | 100 | 100 |

<Study of Uniform Dissolution Temperature of Composition>

An appropriate amount of component (B") was measured into a glass vial, and an appropriate amount of component (A") was added to component (B"). The mixture was heated and stirred in an oil bath to uniformly dissolve component (A") in component (B"). Component (C") was measured into a different glass vial, uniformly mixed and dissolved, an appropriate amount of a gelling agent solution was added to a solution of other components, and the mixture was mixed by stirring. The temperature of the bath was increased at intervals of 5° C., and the temperature was raised until the mixture became a uniform solution. The temperature at which the uniform solution of the mixture was obtained was taken as the uniform dissolution temperature of the formulation. In Examples 1-1 to 1-3, component (A") alone was directly added to component (C") instead of component (A")+(B"), and the uniform dissolution temperature of the formulation was examined.

<Evaluation of Softness of Gel>

The breaking strength of the gel was measured by FUDOH Rheometer D-series (manufactured by Rheotech Co., Ltd.). A gel composition with a flat surface set in the machine together with the container, and the measurement was performed using an adapter having a diameter of 10 mm under the conditions of an entrance speed of 6 cm/min and a load of 200 g. The breaking strength value was automatically calculated by the machine.

The following evaluation was made based on the breaking strength values:
very preferable (◎): 15-70 g/cm² (very soft gel was formed)
preferable (○): 71-150 g/cm² (soft gel was formed)
not very preferable (Δ): 151-300 g/cm² (formed gel is hard)
not preferable (x): higher than 300 g/cm² (formed gel is considerably hard).

<Evaluation of Sweating of Gel Formulation>
(1) Sweating of Gel (when Returned from −5° C. to 25° C.)
(1-1) The gel composition filled in a container was stored in a thermostatic tank at −5° C. overnight. The stored sample was taken out from the thermostatic tank at −5° C., and gradually warmed to 25° C. over 1 hr.
(1-2) The Sample was further Stored at Room Temperature for One Day.
Immediately after each of the operations of (1-1) and (1-2), the area of the droplets on the surface of the gel composition was confirmed. The area of the droplets covering the surface of the gel composition and the total area of the gel composition were measured by an image processing (Image J), the former was divided by the latter, and the calculated value was shown as percentage ($K$): calculated value ($K$)=(area of droplet/total area of gel composition)×100%.

The evaluation points were given to the gel compositions after each of the operations (1-1) and (1-2) according to the following criteria.
5 points: value of Knot more than 0.5%
4.5 points: value of K higher than 0.5% and not more than 2%
4 points: value of K higher than 2% and not more than 5%
3.5 points: value of K higher than 5% and not more than 10%
3 points: value of K higher than 10% and not more than 15%
2.5 points: value of K higher than 15% and not more than 25%
2 points: value of K higher than 25% and not more than 35%
1.5 points: value of K higher than 35% and not more than 50%
1 point: value of K higher than 50%

Using the average of the evaluation points of the gel compositions after each of the operations (1-1) and (1-2), sweating of the gelling agents (when returned from −5° C. to 25° C.) was evaluated according to the following evaluation criteria.
very preferable (◎): evaluation average points of not less than 4.0
preferable (○): evaluation average points of not less than 3.0 and less than 4.0
not very preferable (Δ): evaluation average points of not less than 2.0 and less than 3.0 unpreferable (x): evaluation average points of not less than 1.0 and less than 2.0

(2) Sweating of Gel (40° C.)

(2-1) The Gel Composition Filled in a Container was Stored in a Thermostatic Tank at 40° C. Overnight.

(2-2) The Sample was further Stored at Room Temperature for One Day.

Immediately after each of the operations of (2-1) and (2-2), the area of the droplets on the surface of the gel composition was confirmed and evaluated in the same manner as in the above-mentioned (1).

(3) Stability Evaluation Total Points

In each gel composition, the total evaluation points after respective operations (1-1), (1-2), (2-1) and (2-2) were evaluated as the stability evaluation total points of the gel composition. The total evaluation points of the gel composition before and after addition of a new component were evaluated. When the stability evaluation total points increased by the addition of the component, the gel composition was judged to have become more stable by the addition of the component.

<Evaluation of Easiness of Taking from Container in Use>

Six expert panelists scooped with one finger a gel composition filled in a jar type container, and evaluated ease of penetration of the finger into the gel composition and easiness of taking the gel composition with one finger according to the following criteria.

1) easy penetration into the gel composition without destroying the whole shape of the composition and easy scooping of the gel composition with one finger . . . 4 points 2) penetration into the gel composition without destroying the whole shape of the composition and scooping of the gel composition with one finger . . . 3 points 3) difficult penetration into the gel composition without destroying the whole shape of the composition and difficult scooping of the gel composition with one finger . . . 2 points 4) unattainable penetration into the gel composition without destroying the whole shape of the composition and unattainable scooping of the gel composition with one finger . . . 1 point Based on the average evaluation points by the expert panelists, the following determination was made.

⊙: evaluation average points 3.5 or above

○: evaluation average points 2.5 or above and less than 3.5

Δ: evaluation average points 1.5 or above and less than 2.5 x: evaluation average points less than 1.5

<Sensory Evaluation when Applied to Skin>

Whether a smooth and thick liquid that does not leave solid gel particles on the skin when applied to the skin is provided was evaluated. Six expert panelists measured 0.2 g of the gel composition, placed same on the back of the hand, rubbed with a finger five times, and broke the gel composition into a liquid. Easiness of application of the gel composition during application thereof was evaluated according to the following criteria.

1) when broken by rubbing, solid gel particle do not remain and gel composition is broken very smoothly to give thick liquid composition . . . 4 points 2) when broken by rubbing, solid gel particle do not remain mostly and gel composition is broken smoothly to give thick liquid composition . . . 3 points 3) when broken by rubbing, solid gel particles remain a little, gel composition is not easily broken smoothly and thick liquid composition is not easily afforded . . . 2 points 4) when broken by rubbing, solid gel particles remain a lot, gel composition is not broken smoothly and thick liquid composition is not afforded . . . 1 point Based on the average evaluation points by the expert panelists, the following determination was made.

⊙: evaluation average points 3.5 or above

○: evaluation average points 2.5 or above and less than 3.5

Δ: evaluation average points 1.5 or above and less than 2.5 x: evaluation average points less than 1.5

The results are shown in Tables 2B-6B.

As shown in Table 2B, it was found that addition of component B" enabled uniform dissolution of the formulation at a lower temperature, thus affording benefits in production.

TABLE 2B

| | | evaluation formulation No. | | | | | |
| --- | --- | --- | --- | --- | --- | --- | --- |
| | | Example 1-1 | Example 1-2 | Example 1-3 | Example 1-4 | Example 1-5 | Example 1-6 |
| | | EB-21:GP-1(A2:A1) | | | | | |
| component | | 4:1 | 4:1 | 4:1 | 4:1 | 4:1 | 4:1 |
| component C" | wheat germ oil | 98.5 | | | 92.5 | | |
| component C" | tri(caprylic acid/capric acid)glyceryl | | 98.5 | | | 92.5 | |
| component C" | cetyl ethylhexanoate | | | 98.5 | | | 92.5 |
| component A" − 2 | EB-21 | 1.2 | 1.2 | 1.2 | | | |
| component A" − 1 | GP-1 | 0.3 | 0.3 | 0.3 | | | |
| component A" + B" | mixtureof blend 10 | | | | 7.5 | 7.5 | 7.5 |
| | total (wt %) | 100.0 | 100.0 | 100.0 | 100.0 | 100.0 | 100.0 |
| evaluation items | uniform dissolution temperature (° C.) of formulation | >145 | >125 | >135 | <105 | <95 | <95 |
| | softness of gel | ○ | ○ | ○ | ⊙ | ⊙ | ⊙ |
| | sweating of gel (40° C.) | ○ | ○ | ○ | ⊙ | ○ | ○ |
| | sweating of gel (−5° C. → 25° C.) | ○ | ○ | ○ | ○ | ○ | ○ |
| | easiness of taking when in use | ○ | ○ | ○ | ○ | ○ | ○ |
| | sensory evaluation on application | ○ | ○ | ○ | ○ | ⊙ | ⊙ |

In Example 1-1 to Example 1-3, satisfactory soft gel compositions were obtained. In Examples 1-4 to 1-6, satisfactory soft gel compositions were obtained even at a low production temperature by blending component B".

Comparison of the properties of the gel compositions having different-blending ratios of A"-1 and A"-2 components is shown in Tables 3B and 4B.

TABLE 3B

| | | evaluation formulation No. | | | |
|---|---|---|---|---|---|
| | | Comparative Example 2-1 | Comparative Example 2-2 | Comparative Example 2-3 | Comparative Example 2-4 |
| | | EB-21:GP-1 (A2:A1) | | | |
| component | | 2:3 | 2:3 | 2:3 | 2:3 |
| component C" | wheat germ oil | 92.5 | 96.25 | | |
| component C" | tri(caprylic acid/capric acid)glyceryl | | | 92.5 | |
| component C" | cetyl ethylhexanoate | | | | 92.5 |
| component A" + B" | mixture of blend 6 | 7.5 | | | |
| component A" + B" | mixture of blend 3 | | | 7.5 | 7.5 |
| component A" + B" | mixture of blend 1 | | 3.75 | | |
| | total (wt %) | 100.0 | 100.0 | 100.0 | 100.0 |
| evaluation item | softness of gel | ○ | Δ | Δ | Δ |
| | sweating of gel (40° C.) | Δ | Δ | Δ | ○ |
| | sweating of gel (−5° C. → 25° C.) | X | Δ | Δ | ○ |
| | easiness of taking when in use | X | X | X | X |
| | sensory evaluation on application | X | X | X | X |

TABLE 4B

| | | evaluation formulation No. | | | |
|---|---|---|---|---|---|
| | | Example 2-1 | Example 2-2 | Example 2-3 | Example 2-4 |
| | | EB-21:GP-1 (A2:A1) | | | |
| component | | 7:1 | 7:1 | 4:1 | 4:1 |
| component C" | wheat germ oil | 92.5 | 96.25 | | |
| component C" | tri(caprylic acid/capric acid)glyceryl | | | 92.5 | |
| component C" | cetyl ethylhexanoate | | | | 92.5 |
| component A" + B" | mixture of blend 11 | 7.5 | | | |
| component A" + B" | mixture of blend 12 | | | 7.5 | 7.5 |
| component A" + B" | mixture of blend 9 | | 3.75 | | |
| | total (wt %) | 100.0 | 100.0 | 100.0 | 100.0 |
| evaluation item | softness of gel | ⊙ | ⊙ | ⊙ | ⊙ |
| | sweating of gel (40° C.) | ⊙ | ⊙ | ⊙ | ⊙ |
| | sweating of gel (−5° C. → 25° C.) | ○ | ⊙ | ○ | ○ |
| | easiness of taking when in use | ○ | ○ | ○ | ○ |
| | sensory evaluation on application | ○ | ○ | ○ | ○ |

As shown in Table 5B, it was confirmed that the addition of component A" further improved stability of the gel compositions.

TABLE 5B

| | | Ex. 3-1 | Ex. 3-2 | Ex. 3-3 | Ex. 3-4 | Ex. 3-5 | Ex. 3-6 | Ex. 3-7 | Ex. 3-8 | Ex. 3-9 | Ex. 3-10 | Ex. 3-11 |
|---|---|---|---|---|---|---|---|---|---|---|---|---|
| | | EB-21:GP-1(A2:A1) | | | | | | | | | | |
| | | 7:1 | 7:1 | 7:1 | 7:1 | 7:1 | 7:1 | 7:1 | 7:1 | 7:1 | 7:1 | 7:1 |
| component C" | jojoba seed oil | | | | | | | | | 92.5 | 87.5 | 87.5 |
| component C" | tri(caprylic acid/capric acid)glyceryl | 92.5 | 87.5 | | | | | | | | | |
| component C" | cetyl ethylhexanoate | | | 92.5 | 87.5 | 87.5 | 87.5 | 87.5 | 87.5 | | | |
| component A" + B" | mixture of blend 11 | 7.5 | 7.5 | 7.5 | 7.5 | 7.5 | 7.5 | 7.5 | 7.5 | 7.5 | 7.5 | 7.5 |
| component D" | polyglyceryl-10 dioleate (HLB11) | | 5.0 | | 5.0 | | | | | | | |

TABLE 5B-continued

|  |  | Ex. 3-1 | Ex. 3-2 | Ex. 3-3 | Ex. 3-4 | Ex. 3-5 | Ex. 3-6 | Ex. 3-7 | Ex. 3-8 | Ex. 3-9 | Ex. 3-10 | Ex. 3-11 |
|---|---|---|---|---|---|---|---|---|---|---|---|---|
|  |  | \multicolumn{11}{c}{EB-21:GP-1(A2:A1)} |
|  |  | 7:1 | 7:1 | 7:1 | 7:1 | 7:1 | 7:1 | 7:1 | 7:1 | 7:1 | 7:1 | 7:1 |
| component D" | PEG-40 glyceryl triisostearate (HLB11) |  |  |  |  | 5.0 |  |  |  |  |  |  |
| component D" | PEG-40 glyceryl isostearate (HLB15) |  |  |  |  |  | 5.0 |  |  |  | 5.0 |  |
| component D" | polyglyceryl-10 cocoate (HLB16) |  |  |  |  |  |  | 5.0 |  |  |  | 5.0 |
| component D" | polyglyceryl-3 cocoate (HLB12) |  |  |  |  |  |  |  | 5.0 |  |  |  |
|  | total (wt %) | 100.0 | 100.0 | 100.0 | 100.0 | 100.0 | 100.0 | 100.0 | 100.0 | 100.0 | 100.0 | 100.0 |
|  | evaluation item |  |  |  |  |  |  |  |  |  |  |  |
|  | breaking strength of gel (g/cm$^2$) | 56 | 47 | 62 | 39 | 33 | 43 | 49 | 43 | 15 | 29 | 24 |
|  | sweating of gel (40° C.) | 4 | 5 | 4.5 | 5 | 5 | 5 | 5 | 5 | 3 | 5 | 5 |
|  | sweating of gel (40° C.) → one day later | 5 | 5 | 5 | 5 | 5 | 5 | 5 | 5 | 3 | 5 | 5 |
|  | sweating of gel (−5° C. → 25° C.) | 3.5 | 5 | 3.5 | 5 | 4.5 | 5 | 5 | 5 | 3 | 3.5 | 3.5 |
|  | sweating of gel (−5° C. → 25° C.) → one day later | 3.5 | 5 | 3.5 | 5 | 5 | 5 | 5 | 5 | 3 | 4 | 3.5 |
|  | stability evaluation total points | 16 | 20 | 16.5 | 20 | 19.5 | 20 | 20 | 20 | 12 | 17.5 | 17 |
|  | increase of stability evaluation total points by addition of component D | — | 4 | — | 3.5 | 3 | 3.5 | 3.5 | 3.5 | — | 5.5 | 5 |

Comparison of the properties of actual gel cleansing formulations for cosmetics is shown in Table 6B.

TABLE 6B

|  |  | Comp. Ex. 4-1 | Comp. Ex. 4-2 | Comp. Ex. 4-3 | Comp. Ex. 4-4 | Ex. 4-1 | Ex. 4-2 | Ex. 4-3 | Ex. 4-4 |
|---|---|---|---|---|---|---|---|---|---|
|  |  | \multicolumn{8}{c}{EB-21:GP-1(A2:A1)} |
| component |  | 2:3 | 2:3 | 2:3 | 2:3 | 3:1 | 2.5:1 | 7:1 | 7:1 |
| component C" | wheat germ oil | 23.5 | 23.5 | 23.5 | 26 | 26 | 26.6 | 25.5 | 27.5 |
| component C" | cetyl ethylhexanoate | 16 | 16 | 16 | 18 | 18 | 18 | 16.5 | 19.5 |
| component C" | isopropyl myristate | 9.5 | 9.5 | 9.5 | 10 | 11 | 10.7 | 9.4 | 9.5 |
| component C" | tri(caprylic acid/capric acid)glyceryl | 9.5 | 9.5 | 9.5 | 10 | 11 | 10.7 | 10.4 | 15 |
| component C" | shea butter | 10 | 10 | 10 | 11 | 11 | 10.7 | 10.4 |  |
| component D" | polyglyceryl-10 dioleate | 14 | 14 | 14 | 16 | 17 | 16 | 17.5 | 18.2 |
| component D" | polyglyceryl-2 oleate | 2.5 | 2.5 | 2.5 | 3 | 3 | 3 | 2.8 | 2.8 |
| component A" + B" | mixture of blend 4 | 15 |  |  |  |  |  |  |  |
| component A" + B" | mixture of blend 6 |  | 15 |  |  |  |  |  |  |
| component A" + B" | mixture of blend 5 |  |  | 15 |  |  |  |  |  |
| component A" + B" | mixture of blend 2 |  |  |  | 6 |  |  |  |  |
| component A" + B" | mixture of blend 8 |  |  |  |  | 3 |  |  |  |
| component A + B | mixture of blend 7 |  |  |  |  |  | 4.3 |  |  |
| component A + B | mixture of blend 11 |  |  |  |  |  |  | 7.5 | 7.5 |
|  | total (wt%) | 100 | 100 | 100 | 100 | 100 | 100 | 100 | 100 |
|  | evaluation item |  |  |  |  |  |  |  |  |
|  | softness of gel | Δ | ○ | Δ | Δ | ⊙ | ⊙ | ⊙ | ⊙ |
|  | sweating of gel (40° C.) | Δ | x | x | ○ | ⊙ | ○ | ⊙ | ⊙ |
|  | sweating of gel (−5° C. → 25° C.) | Δ | x | x | Δ | ⊙ | ○ | ⊙ | ⊙ |
|  | easiness of taking when in use | x | x | x | x | ○ | ○ | ⊙ | ⊙ |
|  | sensory evaluation on application | x | x | x | x | ○ | ○ | ⊙ | ⊙ |

TABLE 7B

|  | Reference Formulation Example soft gel formulation for cleansing: |  |
|---|---|---|
| component C" | wheat germ oil | 27.4 |
| component C" | cetyl ethylhexanoate | 19.4 |
| component D" | polyglyceryl-10 dioleate | 18.4 |
| component C" | tri(caprylic acid/capric acid)glyceryl | 15.5 |
| component C" | isopropyl myristate | 9.0 |
| component D" | polyglyceryl-2 oleate | 2.8 |
| component A" | dibutyl ethylhexanoyl glutamide (EB-21) | 1.3 |
| component A" | dibutyl lauroyl glutamide (GP-1) | 0.2 |
| component B" | dipropyleneglycol | 6.0 |
|  | flavor | q.s. |
|  | total (wt %) | 100.0 |

INDUSTRIAL APPLICABILITY

Using the gelling agent and gel composition of the present invention, cosmetic, perfumery, quasi-drug and the like with soft and smooth sense of use can be produced.

This application is based on patent application Nos. 2016-208184, 2017-061620, 2016-208183 and 2017-028516 filed in Japan, the contents of which are incorporated in full herein.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A gel composition, comprising:
(A") 0.5 to 2 wt % of a mixture of dibutyl N-lauroyl glutamide (A"-1) and dibutyl N-2-ethylhexanoyl glutamide (A"-2) in a weight ratio (A"-1):(A"-2) of 1:4 to 1:20;
formula (1);
(B") 0.5 to 20 wt % of at least one solvent selected from the group consisting of ethanol, 2-octyldodecanol, oleyl alcohol, pentyleneglycol, and myristic acid;
(C") 30 to 95 wt % of at least one oil agent selected from the group consisting of petrolatum, solid paraffin, liquid paraffin, cyclopentasiloxane, cetyl ethylhexanoate, ethylhexyl palmitate, isopropyl myristate, isopropyl palmitate, tri(caprylic acid/capric acid)glyceryl, triethylhexanoin, shea butter, almond oil, wheat germ oil, jojoba seed oil, olive oil, meadowfoam oil, N-lauroyl-L-glutamic acid di(phytosteryl/2-octyldodecyl), and isopropyl lauroylsarcosine; and
optionally, (D") 3 to 20 wt % of at least one emulsifier selected from the group consisting of polyglyceryl-10 dioleate, polyglyceryl-10 cocoate, polyglyceryl-3 cocoate, PEG-40 glyceryl triisostearate, and PEG-$0 &rend isostearate,
wherein the breaking strength of the gel composition is not more than 200 g/cm², and
wherein all wt % are relative to the total weight of the gel composition.

2. The gel composition according to claim 1, wherein (C') said at least ne oil agent is at least one oil agent for cosmetics or oil a, ent for pharmaceutical product selected from the group consisting of jojoba seed oil, wheat germ oil, isopropyl myristate, cetyl ethylhexanoate and tri(caprylic acid/capric acid)glyceryl.

3. The gel composition according to claim 1, further comprising (D") the at least one emulsifier.

4. The gel composition according to claim 1, wherein the breaking strength of the gel composition is 15 to 150 g/cm².

5. The gel composition according to claim 1, which is contained in a cosmetic, a perfumery or a quasi-drug composition.

6. The gel composition according to claim 1, wherein the dissolution temperature (melting point) of the gel composition is not more than 110° C.

7. The gel composition according to claim 1, which is free from dipropylene glycol.

8. The gel composition according to claim 1, wherein the breaking strength of the gel composition is 15 to 70 g/cm².

* * * * *

UNITED STATES PATENT AND TRADEMARK OFFICE
CERTIFICATE OF CORRECTION

PATENT NO. : 11,446,224 B2
APPLICATION NO. : 16/289857
DATED : September 20, 2022
INVENTOR(S) : Biswas It is certified that error appears in the above-identified patent and that said Letters Patent is hereby corrected as shown below:

On the Title Page

Column 2, Item (57), under "ABSTRACT", Line 7, delete "DESCRIPTION)" and insert -- DESCRIPTION --, therefor.

In the Specification

In Column 1, Line 9, after "Patent" delete "m".

In Column 9, Line 14, delete "(pulmitoleic" and insert -- (palmitoleic --, therefor.

In Column 9, Line 34, after "preferably" delete "m".

In Column 11, Line 28, after "methyl" delete "m".

In Column 11, Line 58, delete "rhea" and insert -- shea --, therefor.

In Column 14, Line 63, delete "quartenary" and insert -- quaternary --, therefor.

In Column 19, Line 16, delete "past" and insert -- part --, therefor.

In Column 47, Line 32, delete "quartenary" and insert -- quaternary --, therefor.

In Column 53, under "TABLE 3A-1-continued", Line 4, delete "mixtureof" and insert -- mixture of --, therefor.

In Column 53, under "TABLE 3A-1-continued", Line 5, delete "mixtureof" and insert -- mixture of --, therefor.

In Column 53, under "TABLE 3A-1-continued", Line 6, delete "mixtureof" and insert -- mixture of --, Signed and Sealed this
Fifth Day of September, 2023

Katherine Kelly Vidal
*Director of the United States Patent and Trademark Office*

CERTIFICATE OF CORRECTION (continued)
U.S. Pat. No. 11,446,224 B2 therefor.

In Column 67, Line 59, delete "quartenary" and insert -- quaternary --, therefor.

In Column 70, Line 44, delete "Knot" and insert -- K not --, therefor.

In Column 72, under "TABLE 2B", Line 11, delete "mixtureof" and insert -- mixture of --, therefor.

In Column 75, under "TABLE 5B-continued", Line 11, delete "gell" and insert -- gel --, therefor.

In the Claims

In Column 77, Claim 1, Line 17, delete "formula (1);".

In Column 78, Claim 1, Lines 4-5, delete "PEG-$0 &rend" and insert -- PEG-40 glyceryl --, therefor.

In Column 78, Claim 2, Line 10, delete "(C′)" and insert -- (C″) --, therefor.

In Column 78, Claim 2, Line 11, delete "ne" and insert -- one --, therefor.

In Column 78, Claim 2, Line 12, delete "a, ent" and insert -- agent --, therefor.